US010296720B2

(12) United States Patent
Jung et al.

(10) Patent No.: US 10,296,720 B2
(45) Date of Patent: *May 21, 2019

(54) COMPUTATIONAL SYSTEMS AND METHODS RELATED TO NUTRACEUTICALS

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Lowell L. Wood, Jr., Bellevue, WA (US)

(73) Assignee: Gearbox LLC, Bellevue, WA (US)

( * ) Notice: Subject to any disclaimer, the term of this patent is extended or adjusted under 35 U.S.C. 154(b) by 1845 days.

This patent is subject to a terminal disclaimer.

(21) Appl. No.: 11/824,529

(22) Filed: Jun. 28, 2007

(65) Prior Publication Data

US 2008/0046395 A1 Feb. 21, 2008

Related U.S. Application Data

(63) Continuation-in-part of application No. 11/453,571, filed on Jun. 14, 2006, now abandoned, and a continuation-in-part of application No. 11/478,341, filed on Jun. 28, 2006, now abandoned, and a continuation-in-part of application No. 11/478,296, filed on Jun. 28, 2006, now abandoned, and a continuation-in-part of application No. 11/486,998, filed on Jul. 14, 2006, now abandoned, and a continuation-in-part of application No. 11/486,973, filed on Jul. 14, 2006, now abandoned, and a continuation-in-part of application No. 11/474,109, filed on Jun. 23, 2006, now abandoned, and a continuation-in-part of application No. 11/515,357, filed on Sep. 1, 2006, now Pat. No. 8,340,944, and a continuation-in-part of application No. 11/518,540, filed on Sep. 8, 2006, now Pat. No. 8,297,028, and a continuation-in-part of application No. 11/523,766, (Continued)

(51) Int. Cl.
*G06F 19/00* (2018.01)

(52) U.S. Cl.
CPC .......... *G06F 19/3475* (2013.01); *G06F 19/00* (2013.01)

(58) Field of Classification Search
CPC ........ A61K 38/00; G06Q 50/22; G06Q 50/24; G01T 1/02; G06F 19/326; G06F 19/3437
USPC ....................................................... 705/2–3
See application file for complete search history.

(56) References Cited

U.S. PATENT DOCUMENTS 4,009,078 A 2/1977 Wilkins et al.
4,257,041 A 3/1981 Masucci
(Continued)

FOREIGN PATENT DOCUMENTS

JP 61002060 A 1/1986
WO WO 97/14393 4/1997
(Continued)

OTHER PUBLICATIONS

U.S. Appl. No. 11/524,084, Jung et al.
(Continued)

*Primary Examiner* — Reginald R Reyes

(57) ABSTRACT

The present disclosure relates to computational systems and methods related to nutraceuticals.

28 Claims, 39 Drawing Sheets

Related U.S. Application Data filed on Sep. 18, 2006, now abandoned, and a continuation-in-part of application No. 11/523,809, filed on Sep. 18, 2006, now abandoned, and a continuation-in-part of application No. 11/637,638, filed on Dec. 11, 2006, now Pat. No. 7,927,787, and a continuation-in-part of application No. 11/637,616, filed on Dec. 11, 2006, now abandoned, and a continuation-in-part of application No. 11/314,945, filed on Dec. 20, 2005, now abandoned, and a continuation-in-part of application No. 11/291,482, filed on Nov. 30, 2005, now abandoned, and a continuation-in-part of application No. 11/824,604, filed on Jun. 28, 2007, now abandoned.

(56) References Cited

U.S. PATENT DOCUMENTS

| | | |
|---|---|---|
| 4,293,845 A | 10/1981 | Villa-Real |
| 4,436,378 A | 3/1984 | Kirkman |
| 4,446,138 A | 5/1984 | Pack |
| 4,567,185 A | 1/1986 | Sackner |
| H201 H | 1/1987 | Yager |
| 4,729,636 A | 3/1988 | Te Velde et al. |
| 4,807,967 A | 2/1989 | Veenvliet et al. |
| 4,838,275 A | 6/1989 | Lee |
| 4,847,764 A | 7/1989 | Halvorson |
| 4,857,716 A | 8/1989 | Gombrich et al. |
| 5,006,343 A | 4/1991 | Benson et al. |
| 5,054,493 A | 10/1991 | Cohn et al. |
| 5,093,268 A | 3/1992 | Leventis et al. |
| 5,176,285 A | 1/1993 | Shaw |
| 5,279,294 A | 1/1994 | Anderson et al. |
| 5,284,656 A | 2/1994 | Platz et al. |
| 5,300,302 A | 4/1994 | Tachon et al. |
| 5,307,263 A | 4/1994 | Brown |
| 5,354,934 A | 10/1994 | Pitt et al. |
| 5,412,560 A | 5/1995 | Dennision |
| 5,490,962 A | 2/1996 | Cima et al. |
| 5,495,961 A | 3/1996 | Maestre |
| 5,542,420 A | 8/1996 | Goldman et al. |
| 5,654,011 A | 8/1997 | Jackson et al. |
| 5,672,154 A | 9/1997 | Sillén et al. |
| 5,686,429 A | 11/1997 | Lin et al. |
| 5,692,502 A | 12/1997 | Alpert |
| 5,700,998 A | 12/1997 | Palti |
| 5,704,350 A | 1/1998 | Williams, III |
| 5,719,123 A | 2/1998 | Morley et al. |
| 5,737,539 A * | 4/1998 | Edelson ............ G06F 19/3456 705/3 |
| 5,747,349 A | 5/1998 | van den Engh et al. |
| 5,758,095 A | 5/1998 | Albaum et al. |
| 5,758,096 A | 5/1998 | Barsky et al. |
| 5,765,606 A | 6/1998 | Takemasa et al. |
| 5,770,226 A | 6/1998 | Hughes, Jr. et al. |
| 5,780,014 A | 7/1998 | Eljamal et al. |
| 5,807,579 A | 9/1998 | Vilkov et al. |
| 5,820,876 A | 10/1998 | Hoffmann |
| 5,824,494 A | 10/1998 | Feldberg |
| 5,837,196 A | 11/1998 | Pinkel et al. |
| 5,839,438 A | 11/1998 | Graettinger et al. |
| 5,873,369 A | 2/1999 | Laniado et al. |
| 5,882,931 A | 3/1999 | Petersen |
| 5,907,291 A | 5/1999 | Chen et al. |
| 5,940,801 A | 8/1999 | Brown |
| 5,945,115 A | 8/1999 | Dunn et al. |
| 5,954,640 A | 9/1999 | Szabo |
| 5,955,269 A | 9/1999 | Ghai et al. |
| 5,958,458 A | 9/1999 | Norling et al. |
| 5,968,932 A | 10/1999 | Winokur et al. |
| 5,972,710 A | 10/1999 | Weigl et al. |
| 5,985,214 A | 11/1999 | Stylli et al. |
| 5,993,783 A | 11/1999 | Eljamal et al. |
| 5,995,938 A | 11/1999 | Whaley |
| 6,021,202 A | 2/2000 | Anderson et al. |
| 6,023,916 A | 2/2000 | Bouthiette |
| 6,024,699 A | 2/2000 | Surwit et al. |
| 6,035,230 A | 3/2000 | Kang et al. |
| 6,087,090 A | 7/2000 | Mascarenhas |
| 6,090,545 A | 7/2000 | Wohlstadter et al. |
| 6,117,073 A | 9/2000 | Jones et al. |
| 6,128,534 A | 10/2000 | Park et al. |
| 6,139,494 A | 10/2000 | Cairnes |
| 6,161,095 A | 12/2000 | Brown |
| 6,169,068 B1 | 1/2001 | Levin et al. |
| 6,188,988 B1 | 2/2001 | Barry et al. |
| 6,194,900 B1 | 2/2001 | Freeman et al. |
| 6,221,677 B1 | 4/2001 | Wu et al. |
| 6,227,371 B1 | 5/2001 | Song |
| 6,280,771 B1 | 8/2001 | Monkhouse et al. |
| 6,287,595 B1 | 9/2001 | Loewy et al. |
| 6,295,506 B1 | 9/2001 | Heinonen et al. |
| 6,317,719 B1 | 11/2001 | Schrier et al. |
| 6,335,021 B1 | 1/2002 | Cavazza |
| 6,379,929 B1 | 4/2002 | Burns et al. |
| 6,383,136 B1 | 5/2002 | Jordan |
| 6,397,190 B1 | 5/2002 | Goetz |
| 6,421,650 B1 | 7/2002 | Goetz et al. |
| 6,451,286 B1 | 9/2002 | Modi |
| 6,454,945 B1 | 9/2002 | Weigl et al. |
| 6,468,805 B1 | 10/2002 | Smith |
| 6,482,306 B1 | 11/2002 | Yager et al. |
| 6,497,342 B2 | 12/2002 | Zhang et al. |
| 6,510,430 B1 | 1/2003 | Oberwager et al. |
| 6,529,446 B1 | 3/2003 | de la Huerga |
| 6,541,213 B1 | 4/2003 | Weigl et al. |
| 6,541,478 B1 | 4/2003 | O'Malley et al. |
| 6,565,841 B1 | 5/2003 | Niven et al. |
| 6,565,874 B1 | 5/2003 | Dunn et al. |
| 6,576,267 B2 | 6/2003 | Gelber et al. |
| 6,582,987 B2 | 6/2003 | Jun et al. |
| 6,586,478 B2 | 7/2003 | Ackman et al. |
| 6,589,169 B1 | 7/2003 | Surwit et al. |
| 6,605,454 B2 | 8/2003 | Barenburg et al. |
| 6,616,606 B1 | 9/2003 | Petersen et al. |
| 6,630,155 B1 | 10/2003 | Chandrashekar et al. |
| 6,656,507 B2 | 12/2003 | Petereit et al. |
| 6,671,818 B1 | 12/2003 | Mikurak |
| 6,695,147 B1 | 2/2004 | Yager et al. |
| 6,699,193 B2 | 3/2004 | Crutchfield et al. |
| 6,709,676 B2 | 3/2004 | Cho |
| 6,709,869 B2 | 3/2004 | Mian et al. |
| 6,759,062 B2 | 7/2004 | Gelber et al. |
| 6,764,831 B2 | 7/2004 | Cameron, Sr. et al. |
| 6,773,714 B2 | 8/2004 | Dunn et al. |
| 6,773,721 B1 | 8/2004 | Wong et al. |
| 6,787,164 B2 | 9/2004 | Gelber et al. |
| 6,790,198 B1 | 9/2004 | White et al. |
| 6,793,942 B2 | 9/2004 | Gelber et al. |
| 6,794,196 B2 | 9/2004 | Fonash et al. |
| 6,812,458 B2 | 11/2004 | Gregori et al. |
| 6,818,435 B2 | 11/2004 | Carvalho et al. |
| 6,833,274 B2 | 12/2004 | Lawrence et al. |
| 6,838,076 B2 | 1/2005 | Patton et al. |
| 6,841,544 B2 | 1/2005 | Gelber et al. |
| 6,849,396 B2 | 2/2005 | Schneider |
| 6,852,206 B2 | 2/2005 | Pawliszyn et al. |
| 6,878,755 B2 | 4/2005 | Singh et al. |
| 6,881,425 B2 | 4/2005 | Pushpangadan et al. |
| 6,888,095 B2 | 5/2005 | Khan |
| 6,921,527 B2 | 7/2005 | Platz et al. |
| 6,946,144 B1 | 9/2005 | Jordan |
| 6,951,545 B2 | 10/2005 | Smith et al. |
| 6,955,873 B1 | 10/2005 | Blum |
| 6,958,216 B2 | 10/2005 | Kelley et al. |
| 6,962,720 B2 | 11/2005 | Haridas et al. |
| 6,979,463 B2 | 12/2005 | Kou |
| 6,979,471 B1 | 12/2005 | Khanuja et al. |
| 6,979,679 B2 | 12/2005 | Marcum |
| 6,980,958 B1 | 12/2005 | Surwit et al. |
| 7,005,447 B2 | 2/2006 | Ahotupa et al. |
| 7,016,752 B1 | 3/2006 | Ruben et al. |
| 7,022,288 B1 | 4/2006 | Boss |

(56) References Cited

U.S. PATENT DOCUMENTS

| | | |
|---|---|---|
| 7,029,441 B2 | 4/2006 | Dodds |
| 7,030,989 B2 | 4/2006 | Yager |
| 7,041,317 B2 | 5/2006 | Sekiya et al. |
| 7,041,670 B2 | 5/2006 | Boojamra et al. |
| 7,041,840 B2 | 5/2006 | Gandhi |
| 7,045,145 B1 | 5/2006 | Chien |
| 7,045,159 B1 | 5/2006 | Ilic et al. |
| 7,046,357 B2 | 5/2006 | Weinberger et al. |
| 7,048,945 B2 | 5/2006 | Percel et al. |
| 7,049,312 B1 | 5/2006 | Rafferty et al. |
| 7,049,433 B2 | 5/2006 | Fan et al. |
| 7,053,107 B2 | 5/2006 | Borchardt et al. |
| 7,056,951 B2 | 6/2006 | Spireas |
| 7,074,311 B1 | 7/2006 | Cunningham |
| 7,074,583 B2 | 7/2006 | Yoshizato et al. |
| 7,112,444 B2 | 9/2006 | Beebe et al. |
| 7,135,616 B2 | 11/2006 | Heard et al. |
| 7,136,820 B1 | 11/2006 | Petrus |
| 7,151,982 B2 | 12/2006 | Liff et al. |
| 7,169,432 B2 | 1/2007 | Tanaka et al. |
| 7,172,897 B2 | 2/2007 | Blackburn et al. |
| 7,193,128 B2 | 3/2007 | Copenhaver et al. |
| 7,197,492 B2 | 3/2007 | Sullivan |
| 7,206,605 B2 | 4/2007 | Hattori |
| 7,215,887 B2 | 5/2007 | Ternullo et al. |
| 7,216,343 B2 | 5/2007 | Das et al. |
| 7,218,900 B2 | 5/2007 | Suzuki |
| 7,227,956 B1 | 6/2007 | Onishi |
| 7,236,595 B1 | 6/2007 | Bean et al. |
| 7,245,894 B2 | 7/2007 | Sekiguchi et al. |
| RE39,785 E | 8/2007 | Fuse |
| 7,254,160 B2 | 8/2007 | Kawamoto et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,280,975 B1 | 10/2007 | Donner |
| 7,295,889 B2 | 11/2007 | Lahteenmaki |
| 7,312,243 B1 | 12/2007 | Pravda |
| 7,351,739 B2 | 4/2008 | Ho et al. |
| 7,376,585 B2 | 5/2008 | Haller |
| 7,379,167 B2 | 5/2008 | Mawhirt et al. |
| 7,418,399 B2 | 8/2008 | Schaeffer et al. |
| 7,454,880 B1 | 11/2008 | Austin et al. |
| 7,461,006 B2 | 12/2008 | Gogolak |
| 7,483,839 B2 | 1/2009 | Mayaud |
| 7,490,085 B2 | 2/2009 | Walker et al. |
| 7,502,666 B2 | 3/2009 | Siegel et al. |
| 7,635,594 B2 | 12/2009 | Holmes et al. |
| 7,844,609 B2 | 11/2010 | Kenedy et al. |
| 8,135,595 B2 | 3/2012 | Dalton |
| 2001/0003177 A1 | 6/2001 | Schena et al. |
| 2001/0022758 A1 | 9/2001 | Howard |
| 2001/0037220 A1 | 11/2001 | Merry et al. |
| 2002/0004749 A1 | 1/2002 | Froseth et al. |
| 2002/0016719 A1 | 2/2002 | Nemeth et al. |
| 2002/0019784 A1 | 2/2002 | Ritz |
| 2002/0026111 A1 | 2/2002 | Ackerman |
| 2002/0027164 A1 | 3/2002 | Mault et al. |
| 2002/0032580 A1 | 3/2002 | Hopkins |
| 2002/0032582 A1 | 3/2002 | Feeney, Jr. et al. |
| 2002/0032583 A1 | 3/2002 | Joao |
| 2002/0032620 A1 | 3/2002 | Benz et al. |
| 2002/0033753 A1 | 3/2002 | Imbo |
| 2002/0038392 A1 | 3/2002 | De La Huerga |
| 2002/0046948 A1 | 4/2002 | Chow et al. |
| 2002/0047867 A1 | 4/2002 | Mault et al. |
| 2002/0052763 A1 | 5/2002 | Jung Richardson |
| 2002/0055856 A1 | 5/2002 | Adams |
| 2002/0059030 A1 | 5/2002 | Otworth et al. |
| 2002/0065682 A1 | 5/2002 | Goldenberg |
| 2002/0070226 A1 | 6/2002 | Liff et al. |
| 2002/0077850 A1 | 6/2002 | McMenimen et al. |
| 2002/0091991 A1 | 7/2002 | Castro |
| 2002/0095238 A1 | 7/2002 | Ahlin et al. |
| 2002/0100762 A1 | 8/2002 | Liff et al. |
| 2002/0106429 A1 | 8/2002 | Mudar et al. |
| 2002/0128259 A1 | 9/2002 | Ghazzi et al. |
| 2002/0143434 A1 | 10/2002 | Greeven et al. |
| 2002/0147317 A1 | 10/2002 | Bentsen et al. |
| 2002/0147917 A1 | 10/2002 | Brickell |
| 2002/0156651 A1 | 10/2002 | Florio et al. |
| 2002/0156683 A1 | 10/2002 | Stoutenburg et al. |
| 2002/0173875 A1 | 11/2002 | Wallace et al. |
| 2002/0177763 A1 | 11/2002 | Burns et al. |
| 2002/0192310 A1 | 12/2002 | Bland et al. |
| 2002/0194226 A1 | 12/2002 | Sheth et al. |
| 2002/0194502 A1 | 12/2002 | Sheth et al. |
| 2002/0196141 A1 | 12/2002 | Boone et al. |
| 2003/0005445 A1 | 1/2003 | Schein et al. |
| 2003/0010791 A1 | 1/2003 | Gentiluomo et al. |
| 2003/0019165 A1 | 1/2003 | Gallant et al. |
| 2003/0028399 A1 | 2/2003 | Davis et al. |
| 2003/0032069 A1 | 2/2003 | Muraca |
| 2003/0032868 A1 | 2/2003 | Graskov et al. |
| 2003/0036683 A1 | 2/2003 | Kehr et al. |
| 2003/0055531 A1 | 3/2003 | Liff et al. |
| 2003/0061123 A1 | 3/2003 | McMenimen et al. |
| 2003/0065537 A1 | 4/2003 | Evans |
| 2003/0069757 A1 | 4/2003 | Greenberg |
| 2003/0072770 A1 | 4/2003 | McAnalley et al. |
| 2003/0073931 A1 | 4/2003 | Boecker et al. |
| 2003/0074218 A1 | 4/2003 | Liff et al. |
| 2003/0083685 A1 | 5/2003 | Freeman et al. |
| 2003/0086338 A1 | 5/2003 | Sastry et al. |
| 2003/0088333 A1 | 5/2003 | Liff et al. |
| 2003/0092039 A1 | 5/2003 | Olson-Munoz et al. |
| 2003/0099158 A1 | 5/2003 | De la Huerga |
| 2003/0105552 A1 | 6/2003 | Lunak et al. |
| 2003/0114475 A1 | 6/2003 | Fox et al. |
| 2003/0121929 A1 | 7/2003 | Liff et al. |
| 2003/0125837 A1 | 7/2003 | Walace et al. |
| 2003/0135388 A1 | 7/2003 | Martucci et al. |
| 2003/0137067 A1 | 7/2003 | Cooper et al. |
| 2003/0139655 A1 | 7/2003 | Dodds |
| 2003/0156724 A1 | 8/2003 | Mariano et al. |
| 2003/0158756 A1 | 8/2003 | Abramson |
| 2003/0163353 A1 | 8/2003 | Luce et al. |
| 2003/0171950 A1 | 9/2003 | Kilgannon et al. |
| 2003/0186001 A1 | 10/2003 | Khan |
| 2003/0189058 A1 | 10/2003 | Liff et al. |
| 2003/0191670 A1 | 10/2003 | Hatcher et al. |
| 2003/0193185 A1 | 10/2003 | Valley et al. |
| 2003/0194350 A1 | 10/2003 | Stamatelos et al. |
| 2003/0204412 A1 | 10/2003 | Brier |
| 2003/0207270 A1 | 11/2003 | Kung et al. |
| 2003/0214129 A1 | 11/2003 | Adler |
| 2003/0216831 A1 | 11/2003 | Hart et al. |
| 2003/0219812 A1 | 11/2003 | Quay et al. |
| 2003/0220848 A1 | 11/2003 | Behrendt |
| 2003/0229455 A1 | 12/2003 | Bevilacqua et al. |
| 2003/0233124 A1 | 12/2003 | Hara et al. |
| 2003/0233250 A1 | 12/2003 | Joffe et al. |
| 2003/0233257 A1 | 12/2003 | Matian et al. |
| 2003/0236683 A1 | 12/2003 | Henderson et al. |
| 2004/0001874 A1 | 1/2004 | Davidson et al. |
| 2004/0026447 A1 | 2/2004 | Badin et al. |
| 2004/0032330 A1 | 2/2004 | Hoffman |
| 2004/0033553 A1 | 2/2004 | Littarru et al. |
| 2004/0039599 A1 | 2/2004 | Fralic |
| 2004/0053290 A1 | 3/2004 | Terbrueggen et al. |
| 2004/0064342 A1 | 4/2004 | Browne et al. |
| 2004/0075272 A1 | 4/2004 | Kaufman |
| 2004/0078220 A1 | 4/2004 | Jackson |
| 2004/0078236 A1 | 4/2004 | Stoodley et al. |
| 2004/0081023 A1 | 4/2004 | Ho |
| 2004/0084895 A1 | 5/2004 | Blum |
| 2004/0086872 A1 | 5/2004 | Childers et al. |
| 2004/0088187 A1 | 5/2004 | Chudy et al. |
| 2004/0107022 A1 | 6/2004 | Gomez |
| 2004/0111298 A1 | 6/2004 | Schoenberg |
| 2004/0116780 A1 | 6/2004 | Brown |
| 2004/0121767 A1 | 6/2004 | Simpson et al. |

(56) References Cited

U.S. PATENT DOCUMENTS

| | | |
|---|---|---|
| 2004/0122707 A1 | 6/2004 | Sabol et al. |
| 2004/0122790 A1 | 6/2004 | Walker et al. |
| 2004/0133705 A1 | 7/2004 | Broussard et al. |
| 2004/0138921 A1 | 7/2004 | Broussard et al. |
| 2004/0138926 A1 | 7/2004 | Ishikawa et al. |
| 2004/0143403 A1 | 7/2004 | Brandon et al. |
| 2004/0146592 A1 | 7/2004 | Garrity et al. |
| 2004/0151629 A1 | 8/2004 | Pease et al. |
| 2004/0154688 A1 | 8/2004 | Geltser et al. |
| 2004/0158507 A1 | 8/2004 | Meek, Jr. et al. |
| 2004/0176984 A1 | 9/2004 | White et al. |
| 2004/0188523 A1 | 9/2004 | Lunak et al. |
| 2004/0188524 A1 | 9/2004 | Lunak et al. |
| 2004/0193316 A1 | 9/2004 | Lunak et al. |
| 2004/0210341 A1 | 10/2004 | Wallace et al. |
| 2004/0215486 A1 | 10/2004 | Braverman |
| 2004/0220498 A1 | 11/2004 | Li et al. |
| 2004/0221855 A1 | 11/2004 | Ashton |
| 2004/0224916 A1 | 11/2004 | Dahl et al. |
| 2004/0225203 A1 | 11/2004 | Jemison et al. |
| 2004/0243437 A1 | 12/2004 | Grace et al. |
| 2004/0243441 A1 | 12/2004 | Bocionek et al. |
| 2005/0010416 A1 | 1/2005 | Anderson et al. |
| 2005/0013863 A1 | 1/2005 | Lim et al. |
| 2005/0014134 A1 | 1/2005 | West et al. |
| 2005/0021413 A1* | 1/2005 | Berry ................ A61F 15/001 206/459.1 |
| 2005/0033606 A1 | 2/2005 | Miller |
| 2005/0038558 A1 | 2/2005 | Keene |
| 2005/0038674 A1 | 2/2005 | Braig et al. |
| 2005/0053650 A1 | 3/2005 | Chalmers |
| 2005/0060188 A1 | 3/2005 | Valley |
| 2005/0062238 A1 | 3/2005 | Broadfield et al. |
| 2005/0065645 A1 | 3/2005 | Liff et al. |
| 2005/0070607 A1 | 3/2005 | Andrus et al. |
| 2005/0080651 A1 | 4/2005 | Morrison et al. |
| 2005/0101841 A9 | 5/2005 | Kaylor et al. |
| 2005/0102159 A1 | 5/2005 | Mondshine |
| 2005/0110268 A1 | 5/2005 | Schone |
| 2005/0113649 A1 | 5/2005 | Bergantino |
| 2005/0118202 A1 | 6/2005 | Yamashita et al. |
| 2005/0118241 A1 | 6/2005 | Landschaft |
| 2005/0147667 A1 | 7/2005 | Rines |
| 2005/0149354 A1 | 7/2005 | Cyr et al. |
| 2005/0158401 A1 | 7/2005 | Morris |
| 2005/0180962 A1 | 8/2005 | Raz et al. |
| 2005/0191716 A1 | 9/2005 | Surwit et al. |
| 2005/0192487 A1 | 9/2005 | Cosentino et al. |
| 2005/0211768 A1 | 9/2005 | Stillman |
| 2005/0216313 A1 | 9/2005 | Claud et al. |
| 2005/0216390 A1 | 9/2005 | Snider et al. |
| 2005/0218152 A1 | 10/2005 | Simon |
| 2005/0228245 A1 | 10/2005 | Quy |
| 2005/0240085 A1 | 10/2005 | Knoell et al. |
| 2005/0240305 A1 | 10/2005 | Bogash et al. |
| 2005/0260679 A1 | 11/2005 | Kellerman et al. |
| 2005/0261255 A1 | 11/2005 | Serhan et al. |
| 2005/0267356 A1* | 12/2005 | Ramasubramanian ... A61J 1/03 600/411 |
| 2005/0271596 A1 | 12/2005 | Friedman et al. |
| 2005/0285746 A1 | 12/2005 | Sengupta et al. |
| 2006/0010009 A1 | 1/2006 | Fangman |
| 2006/0015016 A1 | 1/2006 | Thornton |
| 2006/0028727 A1 | 2/2006 | Moon et al. |
| 2006/0047538 A1 | 3/2006 | Condurso et al. |
| 2006/0064250 A1 | 3/2006 | Goldstein |
| 2006/0073099 A1 | 4/2006 | Frincke et al. |
| 2006/0073484 A1 | 4/2006 | Mathies et al. |
| 2006/0089542 A1 | 4/2006 | Sands |
| 2006/0090765 A1* | 5/2006 | Surina .................... G06F 19/00 128/898 |
| 2006/0097516 A1 | 5/2006 | Kozlowski et al. |
| 2006/0099310 A1 | 5/2006 | Koekkoek |
| 2006/0111944 A1 | 5/2006 | Sirmans, Jr. et al. |
| 2006/0129324 A1 | 6/2006 | Rabinoff et al. |
| 2006/0177637 A1 | 8/2006 | Kimura |
| 2006/0240150 A1* | 10/2006 | Delaney ............... A23K 20/174 426/74 |
| 2006/0254580 A1 | 11/2006 | Chalmers et al. |
| 2006/0260679 A1 | 11/2006 | Aratani et al. |
| 2006/0264780 A1 | 11/2006 | Holmes et al. |
| 2006/0280307 A1 | 12/2006 | Ikushima et al. |
| 2006/0281770 A1 | 12/2006 | Kase et al. |
| 2007/0065506 A1 | 3/2007 | Kelly et al. |
| 2007/0067186 A1 | 3/2007 | Brenner et al. |
| 2007/0068959 A1 | 3/2007 | D'Silva |
| 2007/0087048 A1 | 4/2007 | Abrams et al. |
| 2007/0093448 A1 | 4/2007 | Westermann et al. |
| 2007/0118054 A1* | 5/2007 | Pinhas ................. A61B 5/1102 600/587 |
| 2007/0136092 A1 | 6/2007 | Jung et al. |
| 2007/0161076 A1 | 7/2007 | Halden |
| 2007/0192134 A1 | 8/2007 | Littenberg et al. |
| 2008/0097784 A1 | 4/2008 | Miller et al. |
| 2008/0100279 A1 | 5/2008 | Mohapatra et al. |
| 2008/0208027 A1 | 8/2008 | Heaton |
| 2008/0299013 A1* | 12/2008 | Trieu ..................... B01L 9/527 422/400 |
| 2009/0198176 A1* | 8/2009 | Chavez ................... A61M 5/20 604/67 |
| 2010/0081144 A1 | 4/2010 | Holmes et al. |

FOREIGN PATENT DOCUMENTS

| | | |
|---|---|---|
| WO | WO 99/45354 | 9/1999 |
| WO | WO 99/45354 A2 | 9/1999 |
| WO | WO 99/45354 A3 | 9/1999 |
| WO | WO 00/60362 | 10/2000 |
| WO | WO 00/60362 A1 | 10/2000 |
| WO | WO 01/79529 A1 | 10/2001 |
| WO | WO 03/084395 A1 | 10/2003 |
| WO | WO 2004/061085 A3 | 7/2004 |
| WO | WO 2004/082359 A2 | 9/2004 |
| WO | WO 2005/018632 A1 | 3/2005 |
| WO | WO 2005/041105 A1 | 5/2005 |
| WO | WO 2005/062849 A2 | 7/2005 |
| WO | WO 2006/032044 A3 | 3/2006 |
| WO | WO 2007/061838 A2 | 5/2007 |

OTHER PUBLICATIONS

U.S. Appl. No. 11/904,016, Jung et al.
U.S. Appl. No. 11/906,112, Jung et al.
U.S. Appl. No. 11/355,517, Jung et al.
U.S. Appl. No. 11/339,316, Jung et al.
U.S. Appl. No. 11/314,949, Jung et al.
U.S. Appl. No. 11/314,764, Jung et al.
U.S. Appl. No. 11/291,532, Jung et al.
U.S. Appl. No. 11/285,753, Jung et al.
U.S. Appl. No. 11/285,500, Jung et al.
U.S. Appl. No. 11/283,548, Jung et al.
PCT International Search Report; International Appl. No. PCT/US 06/44664; dated Apr. 14, 2008; pp. 1-3.
PCT International Search Report; International App. No. PCT/ US 06/44269; dated Sep. 18, 2007; pp. 1-2.
U.S. Appl. No. 11/900,660, Jung et al.
U.S. Appl. No. 11/900,649, Jung et al.
U.S. Appl. No. 11/900,637, Jung et al.
Brüssow, Harald; "Phage Therapy: the *Escherichia coli* experience"; Microbiology; 2005; pp. 2133-2140; vol. 151.
Merril, Carl R.; Biswas, Biswajit; Carlton, Richard; Jensen, Nicole C.; Creed, G. Joseph; Zullo, Steve; Adhya, Sankar; "Long-circulating bacteriophage as antibacterial agents"; Proc. Natl. Acad. Sci.; Apr. 1996; pp. 3188-3192; vol. 93.
PCT International Search Report; International App. No. PCT/ US2005/033347; dated Aug. 23, 2006; 4 pages.
PCT International Search Report; International App. No. PCT/US03/ 41466; dated Aug. 26, 2004; 2 pages.
PCT International Search Report; International App. No. PCT/US01/ 09745; dated Aug. 2, 2001; 1 page.

(56) References Cited

OTHER PUBLICATIONS

PCT International Search Report; International App. No. PCT/IL99/00122; dated Aug. 30, 1999; 2 pages.
Woolley, AT et al.; "Functional integration of PCR amplification and capillary electrophoresis in a microfabricated DNA analysis device"; Anal Chem; Bearing a date of Dec. 1, 1996; pp. 4081-4086 (p. 1); vol. 68, No. 23; PubMed; located at: http://www.ncbi.nlm.nih.gov; printed on Aug. 2, 2007.
"A1C At-Home Test Kit-Introductory Offer (1 per customer, first time buyers Only)"; Amazon.com; Bearing dates of 1996-2006; pp. 1-4; Amazon.com, Inc.; located at http://www.amazon.com/gp/product/B0006JMPRG/ref=sr_11_1/103-2429377-9250203?ie=UTF8; printed on Jul. 10, 2006.
Abrams, Bernard; "Standing Rx packaging on its head"; Packagingdigest.com; Bearing a date of Jun. 2005; pp. 1-3; located at http://www.packagingdigest.com/articles/200506/38.php; printed on Jun. 21, 2006.
Actis-Goretta, Lucas; Ottaviani, Javier I.; Fraga, Cesar G.; "Inhibition of Angiotensin Converting Enzyme Activity by Flavanol-Rich Foods"; Journal of Agricultural and Food Chemistry; Bearing a date of 2006; pp. 229-234; vol. 54; American Chemical Society.
Aihara, K; Kajimoto, O; Hirata, H; Takahashi, R; Nakamura, Y; "Effect of powdered fermented milk with Lactobacillus helveticus on subjects with high-normal blood pressure or mild hypertension"; J. Am. Coll. Nutr.; Bearing a date of Aug. 2005; pp. 257-265 (pp. 1-2); vol. 24, No. 4; PubMed; located at: http://www.ncbi.nlm.nih.gov/sites/entrez?db=pubmed&list_uids=16093403&cmd=Retrieve&indexed=google; printed on Jun. 25, 2007.
"Anemia Tests"; Home Health Testing; Bearing dates of Dec. 1, 2005 and 2000; pp. 1-3; AbDiagnostics, Inc.; located at: http://www.homehealthtesting.com/anemia-tests.htm; printed on Jul. 24, 2006.
"Antioxidant Tests"; Home Health Testing; Bearing dates of Dec. 1, 2005 and 2000; pp. 1-2; AbDiagnostics, Inc.; located at: http://www.homehealthtesting.com/antioxidant-tests.htm; printed on Jul. 24, 2006.
Appleton, David; Lockwood, Brian; "Building Bones with Nutraceuticals"; The Pharmaceutical Journal; Bearing a date of Jul. 15, 2006; pp. 78-83; vol. 277; located at: http://www.pjonline.com/pdf/articles/pj_20060715_bones.pdf; printed on Aug. 22, 2006.
Bassaganya-Riera, J.; Hontecillas, R.; Wannemuehler, M.; "Nutrition impact of conjugated linoleic acid: A model functional food ingredient"; In Vitro Cellular and Development Biology-Plant; May 2002; pp. 241-246 (pp. 1-2); vol. 38, No. 3; Online ISSN 1475-2689; Springer; located at: http://www.ingentaconnect.com/content/klu/ivp/2002/00000038/00000003/02002295?crawler=true; printed on Jun. 25, 2007.
"Blood Testing and Sampling Kits"; BloodBook.com; Bearing dates of Nov. 19, 2005 and 2000-2005; pp. 1-2; located at: http://www.bloodbook.com/test-kits.html; printed on Jul. 10, 2006.
Blum, K; Meshkin, B; Downs, BW; "DNA based customized Nutraceutical 'gene therapy' utilizing a genoscore: a hypothesized paradigm shift of a novel approach to the diagnosis, stratification, prognosis and treatment of inflammatory processes in the human"; Med. Hypotheses; Bearing dates of 2006 and Jan. 5, 2006; pp. 1008-1018 (pp. 1-2); vol. 66, No. 5; PubMed; located at: http://www.ncbi.nlm.nih.gov/sites/entrez?db=pubmed; printed on Jun. 11, 2007.
"Body Balance: AntiOxidant Check"; Health HomeTest.com; Bearing dates of 2003-2005; pp. 1-4; B Scientific, Inc.; located at: http://www.healthhometest.com/product_info.php?products_id=39; printed on Jul. 24, 2006.
"Body Balance: FemaleCheck / Estradiol, Progesterone & Testosterone"; Health HomeTest.com; Bearing dates of 2003-2005; pp. 1-5; B Scientific, Inc.; located at: http://www.healthhometest.com/product_info.php?products_id=36; printed on Jul. 24, 2006.
"Body Balance: MaleCheck / Testosterone & DHEA"; Health HomeTest.com; Bearing dates of 2003-2005; pp. 1-4; B Scientific, Inc.; located at: http://www.healthhometest.com/product_info.php?manufacturers_id=10&products_id=40; printed on Jul. 24, 2006.
"Body Balance: Mineral Check"; Health HomeTest.com; Bearing dates of 2003-2005; pp. 1-8; B Scientific, Inc.; located at: http://www.healthhometest.com/product_info.php?products_id=35; printed on Jul. 24, 2006.
"Body Balance: Performance Check"; Health HomeTest.com; Bearing dates of 2003-2005; pp. 1-7; B Scientific, Inc.; located at: http://www.healthhometest.com/product_info.php?products_id=82; printed on Jul. 24, 2006.
"Body Balance: Sleep Check / Melatonin"; Health HomeTest.com; Bearing dates of 2003-2005; pp. 1-4; B Scientific, Inc.; located at: http://www.healthhometest.com/product_info.php?products_id=46; printed on Jul. 24, 2006.
"Body Balance: Stress Check / DHEA & Cortisol"; Health HomeTest.com; Bearing dates of 2003-2005; pp. 1-6; B Scientific, Inc.; located at: http://www.healthhometest.com/product_info.php?products_id=43; printed on Jul. 24, 2006.
"Body Building Hormone Tests"; Home Health Testing; Bearing dates of Dec. 1, 2005 and 2000; pp. 1-3; AbDiagnostics, Inc.; located at: http://www.homehealthtesting.com/performance-hormone-tests.htm; printed on Jul. 24, 2006.
Bridges, Andrew; "HIV/AIDS patients get $1^{st}$ once-daily pill"; Associated Press; Bearing a date of 2006; pp. 1-3; Yahoo! Inc.; located at http://news.yahoo.com/s/ap/20060712/ap_on_he_me/hiv_one_pill; printed on Jul. 12, 2006.
"Browse by: Product Category"; Hach.com; Bearing a date of 2006; pp. 1-2; Hach Company; located at: http://www.hach.com/hc/browse.exploded.product.category/PREVIOUS_BREADCRUMB_ID=/SESSIONID|BzFOVFUzTnpZMElURTBOQlpuZFdWemRFMUNTZz09QTFOVUlURQ==|; printed on Jul. 14, 2006.
Chen, ZP; Schell, JB; Ho, CT; Chen, KY; "Green tea epigallocatechin gallate shows a pronounced growth inhibitory effect on cancerous cells but not on their normal counterparts"; Cancer Lett.; Jul. 17, 1998; pp. 173-179 (pp. 1-2); vol. 129, No. 2; PubMed; located at: http://www.ncbi.nlm.nih.gov/sites/entrez?db=pubmed; printed on Jun. 22, 2007.
Chen, Haibin; Sholl, David S.; "Predictions of Selectivity and Flux for $CH_4/H_2$ Separations Using Single Walled Carbon Nanotubes as Membranes"; Journal of Membrane Science; Bearing dates of 2005 and 2006; pp. 152-160; vol. 269; Elsevier B.V.; located at: www.sciencedirect.com and www.elsevier.com/locate/memsci.
Chiu, KM; Keller, ET; Crenshaw, TD; Gravenstein, S.; "Carnitine and dehydroepiandrosterone sulfate induce protein synthesis in porcine primary osteoblast-like cells"; Calcified Tissue International; Bearing a date of Jun. 1999; pp. 527-533 (pp. 1-2); vol. 64, Issue 6; PubMed; located at: http://www.ncbi.nlm.nih.gov/entrez/query.fcgi?cmd=Retrieve&db=PubMed&list_uids=10341026&dopt=Abstract; printed on Aug. 22, 2006.
"Clearrx System: Body"; pp. 1-4; located at http://www.index2005.dk/Members/tenamikesy/bodyObject; printed on Jun. 21, 2006.
"Clinical Laboratory: Beckman Coulter clinical systems help to simplify and automate laboratory processes"; Beckman Coulter.com; Bearing dates of 1998-2006; p. 1; Beckman Coulter, Inc.; located at: http://www.beckmancoulter.com/products/pr_clinical_lab.asp; printed on Jul. 14, 2006.
Colucci, S; Mori, G; Vaira, S; Brunetti, G; Greco, G; Mancini, L; Simone, GM; Sardelli, F; Koverech, A; Zallone, A; Grano, M; "L-carnitine and isovaleryl L-carnitine fumarate positively affect human osteoblast proliferation and differentiation in vitro"; Calcified Tissue International; Bearing a date of Jun. 2005; pp. 458-465 (pp. 1-2); vol. 76, Issue 6; PubMed; located at: http://www.ncbi.nlm.nih.gov/entrez/query.fcgi?cmd=Retrieve&db=PubMed&list_uids=15906015&dopt=Abstract; printed on Aug. 22, 2006.
"Confidential Home DNA Infidelity Testing, Infidelity Test Kit"; Gtldna.com; Bearing dates of Jul. 10, 2006 and 2002-2005; pp. 1-3; The Genetic Testing Laboratories, Inc.; located at: http://www.gtldna.com/infidelity.html; printed on Jul. 10, 2006.
Davidow, Julie; "Surge in home diagnostic kits provides doctor in a box"; Seattlepi.com; Bearing dates of Mar. 29, 2006 and 1996-2006; pp. 1-4; Seattle Post-Intelligencer; located at: http://seattlepi.nwsource.com/health/264716_hometesting29.html; printed on Jul. 10, 2006.

(56) References Cited

OTHER PUBLICATIONS

Demello, Andrew J.; "Microfluidics: DNA Amplification Moves on"; Nature; Bearing dates of Mar. 6, 2003 and 2003; pp. 28-29; vol. 422; Nature Publishing Group; located at: www.nature.com/nature.
"Direct to Consumer Blood Test Index"; PreventiveLabs.com; Bearing a date of 2004; pp. 1-6; Preventive Services, LLC; located at: http://www.preventivelabs.com/lab_test/blood_test.cfm; printed on Jul. 10, 2006.
"DR / 2400 Portable Spectrophotometer, 115 Vac"; Hach.com; Bearing a date of 2006; p. 1; Hach Company; located at: http://www.hach.com/hc/search.product.details.invoker/PackagingCode=5940000/NewLinkLabel=DR%26frasl%3B2400+Portable+Spectrophotometer%2C+115+Vac/PREVIOUS_BREADCRUMB_ID=HC_SEARCH_KEYWORD/SESSIONID|BzFOVFUzTnpFMk56WXINUIpuZFdWemRFTk9Vdz09QTFsTklURO==|; printed on Jul. 14, 2006.
"DR 5000 UV-VIS Spectrophotometer (115 Vac)"; Hach.com; Bearing a date of 2006; p. 1; Hach Company; located at: http://www.hach.com/hc/search.product.details.invoker/PackagingCode=DR5000-01/NewLinkLabel=DR+5000+UV-Vis+Spectrophotometer%2C+115+Vac/PREVIOUS_BREADCRUMB_ID=HC_SEARCH_BROWSE_PRODUCTSpectrophotometersColorimeters/SESSIONID|B3hOVFUxTnpjeE5qYzJNakVtWjNWbGMzUkRUZz09QWxOWIRURQ==|; printed on Jul. 14, 2006.
"Drugstore.com—online pharmacy & drugstore, prescriptions filled"; drugstore.com; Bearing dates of 1999-2006; pp. 1 (Sheets 1-3), pp. 2 (Sheets 1-4), pp. 3 (Sheets 1-2) (pp. total 1-9); drugstore.com, inc.; located at: http://www.drugstore.com/search/search.asp?searchtype=1&trx=28198&trxp1=60&ipp=20&srchtree=1&search=home+test+kit&Go.x=17&Go.y=16; printed on Jul. 10, 2006.
Duffy, SJ; Vita, JA; "Effects of phenolics on vascular endothelial function"; Current Opinion in Lipidology; Bearing a date of Feb. 2003; pp. 21-27 (p. 1); vol. 14, Issue 1; PubMed; located at: http://www.ncbi.nlm.nih.gov/entrez/query.fcgi?cmd=Retrieve&db=PubMed&list_uids=12544657&dopt=Abstract; printed on Aug. 22, 2006.
Dumont, Yannick; D'Amours, Martin; Lebel, Marcel; Larivière, Richard; "Original Article: Supplementation with a low dose of L-arginine reduces blood pressure and endothelin-1 production in hypertensive uraemic rats"; Nephrol Dial Transplant; Bearing a date of 2001; pp. 746-754; vol. 16; European Renal Association—European Dialysis and Transplant Association.
Eskin, N.A. Michael; Dictionary of Nutraceuticals and Functional Foods (Functional Foods and Nutraceuticals); Bearing a date of Dec. 19, 2005; 520 pages; ISBN No. 0849315727; CRC Press (not provided).
"Family Age Groups"; testsymptomsathome.com; pp. 1-4; located at: http://www.testsymptomsathome.com/family_age_groups.asp; printed on Jul. 10, 2006.
Fan, Chunhai; Plaxco, Kevin W.; Heeger, Alan J.; "Electrochemical interrogation of conformational changes as a reagentless method for the sequence-specific detection of DNA"; PNAS; Bearing a date of Aug. 5, 2003; pp. 9134-9137; vol. 100, No. 16; located at: www.pnas.org/cgi/doi/10.1073/pnas.1633515100.
"FDA OKs 3-Drug Combo Pill to Treat HIV"; Bearing a date of Jun. 30, 2006; pp. 1-2; FoxNews.com; located at http://www.foxnews.com/wires/2006Jun30/0,4670,AIDSRelief,00.html; printed on Jun. 30, 2006.
Felkey, Bill G.; Berger, Bruce A.; Krueger, Kem P.; "The Pharmacist's Role in Treatment Adherence—Part 5: The Impact of Pharmacy-Specific Technology"; U.S. Pharmacist; Bearing dates of 2005, 2000-2005; and a posted date of Aug. 18, 2005; pp. 36-39 (pp. 1-6); vol. 30:08; Jobson Publishing, L.L.C.; located at: http://www.uspharmacist.com/index.asp?show=article&page=8_1547.htm; printed on Nov. 13, 2005.
"Female Hormone Tests"; Home Health Testing; Bearing dates of Dec. 1, 2005 and 2000; pp. 1-3; AbDiagnostics, Inc.; located at: http://www.homehealthtesting.com/female-hormone-tests.htm; printed on Jul. 24, 2006.
Fitzgerald, Katherine A.; O'Neill, Luke A.J.; Gearing, Andy J.H.; Callard, Robin E.; "The Cytokine Factsbook"; Bearing a date of Sep. 2001; 515 pages; 2nd Edition; ISBN No. 0121551423; Academic Press; San Francisco, CA (not provided).
Gao, Huajian; Kong, Yong; "Simulation of DNA-Nanotube Interactions"; Annual Review of Materials Research.; Bearing a date of 2004; pp. 123-150 (33 total pages); vol. 34; Annual Reviews.
Gennaro, Alfonso R. (Ed); Remington: The Science and Practice of Pharmacy; Bearing a date of Dec. 15, 2000; 2077 pages; $20^{th}$ Edition; ISBN No. 0683306472; Lippincott Williams and Wilkins; Philadelphia, PA (not provided).
Gosslau, A; Chen, M; Ho, CI-T; Chen, KY; "Translational Therapeutics: A methoxy derivative of resveratrol analogue selectively induced activation of the mitochondrial apoptotic pathway in transformed fibroblasts"; British Journal of Cancer; Bearing dates of 2005 and Jan. 25, 2005; pp. 513-521 (pp. 1-2); vol. 92; Online ISSN: 1532-1827; Cancer Research UK; located at: http://www.nature.com/bjc/journal/v92/n3/abs/6602300a.html; printed on Jun. 22, 2007.
Gruenewald, Tara L.; Seeman, Teresa E.; Ryff, Carol D.; Karlamangla, Arun S.; Singer, Burton H.; "Combinations of biomarkers predictive of later life mortality"; PNAS; Bearing dates of Sep. 19, 2006 and 2006; pp. 14158-14163; vol. 103, No. 38; The National Academy of Sciences of the USA; located at http://www.pnas.org/cgi/doi/10.1073/pnas.0606215103.
"Heart-Help's Handbook . . . Living with CM & CHF (Cardiomyopathy & Congestive Heart Failure)"; Bearing a date of Sep. 23, 2001; pp. 1-5; located at: http://www.heart-help.net/handbook.html; printed on Nov. 13, 2005.
Heller, Daniel A.; Jeng, Esther S.; Yeung, Tsun-Kwan; Martinez, Brittany M.; Moll, Anthonie E.; Gastala, Joseph B.; Strano, Michael S.; "Optical Detection of DNA Conformational Polymorphism on Single-Walled Carbon Nanotubes"; Science; Bearing a date of Jan. 27, 2006; pp. 508-511; vol. 311; located at: www.sciencemag.org.
Hobbs, Charlotte, A.; Sherman, Stephanie, L.; Yi, Ping; Hopkins, Sarah E.; Torfs, Claudine P.; Hine, R. Jean; Pogribna, Marta; Rozen, Rima; James, S. Jill; "Polymorphisms in Genes Involved in Folate Metabolism as Maternal Risk Factors for Down Syndrome"; Am. J. Hum. Genet.; Bearing a date of 2000; pp. 623-630; vol. 67; The American Society of Human Genetics.
Hodgson, JM; Watts, GF; Playford, DA; Burke, V; Croft, KD; "Original Communication—Coenzyme $Q_{10}$ improves blood pressure and glycaemic control: a controlled trial in subjects with type 2 diabetes"; European Journal of Clinical Nutrition; Bearing a date of 2002; pp. 1137-1142; vol. 56; Nature Publishing Group; located at: www.nature.com/ejcn.
Holt, Jason K.; Park, Hyung Gyu; Wang, Yinmin; Stadermann, Michael; Artyukhin, Alexander B.; Grigoropoulos, Costas P.; Noy, Aleksandr; Bakajin, Olgica; "Fast Mass Transport Through Sub-2-Nanometer Carbon Nanotubes"; Science; Bearing a date of May 19, 2006; pp. 1034-1037; vol. 312; located at: www.sciencemag.org.
"Home Allergy Tests"; Home Health Testing; Bearing dates of Dec. 1, 2005 and 2000; pp. 1-3; AbDiagnostics, Inc.; located at: http://www.homehealthtesting.com/allergy-tests.htm; printed on Jul. 24, 2006.
"Home DNA Maternity Testing, Test Kit, Blood Paternity Testing"; Gtldna.com; Bearing dates of 2002-2005; pp. 2-5; The Genetic Testing Laboratories, Inc.; located at: http://www.gtldna.com/maternitytest.html; printed on Jul. 10, 2006.
"Home DNA Prenatal Paternity, Maternity, Siblingship Test, Twin Zygosity, Kinship, Immigration DNA Testing"; Gtldna.com; Bearing dates of Jul. 10, 2006 and 2002-2005; pp. 1-5; The Genetic Testing Laboratories, Inc.; located at: http://www.gtldna.com/dnatests.html; printed on Jul. 10, 2006.
"Home Test Kits, Blood Groups, Diabetes, Menopause, Prostate, Osteoporosis"; WorldWideShoppingMall.co.uk; pp. 1-2; World Wide Shopping Mall (WWSM); located at: http://www.worldwideshoppingmall.co.uk/Body-Soul/shelves/home . . . ; printed on Jul. 10, 2006.
"Home Test Kits, Hepatitis Test, HIV Test, Blood Type Test"; Quick Medical: Professional and Home Health Products; Bearing a date of 2006; pp. 1-2; located at: http://www.quickmedical.com/monitors/blood_testing/; printed on Jul. 10, 2006.

(56) References Cited

OTHER PUBLICATIONS

"Home Test Kits"; PriceGrabber.com; pp. 1 (Sheets 1-5), pp. 2 (Sheets 1-4), pp. 3 (1-5), pp. 4 (Sheets 1-3) (pp. total 1-17); PriceGrabber.com, Inc.; located at: http://www.pricegrabber.com/search_attrib.php/page_id=1970; printed on Jul. 10, 2006.

"Hormone Tests"; Home Health Testing; Bearing dates of Dec. 1, 2005 and 2000; pp. 1-2; AbDiagnostics, Inc.; located at: http://www.homehealthtesting.com/hormone-tests.htm?gcnd-civ; printed on Jul. 24, 2006.

"Hormone Test Kit-Blood"; The Official Web Site of John R. Lee, MD: Your Information Source for Natural Hormone Balance and Natural HRT; pp. 1-3; Hormones Etc.; located at: http://www.johnleemd.com/store/prod_btest.html; printed on Jul. 10, 2006.

"Instant Anemia Test"; Health HomeTest.com; Bearing dates of 2003-2005; pp. 1-9; B Scientific, Inc.; located at: http://www.healthhometest.com/product_info.php?products_id=81; printed on Jul. 24, 2006.

"Introducing Integrated Instrument + Reagent Analysis: Hach DR 5000™ UV-VIS Spectrophotometer and DR 2800™ Portable Spectrophotometer + new Hach TNTplus™ Vial Reagents"; Hach.com; Bearing a date of 2006; pp. 1-3; Hach Company; located at: http://www.hach.com/photometry; printed on Jul. 14, 2006.

Jain, KK; "Conference Scene: Lab-on-a-Chip and Microarrays: Discovery and Development"; Pharmacogenomics; Bearing a date of 2003; pp. 123-125; vol. 4, No. 2; Ashley Publications Ltd; located at: www.pharmaco-genomics.com.

James, S. Jill; Pogribna, Marta; Pogribny, Igor P.; Melnyk, Stepan; Hine, R. Jean; Gibson, James B.; Yi, Ping; Tafoya, Dixie L.; Swenson, David H.; Wilson, Vincent L.; Gaylor, David W.; "Abnormal folate metabolism and mutation in the methylenetetrahydrofolate reductase gene may be maternal risk factors for Down syndrome"; The American Journal of Clinical Nutrition; Bearing a date of 1999; pp. 495-501; vol. 70; American Society for Clinical Nutrition; located at: www.ajcn.org; printed on Jun. 11, 2007.

Jarvius, Jonas; DNA Tools and Microfluidic Systems for Molecular Analysis; Digital Comprehensive Summaries of Uppsala Dissertations from the Faculty of Medicine 161; Bearing a date of 2006; pp. 1-66; ISBN 91-554-6616-8; Acta Universitatis Upsaliensis Uppsala.

Kanauchi, O; Igarashi, K; Ogata, R; Mitsuyama, K; Andoh, A; "A yeast extract high in bioactive peptides has a blood-pressure lowering effect in hypertensive model"; Curr. Med. Chem.; Bearing a date of 2005; pp. 3085-3090 (p. 1); vol. 12, No. 26; PubMed; located at: http://www.ncbi.nlm.nih.gov/sites/entrez?db=pubmed; printed on May 17, 2007.

Katan, Martijn B.; "Editorial: Health claims for functional foods"; BMJ; Bearing a date of Jan. 24, 2004; pp. 180-181 (pp. 1-3); vol. 328; BMJ Publishing Group Ltd.; located at: http://www.bmj.com/cgi/content/full/328/7433/180; printed on Jun. 1, 2007.

Keung, WM; "Anti-dipsotropic isoflavones: the potential therapeutic agents for alcohol dependence"; Medicinal Research Reviews; Bearing a date of Nov. 2003; pp. 669-696 (pp. 1-2); vol. 23, Issue 6; PubMed; located at: http://www.ncbi.nlm.nih.gov/entrez/query.fcgi?cmd=Retrieve&db=PubMed&list_uids=12939789&dopt=Abstract; printed on Aug. 22, 2006.

Khosh, Farhang; Khosh, Mehdi; "Natural Approach to Hypertension"; Alternative Medicine Review; Bearing a date of 2001; pp. 590-600; vol. 6, No. 6; Thorne Research, Inc.

Kitajka, Klára; Sinclair, Andrew J.; Weisinger, Richard S.; Weisinger, Harrison S.; Mathai, Michael; Jayasooriya, Anura P.; Halver, John E.; Puskáas, László G.; "Biochemistry: Effects of dietary omega-3 polyunsaturated fatty acids on brain gene expression"; PNAS; Bearing a date of Jul. 27, 2004; pp. 10931-10936; vol. 101, No. 30; The National Academy of Sciences of the USA; located at: www.pnas.org/cgi/doi/10.1073/pnas.0402342101.

Klinge, CM; Blankenship, KA; Risinger, KE; Bhatnagar, S; Noisin, EL; Sumanasekera, WK; Zhao, L; Brey, DM; Keynton, RS; "Resveratrol and estradiol rapidly activate MAPK signaling through estrogen receptors alpha and beta in endothelial cells"; The Journal of Biological Chemistry; Bearing a date of Mar. 4, 2005; pp. 7460-7468 (pp. 1-2); vol. 280, Issue 9; PubMed; located at: http://www.ncbi.nlm.nih.gov/entrez/query.fcgi?cmd=Retrieve&db=PubMed&list_uids=15615701&dopt=Abstract; printed on Aug. 22, 2006.

Li, JX; Xue, B; Chai, Q; Liu, ZX; Zhao, AP; Chen, LB; "Antihypertensive effect of total flavonoid fraction of Astragalus complanatus in hypertensive rats"; The Chinese Journal of Physiology; Bearing a date of Jun. 30, 2005; pp. 101-106 (pp. 1-2); vol. 48, Issue 2; PubMed; located at: http://www.ncbi.nlm.nih.gov/entrez/query.fcgi?cmd=Retrieve&db=PubMed&list_uids=16201455&dopt=Abstract; printed on Aug. 22, 2006.

Lin, RC; Guthrie, S; Xie, CY; Mai, K; Lee, DY; Lumeng, L; Li, TK; "Isoflavonoid compounds extracted from Pueraria lobata suppress alcohol preference in a pharmacogenetic rat model of alcoholism"; Alcoholism, Clinical & Experimental Research; Bearing a date of Jun. 1996; pp. 659-663 (pp. 1-2); vol. 20, Issue 4; PubMed; located at: http://www.ncbi.nlm.nih.gov/entrez/query.fcgi?CMD=Display&DB=pubmed; printed on Aug. 22, 2006.

Lu, Jiebo; Ho, Chi-Tang; Ghai, Geetha; Chen, Kuang Yu; "Differential Effects of Theaflavin Monogallates on Cell Growth, Apoptosis, and Cox-2 Gene Expression in Cancerous versus Normal Cells"; Cancer Research; Bearing a date of Nov. 15, 2000; pp. 6465-6471; vol. 60.

Lu, Jiebo; Ho, Chi-Tang; Ghai, Geetha; Chen, Kuang Yu; "Resveratrol analog, 3,4,5,4,'-tetrahydroxystilbene, differentially induces pro-apoptotic p53/Bax gene expression and inhibits the growth of transformed cells but not their normal counterparts"; Carcinogenesis; Bearing a date of 2001; pp. 321-328; vol. 22, No. 2; Oxford University Press.

Lucock, Mark; "Clinical Review: Science, Medicine, and the future—Is folic acid the ultimate functional food component for disease prevention?" BMJ; Bearing a date of Jan. 24, 2004; pp. 211-214 (pp. 1-9); vol. 328; BMJ Publishing Group Ltd.; located at: http://www.bmj.com/cgi/content/full/328/7433/211; printed on Jun. 22, 2007.

Ma, Jing; Stampfer, Meir J.; Giovannucci, Edward; Artigas, Carmen; Hunter, David J.; Fuchs, Charles; Willett, Walter C.; Selhub, Jacob; Hennekens, Charles H.; Rozen, Rima; "Methylenetetrahydrofolate Reductase Polymorphism, Dietary Interactions, and Risk of Colorectal Cancer"; Cancer Research; Bearing a date of Mar. 15, 1997; pp. 1098-1102; vol. 57.

Machha, A; Mustafa, MR; "Chronic treatment with flavonoids prevents endothelial dysfunction in spontaneously hypertensive rat aorta"; Journal of Cardiovascular Pharmacology; Bearing a date of Jul. 2005; pp. 36-40 (p. 1); vol. 46, Issue 1; PubMed; located at: http://www.ncbi.nlm.nih.gov/entrez/query.fcgi?CMD=Display&DB=pubmed; printed on Aug. 22, 2006.

"Male Hormone Tests"; Home Health Testing; Bearing dates of Dec. 1, 2005 and 2000; pp. 1-2; AbDiagnostics, Inc.; located at: http://www.homehealthtesting.com/male-hormone-tests.htm; printed on Jul. 24, 2006.

Malnick, Stephen; Goland, Sorel; "Folic acid as ultimate in disease prevention Beware of vitamin B12 deficiency"; BMJ; Bearing a date of Mar. 27, 2004; pp. 1-2; vol. 328, No. 769; BMJ Publishing Group Ltd.; located at: http://www.bmj.com/cgi/content/full/328/7442/769; printed on Jun. 25, 2007.

Mangels, Reed; "Vitamin B12 in the Vegan Diet"; The Vegetarian Resource Group: Nutrition; Bearing dates of 1996-2003 and Jun. 20, 2006; pp. 1-3; The Vegetarian Resource Group; located at http://www.vrg.org/nutrition/b12.htm; printed on Jul. 7, 2006.

Mcclatchey, Kenneth D.; "Clinical Laboratory Medicine"; Bearing a date of Jan. 15, 2002; 1693 pages; 2nd Edition; ISBN No. 0683307517; Lippincott Williams & Wilkins; Philadelphia, PA (not provided).

Mills, JL; Kirke, PN; Molloy AM; Burke, H; Conley, MR; Lee, YJ; Mayne, PD; Weir, DG; Scott, JM; "Methylenetetrahydrofolate reductase thermolabile variant and oral clefts"; Am. J. Med. Genet.; Bearing a date of Sep. 3, 1999; pp. 71-74 (p. 1); vol. 86, No. 1; PubMed; located at: http://www.ncbi.nlm.nih.gov/sites/entrez; printed on Jun. 25, 2007.

"Mineral & Toxic Element Tests"; Home Health Testing; Bearing dates of Dec. 1, 2005 and 2000; pp. 1-3; AbDiagnostics, Inc.; located at: http://www.homehealthtesting.com/mineral-tests.htm; printed on Jul. 24, 2006.

Morrow, Daniel G.; Leirer, Von O.; Andrassy, Jill M.; "Using icons to convey medication schedule information"; Abstract; Science

(56) References Cited

OTHER PUBLICATIONS

Direct; Bearing dates of Aug. 1996, May 3, 1999 and 2000; pp. 1-2; vol. 27, Issue 4; Elsevier Ltd.; located at http://www.sciencedirect.com/science?ob=ArticleURL&_udi=B6V1W-3WCSSG5-5&_coverDate=08%2F31%2F1996&_alid=413837048&_rdoc=1&_fmt=&_orig=search&_qd=1&_cdi=5685&_sort=d&view=c&_acct=C000050221&_version=1&_urlVersion=0&_userid=10&md5=8a92d091167ef0d84c80fe26ae9fdbae; printed on Jun. 7, 2006.

Morrow, Daniel G.; Weiner, Michael; Young, James; Steinley, Douglas; Deer, Melissa; Murray, Michael D.; "Improving Medication Knowledge Among Older Adults with Heart Failure: A Patient-Centered Approach to Instruction Design"; The Gerontologist; Bearing a date of 2005; pp. 545-552; vol. 45, No. 4; Practice Concepts; The Gerontological Society of America.

Mullan, Brian A.; Young, Ian S.; Fee, Howard; Mccance, David R.; "Ascorbic Acid Reduces Blood Pressure and Arterial Stiffness in Type 2 Diabetes"; Hypertension—Journal of the American Heart Association; Bearing dates of Oct. 21, 2002 and 2002; pp. 804-809 (pp. 1-7); vol. 40; Online ISSN 1524-4563; American Heart Association, Inc.; located at: http://hyper.ahajournals.org/cgi/content/full/40/6/804; printed on May 17, 2007.

"Nano World: Fast Flow Through Nanotube Membranes (Update)"; Physorg.com; Bearing a date of 2006; pp. 1-2; United Press International; located at: www.physorg.com/news67262683.html.

Nissen, David (Ed); Mosby's Drug Guide; Bearing a date of 2004; ISBN No. 0-323-02872-1; Mosby, Inc: Elsevier; St. Louis, MO (not provided).

"Occult Blood (stool)—Take-Home Test Kit—$25"; St. Vincent Healthcare; Bearing a date of 2006; p. 1; located at: http://www.svh-mt.org/services/all_health/labcheck/occult_blood.htm; printed on Jul. 10, 2006.

"OnTime-RX Medication Reminders"; Bearing dates of 2000-2004; pp. 1-4; AmeliaPlex, Inc.; Orlando, FL; located at: http://www.ontimerx.com/PDA/index.asp; printed on Nov. 13, 2005.

"Ovulation Predictor: Home Testing Kits"; Pharm.uky.edu; pp. 1-2; located at: http://www.pharm.uky.edu/hometest/Ovulate/OHP.html; printed on Jul. 10, 2006.

"Pain Relief / Injuries / Home Test Kits"; Round-Earth.com; pp. 1-2; Round Earth Publishing; located at: http://roundearth.stores.yahoo.net/relaxers.html; printed on Jul. 10, 2006.

Park, YK; Kim, JS; Kang, MH; "Concord grape juice supplementation reduces blood pressure in Korean hypertensive men: double-blind, placebo controlled intervention trial"; Biofactors; Bearing a date of 2004; pp. 145-147 (p. 1); vol. 22, Nos. 1-4; PubMed; located at: http://www.ncbi.nlm.nih.gov/sites/entrez?cmd=Retrieve&db=PubMed&dopt=Citation&list_uids=15630270; printed on May 17, 2007.

"Personal Test Kits: Hormone Saliva Test, Home Hormone Test Kit"; Womenshealth.com; Bearing a date of 2005; pp. 1-3; Women's Health America, Inc.; located at: http://www.womenshealth.com/personaltestkit.html; printed on Jul. 10, 2006.

Physicians' Desk Reference; The PDR Family Guide to Nutritional Supplements: An Authoritative A-to-Z Resource on the 100 Most Popular Nutritional Therapies and Nutraceuticals; Bearing a date of Nov. 2003; 3000 pp.; 58th Edition; ISBN No. 1563634724; Thomson PDR; Montvale, NJ (not provided).

Physicians' Desk Reference; The PDR Family Guide to Nutritional Supplements: An Authoritative A-to-Z Resource on the 100 Most Popular Nutritional Therapies and Nutraceuticals; Bearing a date of Nov. 27, 2001; 352 pages; 1st Edition; ISBN No. 0345433769; Ballantine Books (not provided).

Pregnancy Test, Ovulation Test, Drug Test by Medimpex; Bearing a date of 2002; pp. 1-3; Medimpex United Inc.; located Jul. 10, 2006 at: http://www.meditests.com/; printed on Jul. 10, 2006.

"Probiotics Basics"; Bearing a date of 2004; pp. 1-11; CDRF, Dairy & Food Culture Technologies; located at: http://www.usprobiotics.org/basics/; printed on Jul. 7, 2006.

"Quality Standards Issued for Testing Herbal Products"; ScienceDaily; Bearing dates of Apr. 18, 2006 and 1995-2006; pp. 1-2; ScienceDaily LLC; located at: http://www.sciencedaily.com/releases/2006/04/060418011332.htm; printed on Jul. 14, 2006.

Rapport, Lisa; Lockwood, Brian; Nutraceuticals; Bearing a date of Dec. 2001; 184 pages; 1st Edition; ISBN No. 0 85369 503 2; Pharmaceutical Press (not provided).

Roberts, Arthur J.; Subak-Sharpe, Genelle; O'Brien, Mary E.; Nutraceuticals: The Complete Encyclopedia of Supplements, Herbs, Vitamins, and Healing Foods; Bearing a date of Jan. 9, 2001; 669 pages; 1st Edition; ISBN No. 0399526323; Perigee Trade (not provided).

Sambrook, Joseph; Russell, David W.; "Molecular Cloning: A Laboratory Manual"; Bearing a date of Jan. 15, 2001; 2,344 pages; 3 Edition; ISBN 0-87969-577-3; Cold Spring Harbor Laboratory Press (not provided).

Samuel, Buck S.; Gordon, Jeffrey I.; "A Humanized Gnotobiotic Mouse Model of Host-Archaeal-Bacterial Mutualism"; PNAS; Bearing dates of 2006, Mar. 16, 2006, May 17, 2006 and Jun. 27, 2006; pp. 10011-10016; vol. 103, No. 26; The National Academy of Sciences of the USA; located at: www.pnas.org/cgi/doi/10.1073/pnas.0602187103.

Sarkar, FH; Adsule, S; Padhye, S; Kulkarni, S; Li, Y; "The role of genistein and synthetic derivatives of isoflavone in cancer prevention and therapy"; Mini Reviews in Medicinal Chemistry; Bearing a date of Apr. 2006; pp. 401-407 (pp. 1-2); vol. 6, Issue 4; PubMed; located at: http://www.ncbi.nlm.nih.gov/entrez/query.fcgi?CMD=Display&DB=pubmed; printed on Aug. 22, 2006.

"Search Results"; Health HomeTest.com; Bearing dates of 2003-2005; pp. 1-2; B Scientific, Inc.; located at: http://www.healthhometest.com/index.php?cPath=40; printed on Jul. 24, 2006.

Shizuka, F; Kido, Y; Nakazawa, T; Kitajima, H; Aizawa, C; Kayamura, H; Ichijo, N; "Antihypertensive effect of gamma-amino butyric acid enriched soy products in spontaneously hypertensive rats"; Biofactors; Bearing a date of 2004; pp. 165-167 (p. 1); vol. 22, Nos. 1-4; PubMed; located at: http://www.ncbi.nlm.nih.gov/sites/entrez?cmd=Retrieve&db=PubMed&list_uids=15630275&dopt=Abstract; printed on May 17, 2007.

Sholl, David S.; Johnson, J. Karl; "Materials Science: Making High-Flux Membranes with Carbon Nanotubes"; Science; Bearing a date of May 19, 2006; pp. 1003-1004; vol. 312; AAAS; located at: www.sciencemag.org.

"Single Parameter Test Kits"; Hach.com; Bearing a date of 2006; pp. 1-9; Hach Company; located at: http://www.hach.com/hc/browse.exploded.product.category.catalog/PRODCAT0033/NewLinkLabel=Single+Parameter+Test+Kits/PREVIOUS_BREADCRUMB_ID=HC_SEARCH_BROWSE/SESSIONID|BkUxTlRVM05UQTVPVFEzT0NabmRXVnpkRTVEVWc9PUEwdFhNVA==|; printed on Jul. 14, 2006.

Singh-Zocchi, Mukta; Dixit, Sanhita; Ivanov, Vassili; Zocchi, Giovanni; "Single-Molecule Detection of DNA Hybridization"; Bearing a date of Jun. 24, 2003; pp. 7605-7610; vol. 100, No. 13; located at: www.pnas.org/cgi/doi/10.1073/pnas.1337215100.

"Sleep Hormone Tests"; Home Health Testing; Bearing dates of Dec. 1, 2005 and 2000; pp. 1-3; AbDiagnostics, Inc.; located at: http://www.homehealthtesting.com/sleep-tests.htm; printed on Jul. 24, 2006

Smith, Ann; Heckelman, Patricia E.; O'Neil, Maryadele J. (Ed); Budavari, Susan (Ed); The Merck Index: An Encyclopedia of Chemicals, Drugs and Biologicals; Bearing a date of Oct. 2001; 2564 pages; 13th Edition; ISBN No. 0911910131; John Wiley and Sons and Merck & Co. Inc.; Whitehouse Station, NJ (not provided).

Sojourner, Russell J.; Wogalter, Michael S.; "The Influence of Pictorials on Evaluations of Prescription Medication Instructions"; Drug Information Journal; Bearing a date of 1997; pp. 963-972; vol. 31; Drug Information Association, Inc.

"Spectrophotometers and Colorimeters"; Hach.com; Bearing a date of 2006; pp. 1-2; Hach Company; located at: http://www.hach.com/hc/browse.exploded.product.category.catalog/PRODCAT0001/NewLinkLabel=Spectrophotometers+%26+Colorimeters/PREVIOUS_BREADCRUMB_ID=HC_SEARCH_BROWSE/SESSIONID|A3INVE14TnpJeU1TWm5kVIZ6ZEZCW1QxZElNVEUxTlE9PUNUTQ==|; printed on Jul. 14, 2006.

Steenge, Gery R.; Verhoef, Petra; Katan, Martijn B.; "Human Nutrition and Metabolism—Betaine Supplementation Lowers Plasma

(56) References Cited

OTHER PUBLICATIONS

Homocysteine in Healthy Men and Women"; The Journal of Nutrition; Bearing a date of 2003; pp. 1291-1295; vol. 133; American Society for Nutritional Sciences; located at: jn.nutrition.org; printed on May 17, 2007.
Subbiah, MT; "Nutrigenetics and Nutraceuticals: the next wave riding on personalized medicine"; Transl Res.; Bearing a date of Feb. 2007; pp. 55-61 (pp. 1-2); vol. 149, No. 2; PubMed; located at: http://www.ncbi.nlm.nih.gov/sites/entrez; printed on Jun. 25, 2007.
"Stress Hormone Tests"; Home Health Testing; Bearing dates of Dec. 1, 2005 and 2000; pp. 1-3; AbDiagnostics, Inc.; located at: http://www.homehealthtesting.com/stress-hormone-tests.htm; printed on Jul. 24, 2006.
"Talking Medicine Identifiers"; Bearing a date of Jul. 10, 2003; pp. 1-5.
"UV-Vis-NIR Advantage Note"; Bearing a date of May 2005; No. 1; pp. 1-3; Varian, Inc.; located at: www.varianinc.com/image/vimage/docs/applications/apps/uv_anl.pdf: printed on Jul. 14, 2006.
"UV-Vis-IR-Raman Spectrophotometers"; Micro Photonics; Bearing a date of Dec. 7, 2005; pp. 1-2; Micro Photonics, Inc.; located at: http://www.microphotonics.com/spectrophotometer.html; printed on Jul. 14, 2006.
Vieira Da Costa, VA; Vianna, LM; "Effect of alpha-tocopherol supplementation on blood pressure and lipidic profile in streptozotocin-induced diabetes mellitus in spontaneously hypertensive rats"; Clin. Chim. Acta.; Bearing a date of Jan. 2005; pp. 101-104 (p. 1); vol. 351, Nos. 1-2; PubMed; located at: http://www.ncbi.nlm.nih.gov/sites/entrez; printed on May 17, 2007.
Wald, NJ; Law, MR; "A strategy to reduce cardiovascular disease by more than 80%"; BMJ; Jun. 28, 2003; pp. 1-6; vol. 326; located at: www.bmj.com.
Wallerath, T; Deckert, G; Ternes, T; Anderson, H; Li, H; Witte, K; Forstermann, U; "Resveratrol, a polyphenolic phytoalexin present in red wine, enhances expression and activity of endothelial nitric oxide synthase"; Circulation; Bearing a date of Sep. 24, 2002; pp. 1652-1658 (pp. 1-2); vol. 106, Issue 13; PubMed; located at: http://www.ncbi.nlm.nih.gov/entrez/query.fcgi?cmd=Retrieve&db=PubMed&list_uids=12270858&dopt=Abstract; printed on Aug. 22, 2006.
Walji, Rishma; "Acidophilus Effects, Benefits and Other Information"; About: Alternative Medicine; Bearing a date of 2006; p. 1; About, Inc., A part of The New York Times Company; located at: http://altmedicine.about.com/cs/digestiveproblems/a/Acidophilus.htm; printed on Jul. 7, 2006.
Walji, Rishma; "What are Probiotics?"; About: Alternative Medicine; Bearing a date of 2006; p. 1; About, Inc., A part of The New York Times Company; located at: http://altmedicine.about.com/cs/digestiveproblems/a/Acidophilus_2.htm; printed on Jul. 7, 2006.
Wan, Ruiqian; Camandola, Simonetta; Mattson, Mark P.; "Dietary supplementation with 2-deoxy-d-glucose improves cardiovascular and neuroendocrine stress adaptation in rats"; Am. J. Physiol Heart Circ. Physiol; Bearing dates of Oct. 10, 2003 and Apr. 26, 2004; pp. 1-13; vol. 287; American Physiological Society; located at: http://ajpheart.physiology.org/cgi/content/full/287/3/H1186; printed on May 17, 2007.
Wang, J.; Li, J.; Baca, AJ.; HU, J.; Zhou, F.; Yan, W.; Pang, DW.; "Amplified Voltammetric Detection of DNA Hybridization via Oxidation of Ferrocene Caps on Gold Nanoparticle/Streptavidin Conjugates"; Anal. Chem.; Bearing a date of Aug. 1, 2003; pp. 3941-3945 (p. 1); vol. 75, No. 15; PubMED; located at: http://www.ncbi.nlm.nih.gov/entrez/query.fcgi?cmd=Retrieve&db=PubMed&list_uids=14572067&dopt=Abstract; printed on Nov. 29, 2006.
West, SG; Likos-Krick, A; Brown, P; Mariotti, F; "Oral L-arginine improves hemodynamic responses to stress and reduces plasma homocysteine in hypercholesterolemic men"; J. Nutr.; Bearing a date of Feb. 2005; pp. 212-217 (p. 1-2); vol. 135, No. 2; PubMed; located at: http://www.ncbi.nlm.nih.gov/sites/entrez?cmd=Retrieve&db=pubmed&dopt=Abstract&list_uids=15671215; printed on Jun. 25, 2007.
"What are Probiotics?"; USProbiotics; Bearing a date of 2004; 1 page; CDRF, Dairy & Food Culture Technologies; located at: http://www.usprobiotics.org/mainpageframe.htm; printed on Jul. 7, 2006.
Widdershoven, J.; Van Munster, P.; De Abreu, R.; Bosman, H.; Van Lith, TH.; Van Der Putten-Van Meyel, M.; Motohara, K.; Matsuda, I.; "Four Methods Compared for Measuring Des-Carboxy-Prothrombin (PIVKA-II)"; Clinical Chemistry; Bearing a date of 1987; pp. 2074-2078; vol. 33, No. 11.
Wilson, A; Platt, R; Wu, Q; Leclerc, D; Christensen, B; Yang, H; Gravel, RA; Rozen, R; "A common variant in methionine synthase reductase combined with low cobalamin (vitamin B12) increases risk for spina bifida"; Mol. Genet. Metab.; Bearing a date of Aug. 1999; pp. 317-323 (p. 1); vol. 67, No. 4; PubMed; located at: http://www.ncbi.nlm.nih.gov/sites/entrez; printed on Jun. 25, 2007.
Wildman, Robert E.C.; Handbook of Nutraceuticals and Functional Foods; Bearing a date of Nov. 10, 2000; 568 pages; $1^{st}$ Edition; ISBN No. 0849387345; CRC Press (not provided).
Wynn, Susan G.; Emerging Therapies: Using Herbs and Nutraceuticals for Small Animals; Bearing a date of 1999; 160 pages; $1^{st}$ Edition; ISBN No. 1583260102; American Animal Hospital Assn Press (not provided).
Xiao, YI; Lubin, Arica A.; Baker, Brian R.; Plaxco, Kevin W.; Heeger, Alan J.; "Single-Step Electronic Detection of Femtomolar DNA by Target-Induced Strand Displacement in an Electrode-Bound Duplex"; PNAS; Bearing a date of Nov. 7, 2006; pp. 16677-16680; vol. 103, No. 45; located at: www.pnas.org/cgi/doi/10.1073/pnas.0607693103.
U.S. Appl. No. 12/011,008, Jung et al.
U.S. Appl. No. 11/977,174, Jung et al.
PCT International Search Report; International App. No. PCT/US06/47436; dated Jan. 30, 2008; pp. 1-2.
Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.
Leibovici, Leonard et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.
PCT International Search Report; International App. No. PCT/US07/25379; dated May 13, 2008; 1-2.
PCT International Search Report; International App. No. PCT/US07/25417; dated May 14, 2008; pp. 1-3.
PCT International Search Report; International App. No. PCT/US07/25417; dated May 19, 2008; pp. 1-2.
PCT International Search Report; International App. No. PCT/US2007/025450; dated May 23, 2008; pp. 1-2.
PCT International Search Report; International App. No. PCT/US06/47835; dated Jul. 14, 2008; pp. 1-2.
Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.
PCT International Search Report; International App. No. PCT/US07/25451; dated Sep. 15, 2008; pp. 1-2.
PCT International Search Report; International App. No. PCT/US07/20272; dated Sep. 15, 2008; pp. 1-2.
PCT International Search Report; International App. No. PCT/US07/20305; dated Sep. 11, 2008; pp. 1-2.
PCT International Search Report; International App. No. PCT/US07/20283; dated Sep. 11, 2008; pp. 1-2.
PCT International Search Report; International App. No. PCT/US07/14994; dated Sep. 9, 2008; pp. 1-2.
PCT International Search Report; International App. No. PCT/US08/07993; dated Sep. 8, 2008; pp. 1-3.
PCT International Search Report; International App. No. PCT/US06/47451; dated Sep. 5, 2008; pp. 1-2.
PCT International Search Report; International App. No. PCT/US06/44658; dated Aug. 29, 2008; pp. 1-2.
PCT International Search Report; International App. No. PCT/US06/44279; dated Aug. 19, 2008; pp. 1-3.

(56) References Cited

OTHER PUBLICATIONS

PCT International Search Report; International App. No. PCT/US06/44283; dated Aug. 18, 2008; pp. 1-2.
PCT International Search Report; International App. No. PCT/US07/14266; dated Jul. 21, 2008; pp. 1-2.
U.S. Appl. No. 11/893,608, Jung et al.
U.S. Appl. No. 11/893,606, Jung et al.
U.S. Appl. No. 11/893,605, Jung et al.
U.S. Appl. No. 11/888,627, Jung et al.
U.S. Appl. No. 11/888,614, Jung et al.
U.S. Appl. No. 11/888,613, Jung et al.
"Smart Pillbox Goes Direct to Consumer"; Health Data Management; Bearing dates of Aug. 28, 2007 and Aug. 29, 2007; pp. 1-2; Health Data Management and SourceMedia, Inc.; located at: http://healthdatamanagement.com/html/news/NewsStory.cfm?articleId=15652; printed Aug. 29, 2007.
Edible Science; bearing dates of 2005-2010; pp. 1-2; located at: http://www.ediblescience.com; printed on May 13, 2010.
Fightermins; bearing a date of 2010; 1 page; located at: http://www.figtermins.com/index.jsp; printed on May 13, 2010.
Ideal Health; "Custom Essentials"; "The Priva Test"; bearing a date of 2010; total of 5 pages; located at: http://www.idealhealth.com; printed on May 13, 2010; The Trump Network.
I-Vita; bearing a date of 2009; 1 page; located at: http://www.mynutrapack.com/index.html; printed on May 13, 2010.
LifeScript; bearing dates of 1998-2010; 1 page; located at: http://vitamins.lifescript.com/Begin.asp?BID=14971&PROMO=zluswiec; printed on May 13, 2010.
Mindell, Earl, Dr.; Vitaganic "Custom-Made Multivitamins"; bearing dates of 2005-2010; 1 page; located at: http://drmindell.vitaganic.com/; printed on May 13, 2010.
My Vitamin Clinic; bearing a date of 2010; 1 page; located at: http://www.myvitaminclinic.com/index.jsp; printed on May 13, 2010.
MyNutraPack; 1 page; located at: http://www.mynutrapack.com/index.html; printed on May 25, 2010.
MyVitaminRx; bearing a date of 2007; 1 page; located at: http://www.myvitaminsrx.com/CustomNutrition/CustomNutrition.aspx?ID=MoonlightSpa; printed on May 13, 2010.
Nature Made; pp. 1-2; located at: http://www.naturemade.com/; printed on May 13, 2010.
NutriHerb; bearing dates of 2001-2009; pp. 1-2; Nutri Herb, Inc.; located at: http://www.nutriherb.net/custom_made_to_order_herbal_vitamins_supplements.html; printed on May 13, 2010.
Pharmative LLC; 1 page; located at: http://www.pharmavite.com/index.asp; printed on May 13, 2010.
"Pharmavite LLC Launches New Direct-to-Consumer Company" Press Release; Pharmavite LLC; bearing a date of Sep. 4, 2009; 1 page; located at: http://www.pharmavite.com/MediaCenter/MC_PR.asp?ID=164; printed on May 13, 2010.
Signature Supplements; bearing a date of 2009; pp. 1-2; located at: http://www.signaturesupplements.com/jsp/main/index.jsp; printed on May 13, 2010; Signature Supplements.
SOYJOY®; bearing a date of 2010; 1 page; located at: http://www.soyjoy.com/index.aspx; printed on May 13, 2010; Pharmavite LLC.
Total Health Nutrients; pp. 1-2; located at: http://www.totalhealthnutrients,com/ph/index.html; printed on May 13, 2010.
VitaminID.com; bearing a date of 2010; 1 page; located at: http://www.vitaminid.com/webapp/wcs/stores/servlet/StoreView?storeId=201&langID=-1; printed on May 25, 2010; Pharmavite Direct LLC.
Vitamins on Demand; bearing a date of 2010; 1 page; located at http://www.vitaminsondemand.com/?gclid=CNbygPut9aACFRYhDQodyGkivw; printed on May 13, 2010.
VitaXact; bearing a date of 2009; 1 page; located at: http://www.vitaxact.com; printed on May 13, 2010.
Weil, Andrew, M.D.; "Dr. Weil's Vitamin Advisor & Complete Program Supplements"; bearing a date of 2010; 1 page; located at: https://www.drweilvitaminadvisor.com/drw/ecs/Va2/land_goog_08girl.html?aid=999910&aparam=TSAsGoogleApr10VA_vitamins&refcd=GO000000101882154s_vitamins&tsacr=GO3784957603&gclid=CM3NpLzm9aACFRYhDQodyGkivw; printed on May 13, 2010, Weil Lifestyle Custom Pak.
Evans, R. Scott, Ph.D. et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.), Critical Care (T.P.C., L.K.W., J.F.O.,), and Medical Informatics (R.S.E.), LDS Hospital, Salt Lake City, UT.
U.S. Appl. No. 12/924,700, Jung et al.
Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.
Sriskanthan, N. and Subramanian, K. R.; "Braille Display Terminal for Personal Computers"; IEEE Transactions on Consumer Electronics; May 1990; pp. 121-128; vol. 36, No. 2; IEEE.
UK Intellectual Property Office Examination Report Under Section 18(3); App. No. GB1000316.8; dated Jul. 26, 2011; pp. 1-3.
U.S. Appl. No. 13/374,765, Jung et al.
Walt et al.; "Biological Warfare, A Host of Detection Strategies Have Been Developed, but Each Has Significant Limitations"; Analytical Chemistry; bearing a date of Dec. 1, 2000; pp. 738A-747A.
"Microsoft Press Computer Dictionary: The Comprehensive Standard for Business, School, Library, and Home"; bearing a date of Nov. 1, 1993; 1 page; Edition 2; Microsoft Press; IBSN: 9781556155970 (whole book not provided).
"Garlic Nature's Amazing Nutritional and Medicinal Wonder Food"; pp. 1-32; Bearing a date of 1995, Created on Jul. 3, 2014, as provided; Woodland Publishing, Inc.; Pleasant Grove, UT.
Sabate et al; "Handbook of Nutraceuticals and Functional Foods, Chapter 28: The Role of Nuts in Cardiovascular Disease Prevention"; pp. 1-19; Bearing a date of 2001, Created on Jul. 3, 2014, as provided; CRC Press LLC.
Krishna et al.; "Glutathione and γ-glutamyl transpeptidase are differentially distributed in the olfactory mucosa of rats"; Cell Tissue Res; bearing a date of Jul. 1992; pp. 475-484; vol. 270; Springer-Verlag.

\* cited by examiner

COMPUTATIONAL SYSTEMS AND METHODS RELATED TO NUTRACEUTICALS

RELATED APPLICATIONS

For purposes of the USPTO extra-statutory requirements, the present application constitutes a continuation-in-part of U.S. patent application Ser. No. 11/453,571, entitled INDIVIDUALIZED PHARMACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/824,604, entitled COMPUTATIONAL SYSTEMS RELATED TO NUTRACEUTICALS, naming Edward K. Y. Jung, Royce A. Levien, Robert W. Lord, Mark A. Malamud, John D. Rinaldo, Jr., Clarence T. Tegreene and Lowell L. Wood, Jr. as inventors, filed 28 Jun. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,341, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,296, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 28 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,998, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/486,973, entitled COMPUTATIONAL AND/OR CONTROL SYSTEMS RELATED TO INDIVIDUALIZED PHARMACEUTICAL AND NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 14 Jul. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/474,109, entitled CUSTOMIZED VISUAL MARKING FOR MEDICATION LABELING, naming Edward K. Y. Jung, Royce A. Levien, Robert W. Lord, Mark A. Malamud, John D. Rinaldo, Jr., and Lowell L. Wood, Jr. as inventors, filed 23 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/515,357, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 1 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/518,540, entitled INDIVIDUALIZED PHARMACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed 8 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,766, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 18 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,809, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed 18 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/637,638, entitled METHODS AND SYSTEMS FOR ANALYSIS OF NUTRACEUTICAL ASSOCIATED COMPONENTS, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Dec. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/637,616, entitled METHODS AND SYSTEMS FOR ANALYSIS OF NUTRACEUTICAL ASSOCIATED COMPONENTS, naming Edward K. Y. Jung, Eric C. Leuthardt, Royce A. Levien, Robert W. Lord, Mark A. Malamud, John D. Rinaldo, Jr., and Lowell L. Wood, Jr. as inventors, filed 11 Dec. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/314,945, entitled GENERATING A REQUEST FROM A NUTRACEUTICAL INVENTORY, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 20 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/291,482, entitled GENERATING A NUTRACEUTICAL REQUEST FROM AN INVENTORY, naming Edward K. Y. Jung, Royce A. Levien, Robert W. Lord, Mark A. Malamud, John D. Rinaldo, Jr., Clarence T. Tegreene, and Lowell L. Wood, Jr. as inventors, filed 30 Nov. 2005, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

TECHNICAL FIELD

The present disclosure relates to computational systems and methods related to nutraceuticals.

SUMMARY

In some embodiments a method is provided that includes accepting input associated with nutraceutical usage by one or more individuals, accepting input associated with one or more parameters related to the one or more individuals, and processing the input associated with the nutraceutical usage by the one or more individuals and the input associated with the one or more parameters related to the one or more individuals. The method may optionally include displaying results of the processing. The method may optionally include comparing results of the processing of the one or more individuals with one or more substantially similar results obtained for one or more other individuals. The method may optionally include displaying results of the comparing. In addition to the foregoing, other method aspects are described in the claims, drawings, and/or text forming a part of the present disclosure.

In some embodiments a method is provided that includes accepting input associated with nutraceutical usage by one or more individuals, accepting input associated with one or more parameters related to the one or more individuals, and transmitting one or more signals that include information related to the input associated with the nutraceutical usage by the one or more individuals and to the input associated with the one or more parameters related to the one or more individuals. In addition to the foregoing, other method aspects are described in the claims, drawings, and/or text forming a part of the present disclosure.

In some embodiments a method is provided that includes accepting input associated with nutraceutical usage by one or more individuals, accepting input associated with one or more parameters related to the one or more individuals, processing the input associated with the nutraceutical usage by the one or more individuals and the input associated with the one or more parameters related to the one or more individuals, and transmitting one or more signals that include information related to results of the processing. In addition to the foregoing, other method aspects are described in the claims, drawings, and/or text forming a part of the present disclosure.

In some embodiments a method is provided that includes receiving one or more signals that include information related to results of processing input associated with nutraceutical usage by one or more individuals and input associated with one or more parameters related to the one or more individuals and determining one or more nutraceutical associated parameters based on the results of the processing. The method may optionally include transmitting the one or more signals that include information related to the determining one or more nutraceutical associated parameters based on the results of the processing. In addition to the foregoing, other method aspects are described in the claims, drawings, and/or text forming a part of the present disclosure.

In some embodiments a method is provided that includes receiving one or more signals that include information related to determining one or more nutraceutical associated parameters based on results of processing input associated with nutraceutical usage by one or more individuals and input associated with one or more parameters related to the one or more individuals and displaying the information. In addition to the foregoing, other method aspects are described in the claims, drawings, and/or text forming a part of the present disclosure.

In some embodiments a system is provided that includes means for accepting input associated with nutraceutical usage by one or more individuals, means for accepting input associated with one or more parameters related to the one or more individuals, and means for processing responsive to the means for accepting input associated with the nutraceutical usage by the one or more individuals and the means for accepting input associated with the one or more parameters related to the one or more individuals. In addition to the foregoing, other system aspects are described in the claims, drawings, and/or text forming a part of the present disclosure.

In some embodiments a system is provided that includes means for accepting input associated with nutraceutical usage by one or more individuals, means for accepting input associated with one or more parameters related to the one or more individuals, and means for transmitting one or more signals responsive to the means for accepting input associated with the nutraceutical usage by the one or more individuals and to the means for accepting input associated with the one or more parameters related to the one or more individuals. In addition to the foregoing, other system aspects are described in the claims, drawings, and/or text forming a part of the present disclosure.

In some embodiments a system is provided that includes means for accepting input associated with nutraceutical usage by one or more individuals, means for accepting input associated with one or more parameters related to the one or more individuals, means for processing responsive to the means for accepting input associated with the nutraceutical usage by the one or more individuals and the means for accepting input associated with the one or more parameters related to the one or more individuals, and means for transmitting one or more signals responsive to the means for processing. In addition to the foregoing, other system aspects are described in the claims, drawings, and/or text forming a part of the present disclosure.

In some embodiments a system is provided that includes means for receiving one or more signals that include information related to results of processing input associated with nutraceutical usage by one or more individuals and input associated with one or more parameters related to the one or more individuals and means for determining one or more nutraceutical associated parameters responsive to the means for receiving. The system may optionally include means for transmitting one or more signals responsive to the means for determining. In addition to the foregoing, other system aspects are described in the claims, drawings, and/or text forming a part of the present disclosure.

In some embodiments a system is provided that includes means for receiving one or more signals that include information related to determining one or more nutraceutical associated parameters based on results of processing input associated with nutraceutical usage by one or more individuals and input associated with one or more parameters related to the one or more individuals and means for displaying the information. In addition to the foregoing, other system aspects are described in the claims, drawings, and/or text forming a part of the present disclosure.

In some embodiments, means include but are not limited to circuitry and/or programming for effecting the herein-referenced functional aspects; the circuitry and/or programming can be virtually any combination of hardware, software, and/or firmware configured to effect the herein-referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
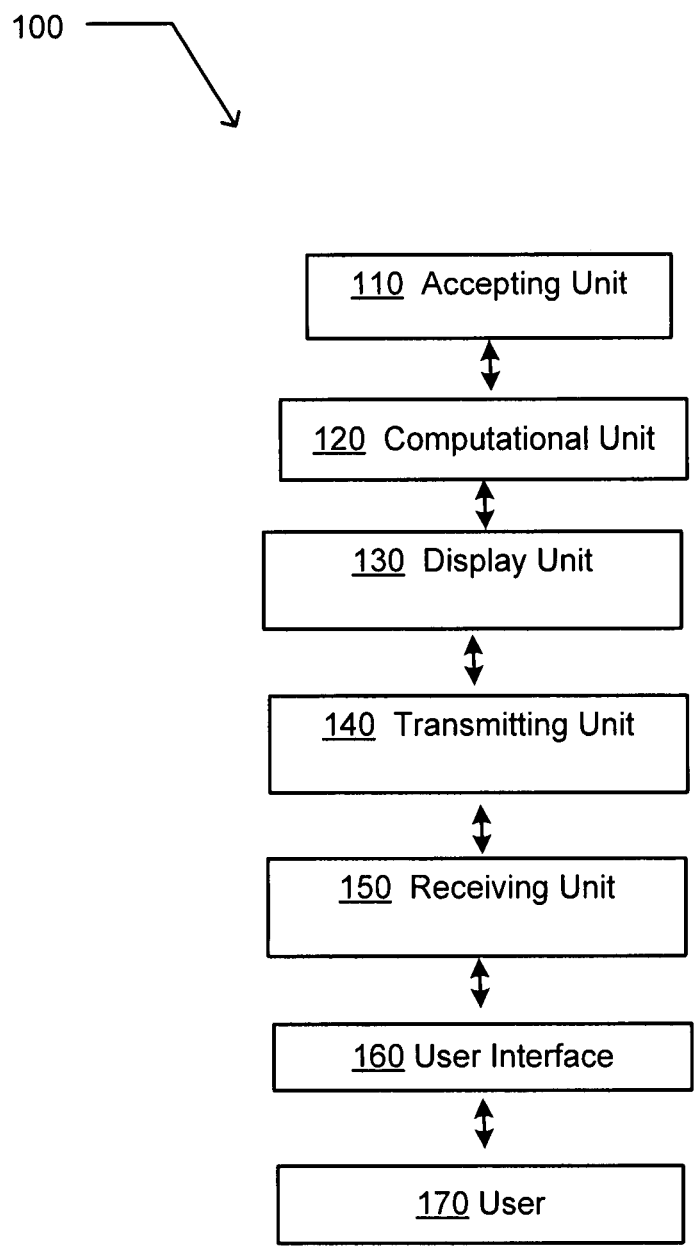
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method and system 100 for nutraceutical related analysis. In some embodiments, system 100 may include one or more accepting units 110. In some embodiments, system 100 may include one or more computational units 120. In some embodiments, system 100 may include one or more display units 130. In some embodiments, system 100 may include one or more transmitting units 140. In some embodiments, system 100 may include one or more receiving units 150. In some embodiments, system 100 may include one or more user interfaces 160.

Accepting Unit

The system 100 can include one or more accepting units 110. In some embodiments, one or more accepting units 110 can include a physical device which allows input entry, such as a touchpad, keypad, hardwired telephone, and the like. In some embodiments, one or more accepting units 110 can include a wireless connection that allows the one or more accepting units 110 to accept input from one or more users 170 through a wireless connection. For example, in some embodiments, one or more accepting units 110 may accept input from one or more users 170 through use of a cellular telephone, a personal digital assistant, a wireless computer, and the like.

In some embodiments, one or more accepting units 110 can be used to intake information related to one or more parameters associated with one or more specified goals of an individual. In some embodiments, one or more accepting units 110 may be used to accept input related to one or more levels of one or more metabolic indicators related to one or more individuals. In some embodiments, one or more accepting units 110 may accept input related to one or more levels of one or more metabolic activities linked to one or more individuals. In some embodiments, one or more accepting units 110 may accept one or more levels of one or more nutraceuticals used by one or more individuals. In some embodiments, one or more accepting units 110 may accept input related pharmaceutical usage by one or more individuals. In some embodiments, one or more accepting units 110 may accept input from another device. For example, in some embodiments, one or more accepting units 110 may accept input from a diagnostic device. Such diagnostic devices include, but are not limited to, devices used to analyze bodily samples obtained from an individual (i.e., blood, urine, saliva, synovial fluid, pleural fluid, peritoneal fluid, breath, skin, tissue, tears, mucus, genital products, hair, fecal material, and the like), devices used to analyze the appearance of an individual (i.e., eye color, skin color, hair color, the presence or absence of bags under the eyes, presence or absence of hair, and the like), devices used to analyze a characteristic of the individual (i.e., speech, reaction time, reflexes, temperature, eye dilation, retinal profile, height, weight, waistline, and the like), and other devices used to diagnose and/or analyze an individual.

Computational Unit

The system 100 may include one or more computational units 120. In some embodiments, one or more computational units 120 may be used to process input associated with nutraceutical usage by one or more individuals and input associated with one or more parameters related to the one or more individuals. A computational unit 120 may process input in numerous ways. For example, in some embodiments, one or more computational units 120 may compare input related to an individual to one or more other individuals. Accordingly, in some embodiments, system 100 provides for comparison of an individual's nutraceutical usage to other individuals. In some embodiments, one or more computational units 120 may analyze input in a time dependent manner. For example, in some embodiments, one or more computational units 120 may be used to titrate nutraceutical usage may an individual. Accordingly, in some embodiments, an individual may be able to determine such factors as nutraceutical dosage, time of administration, route of administration, and the like, that will provide an individual with an increased benefit from nutraceutical usage.

Nutraceutical

Nutraceuticals typically include natural, bioactive chemical compounds or any substance that is a plant, food, an extracted part of a food, that provides medical or health benefits but which generally fall outside regulations controlling pharmaceuticals. Included in this category of substances may be foods, isolated nutrients, supplements and herbs. Nutraceuticals are often referred to as phytochemicals or functional foods and include dietary supplements. Numerous nutraceuticals have been described (i.e., Roberts et al., Nutraceuticals: The Complete Encyclopedia of Supplements, Herbs, Vitamins, and Healing Foods, $1^{st}$ Edition, Perigee Trade (2001) and Susan G. Wynn, Emerging Therapies: Using Herbs and Nutraceuticals for Small Animals, American Animal Hospital Assn Press (1999); and Handbook of Nutraceuticals and Functional Foods., edited by Robert E. C. Wildman, CRC Press (2001)). Examples of nutraceuticals include, but are not limited to, Amino Acids, Terpenoids, Carotenoid Terpenoids (Lycopene, Beta-Carotene, Alpha-Carotene, Lutein, Zeaxanthin, Astaxanthin), Herbal Supplements, Homeopathic Supplements, Glandular Supplements, Non-Carotenoid Terpeniods (Perillyl Alcohol, Saponins, Terpeneol, Terpene Limonoids), Polyphenolics, Flavonoid Polyphenolics (Anthocyanins, Catechins, Isoflavones, Hesperetin, Naringin, Rutin, Quercetin, Silymarin, Tangeretin, Tannins), Phenolic Acids (Ellagic Acid, Chlorogenic Acid, Para-Coumaric Acid, Phytic Acid, Cinnamic Acid), Other Non-Flavonoid Polyphenolics (Curcumin, Resveratrol, Lignans), Glucosinolates, Isothiocyanates (Phenethyl Isothiocyanate, Benzyl Isothiocyanate, Sulforaphane), Indoles (Indole-3-Carbinol (I3C), Thiosulfonates, Phytosterols (Beta-Sitosterol), Anthraquinones (Senna, Barbaloin, Hypericin), Capsaicin, Piperine, Chlorophyll, Betaine, Pectin, Oxalic Acid, Acetyl-L-Carnitine, Allantoin, Androsterondiol, Androsterondione, Betaine (Trimethylglycine), Caffeine, Calcium pyvurate (Pyruvic Acid), Carnitine, Carnosine, Carotene (alpha & beta), Carotenoid (Total for beadlets), Choline, Chlorogenic Acid, Cholic Acid (Ox Bile), Chondroitin Sulfate, Chondroitin Sulfate (Total Mucopolysaccharides), Cholestin, Chrysin, Coenzyme Q10 (Co-Q10), Conjugated Linoleic Acid (CLA), Corosolic Acid, Creatine, Dehydroepiandrosterone (DHEA), Dichlorophen, Diindolymethane (DIM), Dimethyglycine (DMG), Dimercapto Succinic Acid (DMSA), Ebselen, Ellagic Acid, Enzymes, Fisetin, Formonetin, Glucaric Acid (Glucarate), Glucosamine (HCl or Sulfate), Glucosamine (N-Acetyl), Glutathione (Reduced), Hesperidine, Hydroxy-3-Methylbutyric Acid (HMB), 5-Hydroxytryptophan (L-5-HTP), Indole-3-Carbinol, Inositol, Isothiocyanates, Linolenic Acid-Gamma (GLA), Lipoic Acid (alpha), Melatonin, Methylsulfonylmethane (MSM), Minerals, Naringin, Pancreatin, Para-aminobenzoic Acid (PABA), Paraben (methyl or propyl), Phenolics, Phosphatidylcholine (Lecithin), Phosphatidylserine, Phospholipids, Phytosterols, Pregersterone, Pregnenolone, Quercetin, Resveratrol, D-Ribose, Rutin, S-adenosylmethionine (SAM-e), Salicylic Acid, Sulforaphane, Tartaric Acid, Taxifolin, Tetrahydropalmatine, Thephyline, Theobromine, Tigogenin, Troxerutin, Tryptophan, Tocotrienol (alph, beta & gamma), Vitamins, Zeaxanthin, *Gingo Biloba*, Ginger, Cat's Claw, *Hypericum, Aloe Vera*, Evening Primrose, Garlic, *Capsicum*, Dong Quai, Ginseng, Feverview, Fenugreek, *Echinacea*, Green Tea, Marshmallow, Saw Palmetto, Tea Tree Oil, *Payllium*, Kava-Kava, Licorice Root, *Manonia Aquifolium*, Hawthorne, Hohimbr, Tumeric, Witch Hazel, Valerian, Mistletoe, Bilberry, Bee Pollen, Peppermint Oil, Beta-Carotene, Genistein, Lutein, Lycopene, the Polyphenols (bioflavonoids), and the like.

In some embodiments, a nutraceutical may include microbes (i.e., probiotics). Examples of such microbes include, but are not limited to, *Lactobacillus acidophilus, Lactobacillus plantarum, Lactobacillus casei, Bifidobacterium bifidum, Bifidobacterium longum, Saccharomyces boulardii, Saccharomyces cerevisiae*, and the like (i.e., Samuel and Gordon, A humanized gnotobiotic mouse model of host-archaeal-bacterial mutualism, PNAS, 103(26):10011-10016 (2006)). In some embodiments, a nutraceutical may include non-living microbes. For example, non-living *Saccharomyces cerevisiae* may be used as a source of vitamin B12. In some embodiments, recombinant microbes may be utilized as nutraceuticals. For example, in some embodiments, microbes may be genetically modified to produce, or overexpress, one or more nutraceuticals.

Display Unit

The system 100 can include one or more display units 130. In some embodiments, one or more display units 130 can be used to indicate one or more nutraceuticals in response to input related to one or more parameters related to one or more individuals. In some embodiments, one or more display units 130 can be used to indicate one or more dosages of one or more nutraceuticals in response to input related to one or more parameters related to one or more individuals. In some embodiments, one or more display units 130 may display one or more dosages of one or more nutraceuticals in human-readable format. In some embodiments, one or more display units 130 may display one or more dosages of one or more nutraceuticals in machine-readable format. In some embodiments, one or more display units 130 can be included within system 100 through use of a hardwired connection. In some embodiments, one or more display units 130 can be included within system 100 through use of a wireless connection. In some embodiments, one or more display units 130 can be included within system 100 through use of a hardwired and a wireless connection.

Dosage

Dosages may be expressed in numerous ways. In some embodiments, a dosage may be expressed as an absolute quantity (i.e., 500 milligrams of a nutraceutical). In other embodiments, a dosage may be expressed in accordance with the body weight of an individual (i.e., 10 milligram nutraceutical agent 118 per kilogram body weight). In some embodiments, a dosage may be expressed as a range of quantities (i.e., 10 milligrams to 100 milligrams of a nutraceutical). In some embodiments, a dosage may be an amount of a nutraceutical that produces a desired response when administered to a specific individual. For example, a dosage of melatonin may be the amount of melatonin that induces sleep in a specific individual. The dosage of a nutraceutical may vary according to numerous considerations that include, but are not limited to, the route of administration, the age of the individual, the size of the individual, the metabolic characteristics of the individual, the condition of the individual, and the like. In some embodiments, the dosage of a nutraceutical may be determined that produces a measurable effect, such as a physical effect, a psychological effect, a physiological effect, and the like. Accordingly, in some embodiments, a dosage may be expressed as an amount of a nutraceutical that produces a mental response in an individual. For example, in some embodiments, a dosage may be the amount of a nutraceutical that produces a sensation of well-being when administered to an individual. In other embodiments, a dosage may be the amount of a nutraceutical that elevates the mood of an individual to whom the nutraceutical is to be administered. Numerous additional criteria may be used to determine the dosage of a nutraceutical for administration to an individual.

In some embodiments, one or more display units 130 can display one or more dosages of one or more nutraceuticals and one or more formulations of the one or more nutraceuticals. For example, in some embodiments, one or more display units 130 may indicate a formulation and dosage of chromium. Presently, the most widely available chromium supplements are chromium salts such as chromium polynicotinate, chromium picolinate, and various chromium/amino acid chelates. Such formulations help increase the absorption and availability of chromium when compared to isolated chromium salts such as chromium chloride. The estimated safe and adequate daily dietary intake of chromium is 50-200 micrograms. Natural forms of supplemental chromium, such as chromium-rich yeast, may be absorbed somewhat more efficiently than inorganic forms of chromium, such as chromium chloride, found in some supplements. One ounce of brewer's yeast provides approximately 100-200 micrograms of chromium. Accordingly, in some embodiments, one or more display units 130 may display a dosage of chromium and a corresponding formulation of the chromium. In another embodiment, one or more display units 130 may display a dosage of vitamin A. For vitamin A deficiency syndromes, vitamin A may be orally supplemented at a dosage of 600 micrograms for children aged 3 years or younger, 900 micrograms for children aged 4-8 years, 1700 micrograms for children aged 9-13 years, 2800 micrograms for persons aged 14-18 years, and 3000 micrograms for all adults. Therapeutic doses for severe disease include 60,000 micrograms, which has been shown to reduce child mortality rates by 35-70%. One or more display units 130 may indicate dosages for numerous types of nutraceuticals that are formulated in numerous ways.

Transmitting Unit

The system 100 can include one or more transmitting units 140. In some embodiments, one or more transmitting units 140 can be used to transmit one or more signals in response to input related to one or more individuals. In some embodiments, one or more transmitting units 140 can be used to transmit one or more levels of one or more metabolic indicators related to an individual. In some embodiments, one or more transmitting units 140 can be used to transmit one or more levels of one or more metabolic activities related to an individual. In some embodiments, one or more transmitting units 140 can be used to transmit input related to nutraceutical usage by one or more individuals. In some embodiments, one or more transmitting units 140 can be used to transmit input related to pharmaceutical usage by an individual. In some embodiments, one or more transmitting units 140 can be used to transmit input related to one or more parameters associated with one or more specified goals of an individual. In some embodiments, one or more transmitting units 140 can be used to transmit input related to selection of one or more nutraceuticals. In some embodiments, one or more transmitting units 140 can be used to transmit input related to one or more nutraceuticals that stimulate one or more metabolic pathways related to an individual. In some embodiments, one or more transmitting units 140 can be used to transmit input related to one or more nutraceuticals that inhibit one or more metabolic pathways related to an individual. In some embodiments, one or more transmitting units 140 can be used to transmit input related to selection of at least one vitamin, mineral, enzyme, amino acid, homeopathic supplement, toxin, homeopathic substance, traditional remedy, herbal supplement, glandular supplement, or substantially any combination thereof. In some embodiments, one or more transmitting units 140 can be included within system 100 through use of a hardwired connection. In some embodiments, one or more transmitting units 140 can be included within system 100 through use of a wireless connection. In some embodiments, one or more transmitting units 140 can be included within system 100 through use of a hardwired and a wireless connection.

Signal

The system 100 may include one or more signals. Numerous types of signals may be transmitted. Examples of such signals include, but are not limited to, hardwired signals, wireless signals, infrared signals, optical signals, radiofrequency (RF) signals, audible signals, digital signals, analog signals, or substantially any combination thereof.

Receiving Unit

The system 100 may include one or more receiving units 150. In some embodiments, one or more receiving units 150 may receive one or more signals transmitted in response to intaking information related to one or more parameters related to one or more individuals. In some embodiments, one or more receiving units 150 may receive one or more signals related to one or more metabolic parameters related to an individual. In some embodiments, one or more receiving units 150 may receive one or more signals related to nutraceutical usage of one or more individuals. In some embodiments, one or more receiving units 150 may receive one or more signals related to pharmaceutical usage by one or more individuals. In some embodiments, one or more receiving units 150 may receive input related to one or more goals of an individual. In some embodiments, one or more receiving units 150 may receive input related to selection of one or more nutraceuticals. In some embodiments, one or more receiving units 150 may receive input related to selection of one or more nutraceuticals to increase one or more levels of one or more components associated with an individual. In some embodiments, one or more receiving units 150 may receive input related to selection of one or more nutraceuticals to decrease one or more levels of one or more components associated with an individual. In some embodiments, one or more receiving units 150 may receive input related to selection of one or more nutraceuticals that stimulate one or more metabolic pathways related to an individual. In some embodiments, one or more receiving units 150 may receive input related to selection of one or more nutraceuticals that inhibit one or more metabolic pathways related to an individual. In some embodiments, one or more receiving units 150 may receive input related to selection of at least one vitamin, mineral, enzyme, amino acid, homeopathic supplement, toxin, homeopathic substance, traditional remedy, herbal supplement, glandular supplement, or substantially any combination thereof.

Receiving units 150 may receive input included in numerous types of signals. Examples of such signals include, but are not limited to, hardwired signals, wireless signals, infrared signals, optical signals, radiofrequency (RF) signals, auditory signals, digital signals, analog signals, or substantially any combination thereof.

User Interaction/User

The system 100 may provide for user interaction. In some embodiments, a user 170 may interact with one or more accepting units 110, one or more computational units 120, one or more display units 130, one or more transmitting units 140, one or more receiving units 150, and/or substantially any combination thereof. The user 170 can interact through use of numerous user interfaces 160. For example, a user 170 may interact through use of hardwired methods, such as through use of a keyboard, use of wireless methods, use of the internet, and the like. In some embodiments, a user 170 is a health-care worker. Examples of such health-care workers include, but are not limited to, physicians, nurses, dieticians, pharmacists, and the like. In some embodiments, users 170 may include those persons who work in health-related fields, such as coaches, personal trainers, clerks at food supplement stores, clerks at grocery stores, and the like. In some embodiments, a user 170 is not human. In some embodiments, a user 170 may be an individual. In some embodiments, an individual may be afflicted with a diagnosed condition. For example, in some embodiments, an individual may be afflicted with depression, anemia, obesity, insomnia, lower hormone levels, and the like. In some embodiments, an individual may be afflicted with an undiagnosed condition. In some embodiments, such an undiagnosed condition may be an actual condition or a perceived condition.

Figure 2:
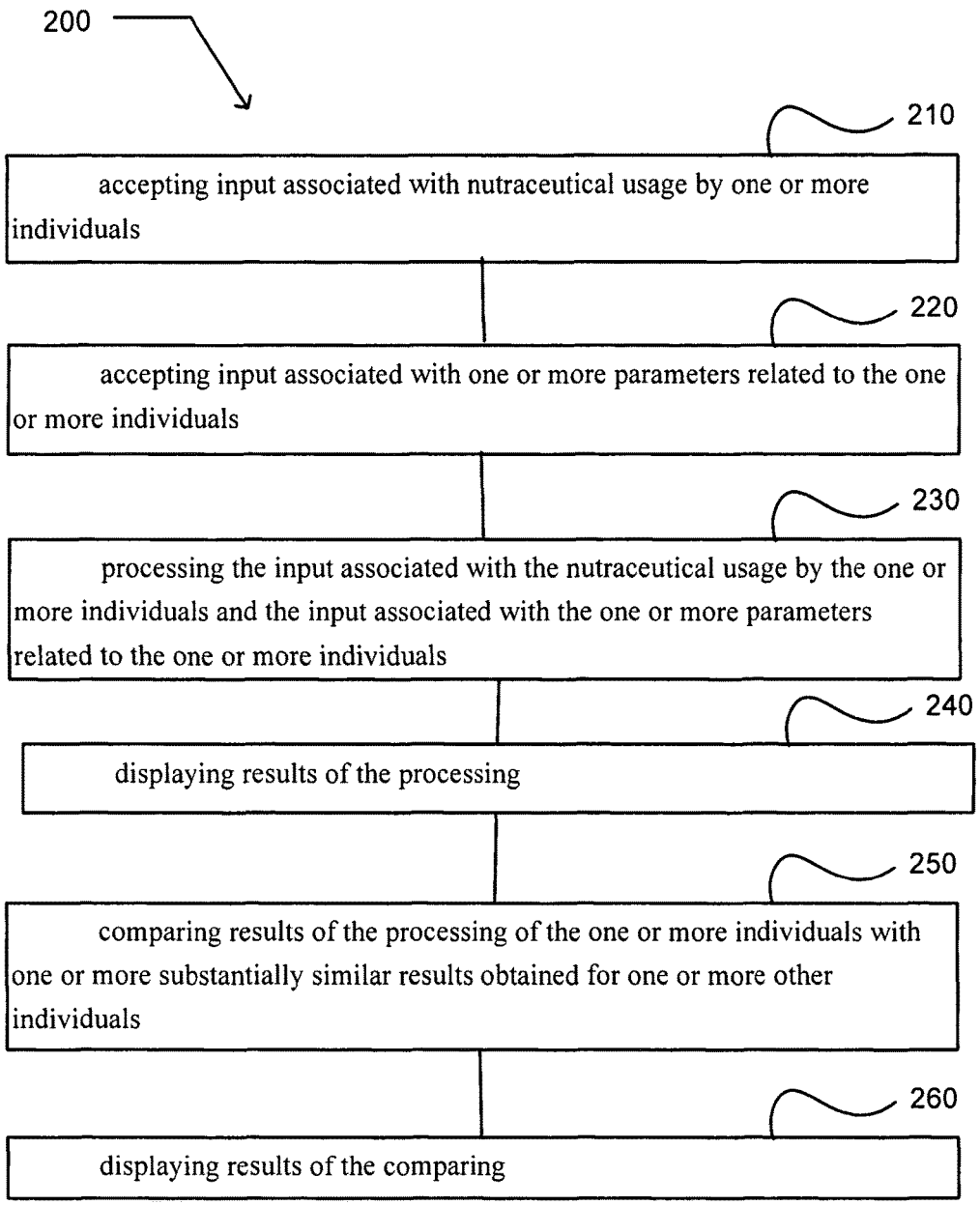
FIG. 2 illustrates an operational flow 200 representing example operations related to processing and displaying input related to one or more nutraceuticals.

FIG. 2 illustrates an operational flow representing examples of operations that are related to the performance of one or more methods related to one or more nutraceuticals. In FIG. 2 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an accepting operation 210 involving accepting input associated with nutraceutical usage by one or more individuals. In some embodiments, the accepting operation 210 may include accepting input associated with the nutraceutical usage by the one or more individuals at two or more times. In some embodiments, the accepting operation 210 may include accepting input associated with one or more concentrations of one or more nutraceuticals used by the one or more individuals. In some embodiments, the accepting operation 210 may include accepting input associated with one or more identities of one or more nutraceuticals used by the one or more individuals. In some embodiments, the accepting operation 210 may include accepting input associated with one or more formulations of one or more nutraceuticals used by the one or more individuals. In some embodiments, the accepting operation 210 may include accepting input associated with one or more times of administration of one or more nutraceuticals used by the one or more individuals. In some embodiments, the accepting operation 210 may include accepting input associated with one or more methods of administration of one or more nutraceuticals used by the one or more individuals. In some embodiments, the accepting operation 210 may include accepting input associated with one or more pharmaceuticals used in conjunction with one or more nutraceuticals used by the one or more individuals.

The operational flow 200 includes an accepting operation 220 involving accepting input associated with one or more parameters related to the one or more individuals. In some embodiments, the accepting operation 220 may include accepting input associated with one or more pharmaceuticals used by the one or more individuals. In some embodiments, the accepting operation 220 may include accepting input associated with the one or more parameters related to the one or more individuals that are determined at two or more times. In some embodiments, the accepting operation 220 may include accepting input related to one or more physical parameters related to the one or more individuals. In some embodiments, the accepting operation 220 may include accepting input related to one or more mental parameters related to the one or more individuals. In some embodiments, the accepting operation 220 may include accepting input related to one or more goals of the one or more individuals. In some embodiments, the accepting operation 220 may include accepting input related to one or more plans of the one or more individuals. In some embodiments, the accepting operation 220 may include accepting input related to one or more metabolic activities related to the one or more individuals. In some embodiments, the accepting operation 220 may include accepting input related to sleep characteristics related to the one or more individuals. In some embodiments, the accepting operation 220 may include accepting input related to exercise characteristics related to the one or more individuals. In some embodiments, the accepting operation 220 may include accepting input related to nutritional characteristics related to the one or more individuals. In some embodiments, the accepting operation 220 may include accepting input related to substance use by the one or more individuals. In some embodiments, the accepting operation 220 may include accepting input related to weight of the one or more individuals. In some embodiments, the accepting operation 220 may include accepting input related to body composition of the one or more individuals. In some embodiments, the accepting operation 220 may include accepting input related to circulatory characteristics of the one or more individuals. In some embodiments, the accepting operation 220 may include accepting input related to mood of the one or more individuals. In some embodiments, the accepting operation 220 may include accepting input related to one or more proteins expressed within the one or more individuals. In some embodiments, the accepting operation 220 may include accepting input related to expression of one or more genes within the one or more individuals.

The operational flow 200 includes a processing operation 230 involving processing the input associated with the nutraceutical usage by the one or more individuals and the input associated with the one or more parameters related to the one or more individuals. In some embodiments, the processing operation 230 may include comparing the input associated with the nutraceutical usage by the one or more individuals to the input associated with the one or more parameters related to the one or more individuals. In some embodiments, the processing operation 230 may include calculating one or more ratios of the input associated with the nutraceutical usage by the one or more individuals to the input associated with the one or more parameters related to the one or more individuals. In some embodiments, the processing operation 230 may include calculating one or more ratios of the input associated with the nutraceutical usage by the one or more individuals to the input associated with the one or more parameters related to the one or more individuals at two or more times. In some embodiments, the processing operation 230 may include determining one or more changes in the nutraceutical usage by the one or more individuals at two or more times. In some embodiments, the processing operation 230 may include determining one or more changes in the one or more parameters related to the one or more individuals. In some embodiments, the processing operation 230 may include comparing one or more changes in the nutraceutical usage by the one or more individuals to one or more changes in the one or more parameters related to the one or more individuals. In some embodiments, the processing operation 230 may include comparing one or more changes in the nutraceutical usage by the one or more individuals to one or more changes in the one or more parameters related to the one or more individuals at two or more times.

The operational flow 200 may include a displaying operation 240 involving displaying results of the processing. In some embodiments, the displaying operation 240 may include displaying the results of the processing on one or more active displays. In some embodiments, the displaying operation 240 may include displaying the results of the processing on one or more passive displays. In some embodiments, the displaying operation 240 may include displaying the results of the processing in numeric format. In some embodiments, the displaying operation 240 may include displaying the results of the processing in graphical format. In some embodiments, the displaying operation 240 may include displaying the results of the processing in audio format. In some embodiments, the displaying operation 240 may include displaying a comparison of one individual with one or more other individuals. In some embodiments, the displaying operation 240 may include displaying one or more changes in the nutraceutical usage by the one or more individuals at two or more times. In some embodiments, the displaying operation 240 may include displaying one or more changes in the one or more parameters related to the one or more individuals at two or more times. In some embodiments, the displaying operation 240 may include displaying one or more changes in the nutraceutical usage by the one or more individuals at two or more times and one or more changes in the parameters related to the one or more individuals at two or more times.

The operational flow 200 may include a comparing operation 250 involving comparing results of the processing of the one or more individuals with one or more substantially similar results obtained for one or more other individuals. In some embodiments, the comparing operation 250 may include comparing one or more values related to the one or more parameters associated with the one or more individuals that are determined at two or more different times to obtain one or more parameter comparisons;

comparing one or more values related to the nutraceutical usage by the one or more individuals at two or more different times to obtain one or more nutraceutical comparisons;

comparing one or more parameter comparisons to the one or more nutraceutical comparisons to obtain one or more parameter-parameter/nutraceutical-nutraceutical comparisons; and comparing the one or more parameter-parameter/nutraceutical-nutraceutical comparisons to the one or more substantially similar results obtained for the one or more other individuals. In some embodiments, the comparing operation 250 may include:

comparing one or more values related to the one or more parameters associated with the one or more individuals that are determined at a first time and one or more values related to the nutraceutical usage by the one or more individuals at the first time to obtain one or more parameter-nutraceutical comparisons;

comparing one or more values related to the one or more parameters associated with the one or more individuals that are determined at a second time and one or more values related to the nutraceutical usage by the one or more individuals at the second time to obtain one or more different parameter-nutraceutical comparisons;

comparing one or more parameter-nutraceutical comparisons to the one or more different parameter-nutraceutical comparisons to obtain one or more parameter-nutraceutical/different parameter-nutraceutical comparisons; and comparing the one or more parameter-nutraceutical/different parameter-nutraceutical comparisons to the one or more substantially similar results obtained for the one or more other individuals.

Figure 3:
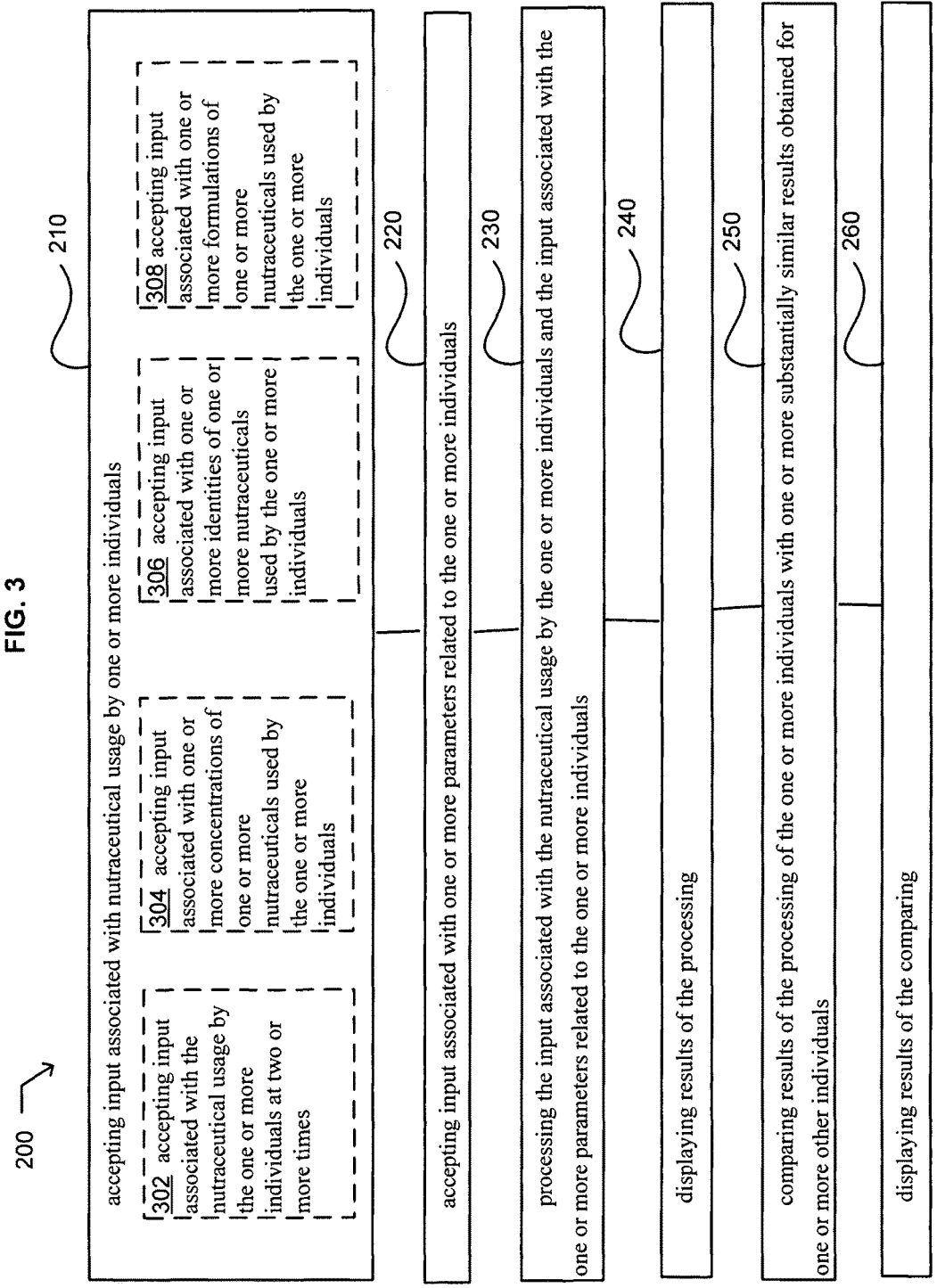
FIG. 3 illustrates alternative embodiments of the example operation flow of FIG. 2.

The operational flow 200 may include a displaying operation 260 involving displaying results of the comparing. In some embodiments the displaying operation 260 may include displaying the results of the comparing on one or more active displays. In some embodiments, the displaying operation 260 may include displaying the results of the comparing on one or more passive displays. In some embodiments, the displaying operation 260 may include displaying the results of the comparing in numeric format. In some embodiments, the displaying operation 260 may include displaying the results of the comparing in graphical format. In some embodiments, the displaying operation 260 may include displaying the results of the comparing in audio format FIG. 3 illustrates alternative embodiments of the example operational flow 200 of FIG. 2. FIG. 3 illustrates example embodiments where the accepting operation 210 may include at least one additional operation. Additional operations may include an operation 302, an operation 304, an operation 306, and/or an operation 308.

At operation 302, the accepting operation 210 may include accepting input associated with the nutraceutical usage by the one or more individuals at two or more times. In some embodiments, one or more accepting units 110 may accept input associated with nutraceutical usage by one or more individuals at two or more times. In some embodiments, one or more accepting units 110 may accept input associated with nutraceutical usage by one or more individuals at one time.

At operation 304, the accepting operation 210 may include accepting input associated with one or more concentrations of one or more nutraceuticals used by the one or more individuals. In some embodiments, one or more accepting units 110 may accept input associated with one or more concentrations of one or more nutraceuticals used by one or more individuals. In some embodiments, one or more accepting units 110 may accept input associated with one or more concentrations of one or more nutraceuticals at the same time. In some embodiments, one or more accepting units 110 may accept input associated with one or more concentrations of one or more nutraceuticals at different times. In some embodiments, one or more accepting units 110 may accept input associated with one or more concentrations of one or more nutraceuticals over a series of time points. In some embodiments, one or more accepting units 110 may accept input associated with one or more concentrations that are expressed as an administered dosage. In some embodiments, one or more accepting units 110 may accept input associated with one or more concentrations of one or more nutraceuticals that are expressed as a systemic concentration of the one or more nutraceuticals within one or more individuals. In some embodiments, one or more accepting units 110 may accept input associated with one or more concentrations of one or more nutraceuticals that are excreted by one or more individuals.

At operation 306, the accepting operation 210 may include accepting input associated with one or more identities of one or more nutraceuticals used by the one or more individuals. In some embodiments, one or more accepting units 110 may accept input associated with one or more identities of one or more nutraceuticals used by one or more individuals. In some embodiments, one or more nutraceuticals may be identified by brand name. In some embodiments, one or more nutraceuticals may be identified by chemical name. In some embodiments, one or more nutraceuticals may be identified by popular name.

At operation 308, the accepting operation 210 may include accepting input associated with one or more formulations of one or more nutraceuticals used by the one or more individuals. In some embodiments, one or more accepting units 110 may accept input associated one or more formulations of one or more nutraceuticals used by the one or more individuals. Examples of such formulations include, but are not limited to, formulations that may be administered orally, transdermally, rectally, vaginally, peritoneally, nasally, and the like. In some embodiments, such formulations may include one or more components. For example, in some embodiments, a formulation may include numerous vitamins, minerals, and the like.

Figure 4:
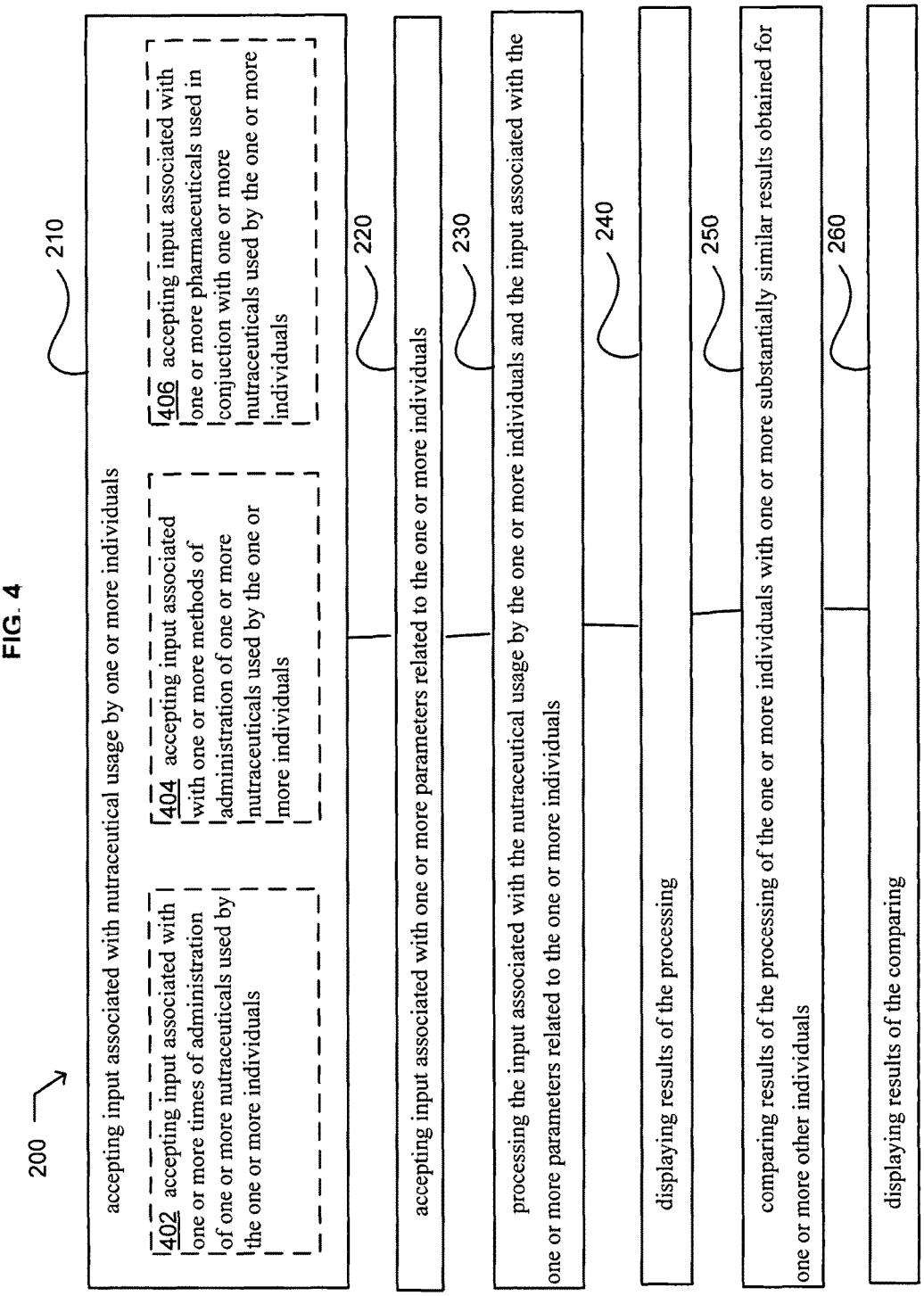
FIG. 4 illustrates alternative embodiments of the example operation flow of FIG. 2.

FIG. 4 illustrates alternative embodiments of the example operational flow 200 of FIG. 2. FIG. 4 illustrates example embodiments where the accepting operation 210 may include at least one additional operation. Additional operations may include an operation 402, an operation 404, and/or an operation 406.

At operation 402, the accepting operation 210 may include accepting input associated with one or more times of administration of one or more nutraceuticals used by the one or more individuals. In some embodiments, one or more accepting units 110 may accept input associated with one or more times of administration of one or more nutraceuticals used by one or more individuals. For example, in some embodiments, one or more accepting units 110 may accept input associated with multiple administrations of one or more nutraceuticals at multiple times. Accordingly, such input may be used to prepare a presentation showing nutraceutical administration relative to time. In some embodiments, additional information may be combined with times of nutraceutical administration. For example, in some embodiments, time of administration may be combined with the identity of one or more nutraceuticals, the concentration of one or more nutraceuticals, the formulation of one or more nutraceuticals, the route of administration of one or more nutraceuticals, parameters associated with one or more individuals, or substantially any combination thereof.

At operation 404, the accepting operation 210 may include accepting input associated with one or more methods of administration of one or more nutraceuticals used by the one or more individuals. In some embodiments, one or more accepting units 110 may accept input associated with one or more methods of administration of one or more nutraceuticals used by one or more individuals. Numerous methods may be used to administer one or more nutraceuticals to one or more individuals. Examples of such methods include, but are not limited to, oral administration, parenteral administration, transdermal administration, nasal administration, sublingual administration, vaginal administration, rectal administration, and the like.

At operation 406, the accepting operation 210 may include accepting input associated with one or more pharmaceuticals used in conjunction with one or more nutraceuticals used by the one or more individuals. In some embodiments, one or more accepting units 110 may accept input associated with one or more pharmaceuticals used in conjunction with one or more nutraceuticals used by one or more individuals. One or more accepting units 110 may accept numerous types of input related to pharmaceuticals. Examples of such input include, but are not limited to, route of administration, time of administration, identity of one or more pharmaceuticals, concentration of one or more pharmaceuticals, interactions of one or more pharmaceuticals with other pharmaceuticals and/or nutraceuticals, mechanism of action utilized by one or more pharmaceuticals, and the like.

Figure 5:
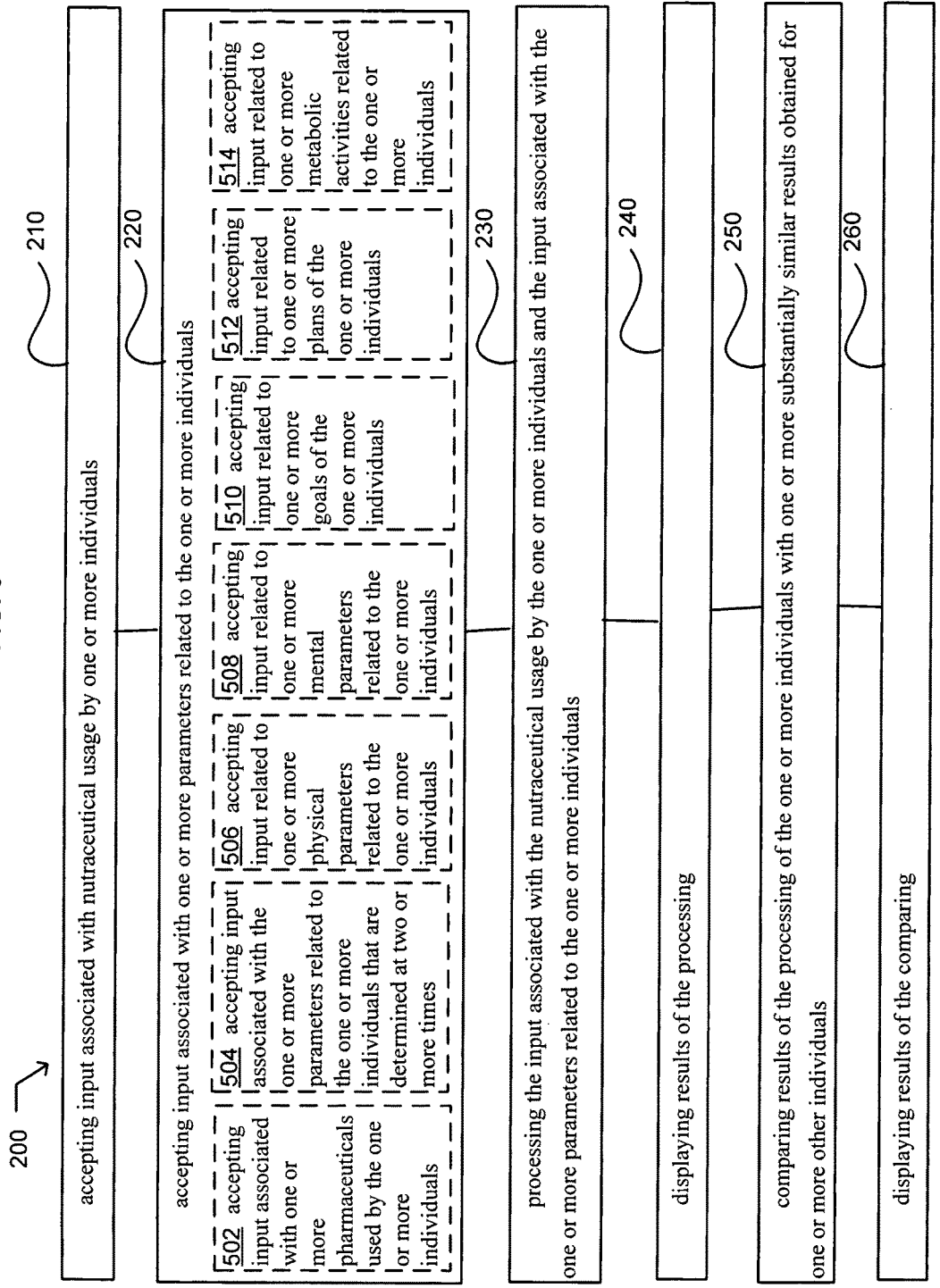
FIG. 5 illustrates alternative embodiments of the example operation flow of FIG. 2.

FIG. 5 illustrates alternative embodiments of the example operational flow 200 of FIG. 2. FIG. 5 illustrates example embodiments where the accepting operation 220 may include at least one additional operation. Additional operations may include an operation 502, an operation 504, an operation 506, an operation 508, an operation 510, an operation 512, and/or an operation 514.

At operation 502, the accepting operation 220 may include accepting input associated with one or more pharmaceuticals used by the one or more individuals. In some embodiments, one or more accepting units 110 may accept input associated with one or more pharmaceuticals used by one or more individuals. In some embodiments, one or more accepting units 110 may accept input associated with the identity of one or more pharmaceuticals. In some embodiments, one or more accepting units 110 may accept input associated with the dosage of one or more pharmaceuticals. In some embodiments, one or more accepting units 110 may accept input associated with contraindications of one or more pharmaceuticals. In some embodiments, one or more accepting units 110 may accept input associated with allergies associated with one or more pharmaceuticals. In some embodiments, one or more accepting units 110 may accept input associated with the duration with which one or more pharmaceuticals are administered. Accordingly, input may include numerous types of information associated with one or more pharmaceuticals.

At operation 504, the accepting operation 220 may include accepting input associated with the one or more parameters related to the one or more individuals that are determined at two or more times. In some embodiments, one or more accepting units 110 may accept input associated with one or more parameters related to one or more individuals that are determined at two or more times. One or more accepting units 110 may accept numerous parameters related to one or more individuals. Examples of such parameters include, but are not limited to, physical parameters (e.g., height, weight, age, body composition, blood pressure, heart rate), mental parameters (e.g., depression, happiness, love, hate, loneliness, hopelessness, joy, acquity, memory, alertness), task related parameters (e.g., physical activity, presentation preparation, work related activity), environment related parameters (e.g., travel, allergens, pathogens), goal related parameters (e.g., lower blood pressure, weight loss, sleep acquisition, sleep avoidance, weight gain, muscle gain, fat loss), and the like. In some embodiments, one or more accepting units 110 may accept input at numerous different times. For example, in some embodiments, one or more accepting units 110 may accept physical parameters, such as an individual's weight or body mass index, at numerous time points. Accordingly, such input may be utilized to track changes in one or more parameters over time.

At operation 506, the accepting operation 220 may include accepting input related to one or more physical parameters related to the one or more individuals. In some embodiments, one or more accepting units 110 may accept input related to one or more physical parameters related to one or more individuals. One or more accepting units 110 may accept numerous physical parameters. Examples of such physical parameters may include, but are not limited to, height, weight, age, health, disease, physical state, injury, dental health, health history, family health history, and the like.

At operation 508, the accepting operation 220 may include accepting input related to one or more mental parameters related to the one or more individuals. In some embodiments, one or more accepting units 110 may accept input related to one or more mental parameters related to one or more individuals. One or more accepting units 110 may accept numerous mental parameters. Examples of such mental parameters may include, but are not limited to, mood (e.g., happiness, sadness, elation, depression, love, hate, loneliness, hopelessness), mental health (e.g., bipolar disorder, schizophrenia, multiple personality disorder, obsessive compulsive disorder, Alzheimer's disease), mental health history, family mental health history, mental function (e.g., alertness, acquity), and the like.

At operation 510, the accepting operation 220 may include accepting input related to one or more goals of the one or more individuals. In some embodiments, one or more accepting units 110 may accept input related to one or more goals of one or more individuals. One or more accepting units 110 may accept numerous goal related parameters. Examples of such goal related parameters may include, but are not limited to, athletic performance (e.g., weight gain, weight loss, muscle gain, fat loss, decreased body mass index, endurance, strength), mental performance (e.g., alertness, memory, acuity), and the like.

At operation 512, the accepting operation 220 may include accepting input related to one or more plans of the one or more individuals. In some embodiments, one or more accepting units 110 may accept input related to one or more plans of one or more individuals. In some embodiments, one or more accepting units 110 may accept input related to the travel plans of one or more individuals. In some embodiments, one or more accepting units 110 may accept input related to the work plans of one or more individuals. In some embodiments, one or more accepting units 110 may accept input related to the exercise plans of one or more individuals. Accordingly, one or more accepting units 110 may accept input that includes numerous types of information related to the plans of one or more individuals.

At operation 514, the accepting operation 220 may include accepting input related to one or more metabolic activities related to the one or more individuals. In some embodiments, one or more accepting units 110 may accept input related to one or more metabolic activities related to one or more individuals. One or more accepting units 110 may accept input related to numerous types of metabolic activity. Examples of input related to metabolic activities include, but are not limited to, respiration rate, enzyme activity, oxygen consumption, heart rate, digestion, fatty acid-oxidation, hormone activity, vasodilation, vasoconstriction, pH, carbon dioxide concentration (e.g., blood, expired), oxygen concentrations (e.g., blood, expired), catabolic reactions, anabolic reactions, lipid metabolism, sugar metabolism, and the like.

Figure 6:
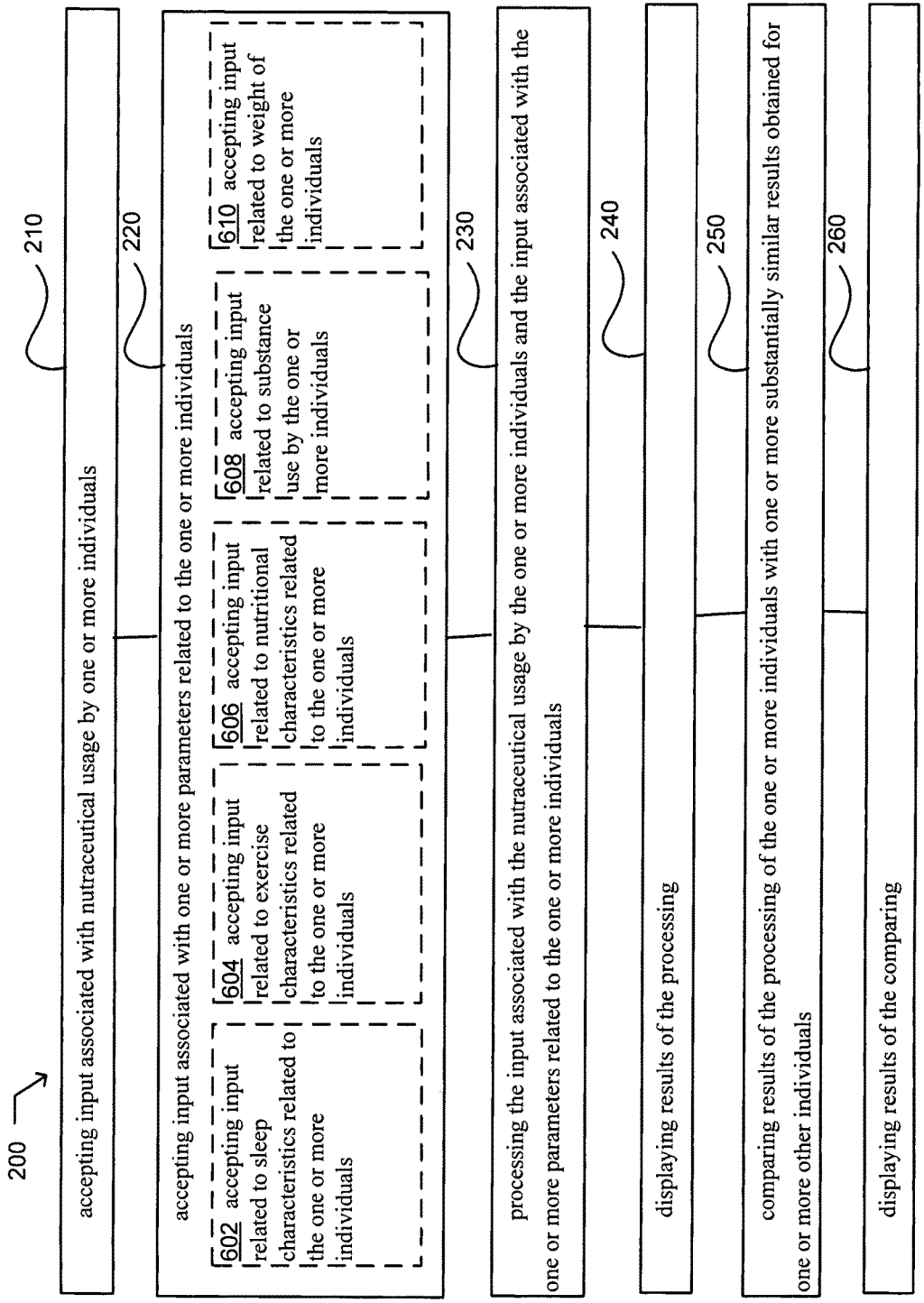
FIG. 6 illustrates alternative embodiments of the example operation flow of FIG. 2.

FIG. 6 illustrates alternative embodiments of the example operational flow 200 of FIG. 2. FIG. 6 illustrates example embodiments where the accepting operation 220 may include at least one additional operation. Additional operations may include an operation 602, an operation 604, an operation 606, an operation 608, and/or an operation 610.

At operation 602, the accepting operation 220 may include accepting input related to sleep characteristics related to the one or more individuals. In some embodiments, one or more accepting units 110 may accept input related to sleep characteristics related to one or more individuals. In some embodiments, one or more input units may accept input related to the number of hours that one or more individuals sleep during a time period. In some embodiments, one or more input units may accept input related to times when one or more individuals sleep during a time period. In some embodiments, one or more input units may accept input related to the sleep schedules of one or more individuals. In some embodiments, one or more input units may accept input related to the quality of sleep obtained by one or more individuals. In some embodiments, one or more input units may accept input related to alertness felt by one or more individuals. In some embodiments, one or more input units may accept input related to sleep characteristics. For example, such input may include information related to positive and/or negative sleep experience, tiredness, restlessness, insomnia, alertness, feelings of tiredness, and the like. Accordingly, one or more input units may accept numerous types of input related to the sleep characteristics of one or more individuals.

At operation 604, the accepting operation 220 may include accepting input related to exercise characteristics related to the one or more individuals. In some embodiments, one or more accepting units 110 may accept input related to exercise characteristics related to one or more individuals. Input related to exercise characteristics may include, but is not limited to, type of exercise, duration of exercise, intensity of exercise, frequency of exercise, physiological parameters (e.g., pulse, blood pressure, oxygen consumption, carbon dioxide production) occurring during exercise, and the like.

At operation 606, the accepting operation 220 may include accepting input related to nutritional characteristics related to the one or more individuals. In some embodiments, one or more accepting units 110 may accept input related to nutritional characteristics related to one or more individuals. Input related to nutritional characteristics may include, but is not limited to, types of food consumed (e.g., functional foods), types of beverages consumed, number of calories consumed, composition of consumed items (e.g., fat content, cholesterol content, oil content, caloric content), times of consumption, and the like.

At operation 608, the accepting operation 220 may include accepting input related to substance use by the one or more individuals. In some embodiments, one or more accepting units 110 may accept input related to substance use by the one or more individuals. Examples of such input include, but are not limited to, alcohol use, tobacco use, nicotine intake, pharmaceutical use, illicit drug use, food supplement use, nutraceutical use, and the like.

At operation 610, the accepting operation 220 may include accepting input related to weight of the one or more individuals. In some embodiments, one or more accepting units 110 may accept input related to weight of one or more individuals. One or more accepting units 110 may accept input related to present weight, past weight, future weight goals, or substantially any combination thereof.

Figure 7:
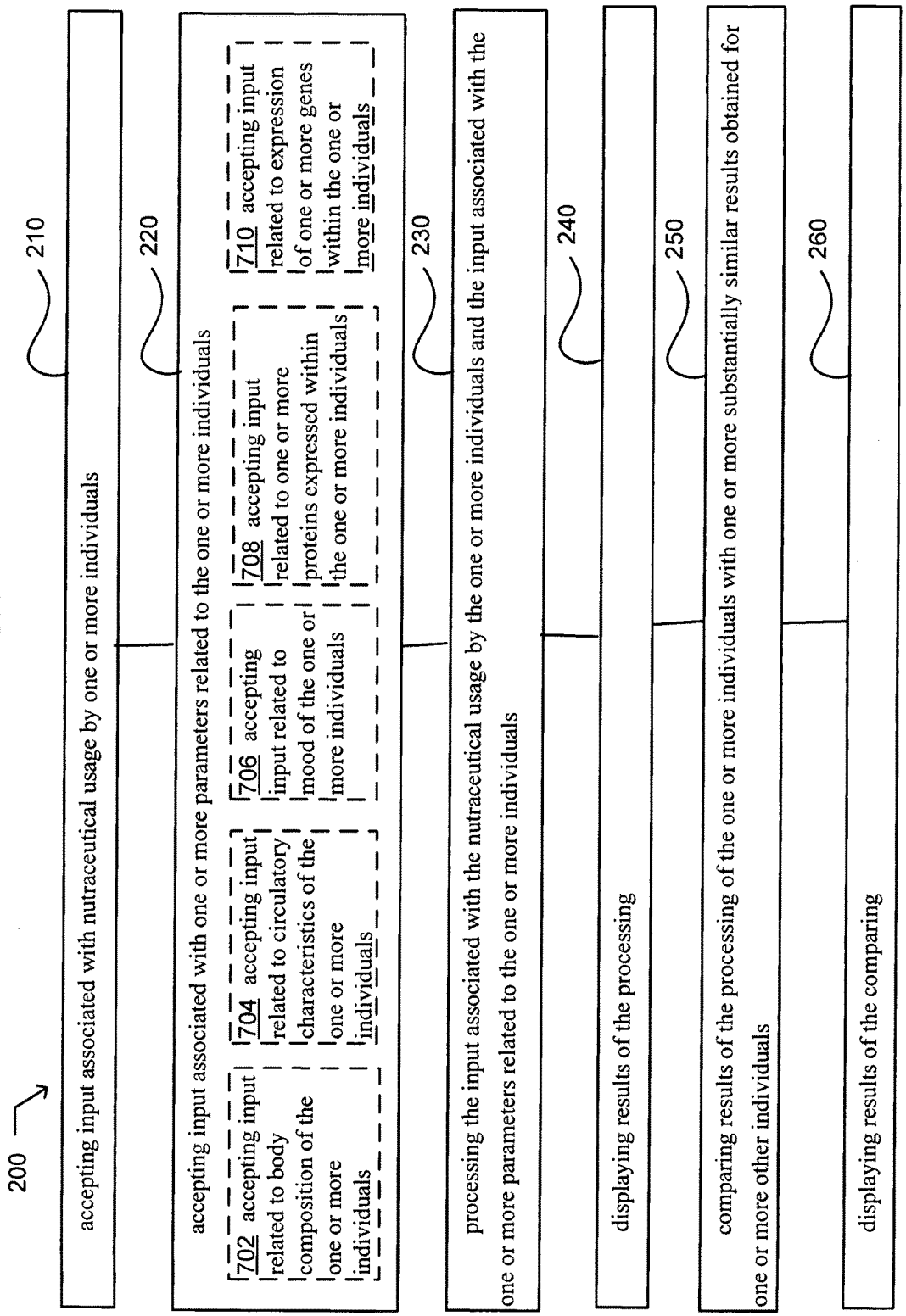
FIG. 7 illustrates alternative embodiments of the example operation flow of FIG. 2.

FIG. 7 illustrates alternative embodiments of the example operational flow 200 of FIG. 2. FIG. 7 illustrates example embodiments where the accepting operation 220 may include at least one additional operation. Additional operations may include an operation 702, an operation 704, an operation 706, an operation 708, and/or an operation 710.

At operation 702, the accepting operation 220 may include accepting input related to body composition of the one or more individuals. In some embodiments, one or more accepting units 110 may accept input related to body composition of one or more individuals. The results from numerous body composition tests may be accepted by one or more accepting units 110. Examples of such tests include, but are not limited to, skinfold measurement, body mass index, waist to hip ratio, hydrostatic weighing, bioelectric impedance, dual-energy X-ray absorptiometry, near infrared interactance, total body potassium, whole-body air-displacement plethysmography, magnetic resonance imaging, total body electrical conductivity, computed tomography, total body protein, or substantially any combination thereof.

At operation 704, the accepting operation 220 may include accepting input related to circulatory characteristics of the one or more individuals. In some embodiments, one or more accepting units 110 may accept input related to circulatory characteristics of one or more individuals. One or more accepting units 110 may accept input related to numerous types of circulatory characteristics. Examples of such circulatory characteristics include, but are not limited to, blood pressure, hypertension, heart rate, vasoelasticity, cholesterol levels, coronary heart disease, atherosclerosis, and the like.

At operation 706, the accepting operation 220 may include accepting input related to mood of the one or more individuals. In some embodiments, one or more accepting units 110 may accept input related to the mood of one or more individuals. Examples of various moods that may be input include, but are not limited to, happiness, sadness, loneliness, confusion, forgetfulness, joy, glee, euphoria, hopelessness, anger, rage, love, contempt, hate, frustration, and the like.

At operation 708, the accepting operation 220 may include accepting input related to one or more proteins expressed within the one or more individuals. In some embodiments, one or more accepting units 110 may accept input related to one or more proteins expressed within one or more individuals. For example, the enzyme 5,10-methylenetetrahydrofolate reductase catalyzes the conversion of 5,10-methylenetetrahydrofolate, required for purine and thymidine syntheses, to 5-methyltetrahydrofolate, the primary circulatory form of folate necessary for methionine synthesis. A common mutation (677C→T) in 5,10-methylenetetrahydrofolate reductase reduces enzyme activity, leading to lower levels of 5-methyltetrahydrofolate. It has been determined that men having adequate folate levels who are homozygous for the mutation (677T/677T) exhibit a three-fold decrease in risk of colorectal cancer when compared to men having adequate folate levels who are homozygous normal (677C/677C) or heterozygous (677C/677T). However, the protection due to the mutation was absent in men with folate deficiency. In men with the homozygous normal genotype who drink little or no alcohol as reference, men with the homozygous mutation who drink little or no alcohol have an eight-fold decrease in risk and moderate drinkers exhibit a two-fold reduction in risk (Ma et al., Cancer Research, 57:1098-1102 (1997)). Polymorphisms in genes involved in folate metabolism have also been linked to maternal risk factors for Down Syndrome, neural tube defects, and oral clefts (Mills et al., Am. J. Med. Genet., 86:71-74 (1999); Wilson et al., Mol. Genet. Metab., 67:317-323 (1999); Hobbs et al., Am. J. Med. Genet., 67:623-630 (2000)). Accordingly, in some embodiments, information related to production of one or more proteins within an individual may be input. Such information may be used during the selection of nutraceuticals for administration to an individual. Such information may also be used to suggest health-related information. In some embodiments, one or more accepting units 110 may accept input related to the concentration of one or more proteins expressed within an individual. In some embodiments, one or more accepting units 110 may accept input related to the activity of one or more proteins expressed within an individual. Accordingly, one or more accepting units 110 may accept information related to numerous proteins and properties of proteins expressed within an individual.

At operation 710, the accepting operation 220 may include accepting input related to expression of one or more genes within the one or more individuals. In some embodiments, one or more accepting units 110 may accept input related to expression of one or more genes within one or more individuals. In some embodiments, such information may be used during the selection of nutraceuticals for administration to an individual. Such information may also be used to suggest health-related information. For example, folate status and common variations in genes that code for folate dependent enzymes are linked to many types of cancer, vascular disease, birth defects, and complications of pregnancy. This arises because several molecular mechanisms that underpin the genomic machinery are sensitive to B vitamin status and, in particular, are responsive to the interaction between folate nutrition and folate dependent enzyme polymorphisms (Lucock, B M J, 328:211-214 (2004)). Accordingly, genetic information may be utilized during the selection of one or more nutraceuticals for administration to an individual. In another example, black tea polyphenols (e.g., a theaflavin-3-monogallate and theaflavin-3'-monogallate mixture) have been shown to suppress cyclooxygenase 2 (Cox-2) gene expression at both the messenger ribonucleic acid and protein level (Lu et al., Cancer Reserch, 60:6465-6471 (2000)). Pharmacological inhibition of COX can provide relief from the symptoms of inflammation and pain. Accordingly, in some embodiments, input related to COX gene expression may be accepted by one or more accepting units 110 to follow nutraceutical mediated inhibition of COX expression. Black tea extracts also exhibit chemoprotective activity (Lu et al., Cancer Reserch, 60:6465-6471 (2000)). In another example, a resveratrol analog (3,4,5,4'-tetrahydroxystilbene) has been shown to differentially induce pro-apoptotic p53/Bax gene expression and inhibit the growth of transformed cells but not their normal counterparts (Lu et al., Carcinogenesis, 22:321-328 (2001)). Accordingly, p53/Bax gene expression may be input to follow resveratrol analog mediated induction of gene expression. Numerous nutraceuticals mediate induction or inhibition of gene expression (e.g., Chen et al., Cancer Letters, 129:173-179 (1998); British J. Cancer, 92:513-521 (2005)). In another example, dietary omega-3 polyunsaturated fatty acids were shown to affect brain gene expression (Kitajka et al., PNAS, 101:10931-10936 (2004)). In some embodiments, one or more accepting units 110 may accept input related to the expression level of one or more genes within an individual. In some embodiments, one or more accepting units 110 may accept input related to the activity of one or more gene products expressed within an individual. Accordingly, one or more accepting units 110 may accept information related to numerous genes and the products of gene expression within an individual.

Figure 8:
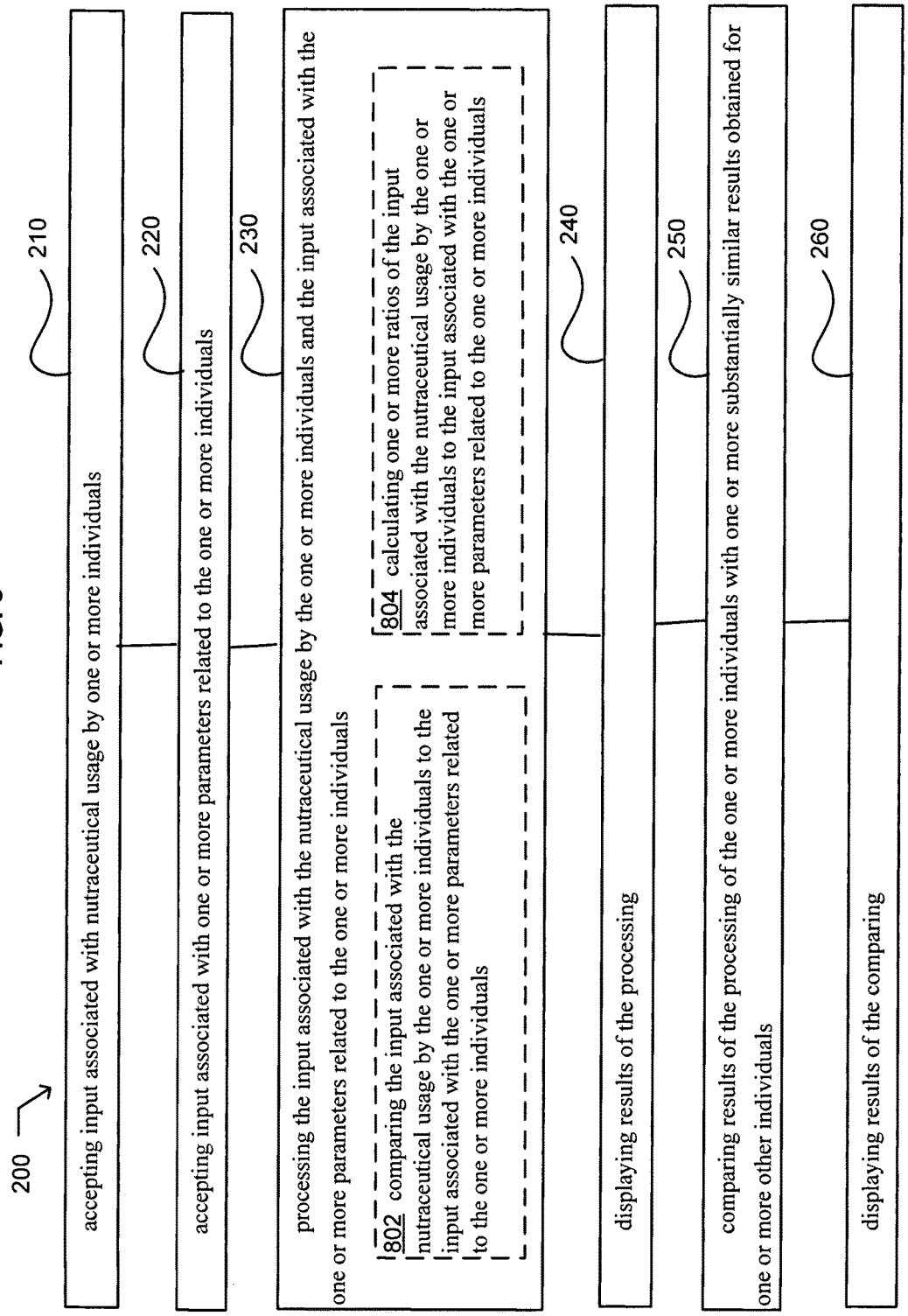
FIG. 8 illustrates alternative embodiments of the example operation flow of FIG. 2.

FIG. 8 illustrates alternative embodiments of the example operational flow 200 of FIG. 2. FIG. 8 illustrates example embodiments where the processing operation 230 may include at least one additional operation. Additional operations may include an operation 802, and/or an operation 804.

At operation 802, the processing operation 230 may include comparing the input associated with the nutraceutical usage by the one or more individuals to the input associated with the one or more parameters related to the one or more individuals. In some embodiments, one or more computational units 120 may compare input associated with nutraceutical usage by one or more individuals to input associated with one or more parameters related to the one or more individuals. One or more computational units 120 may compare numerous types of input associated with nutraceutical usage and numerous types of input associated with parameters related to one or more individuals. For example, in some embodiments, serotonin usage may be compared with the amount of sleep obtained by an individual. In some embodiments, caffeine usage may be compared with the amount of sleep obtained by an individual. In some embodiments, 5-hydroxytryptophan usage may be compared to the mood of an individual. In some embodiments, lithium usage may be compared to suppression of antipsychotic symptoms. In some embodiments, one or more computational units 120 may compare numerous types of input associated with nutraceutical usage and numerous types of input associated with parameters related to one individual. In some embodiments, one or more computational units 120 may compare numerous types of input associated with nutraceutical usage and numerous types of input associated with parameters related to more than one individual. In some embodiments, one or more computational units 120 may compare numerous types of input associated with nutraceutical usage and numerous types of input associated with parameters related to one individual to one or more other individuals. For example, in some embodiments, nutraceutical usage and parameters associated with an individual may be compared to nutraceutical usage and parameters associated with one or more other individuals.

At operation 804, the processing operation 230 may include calculating one or more ratios of the input associated with the nutraceutical usage by the one or more individuals to the input associated with the one or more parameters related to the one or more individuals. In some embodiments, one or more computational units 120 may calculate one or more ratios of input associated with nutraceutical usage by one or more individuals to input associated with one or more parameters related to the one or more individuals. For example, in some embodiments, one or more computational units 120 may calculate the ratio of nutraceutical dosage (e.g., hoodia) to a determined parameter (e.g., weight loss) at one or more given times. In such instances, the individual ratios could be plotted over time to determine if there was a correlation of nutraceutical usage and the parameter (e.g., weight loss). In some embodiments, such ratios related to an individual could be compared to substantially similar ratios related to other individuals. Such a comparison would allow an individual to compare themselves to other individuals. Numerous different types of nutraceutical usages and parameters may be used during the calculation of ratios.

Figure 9:
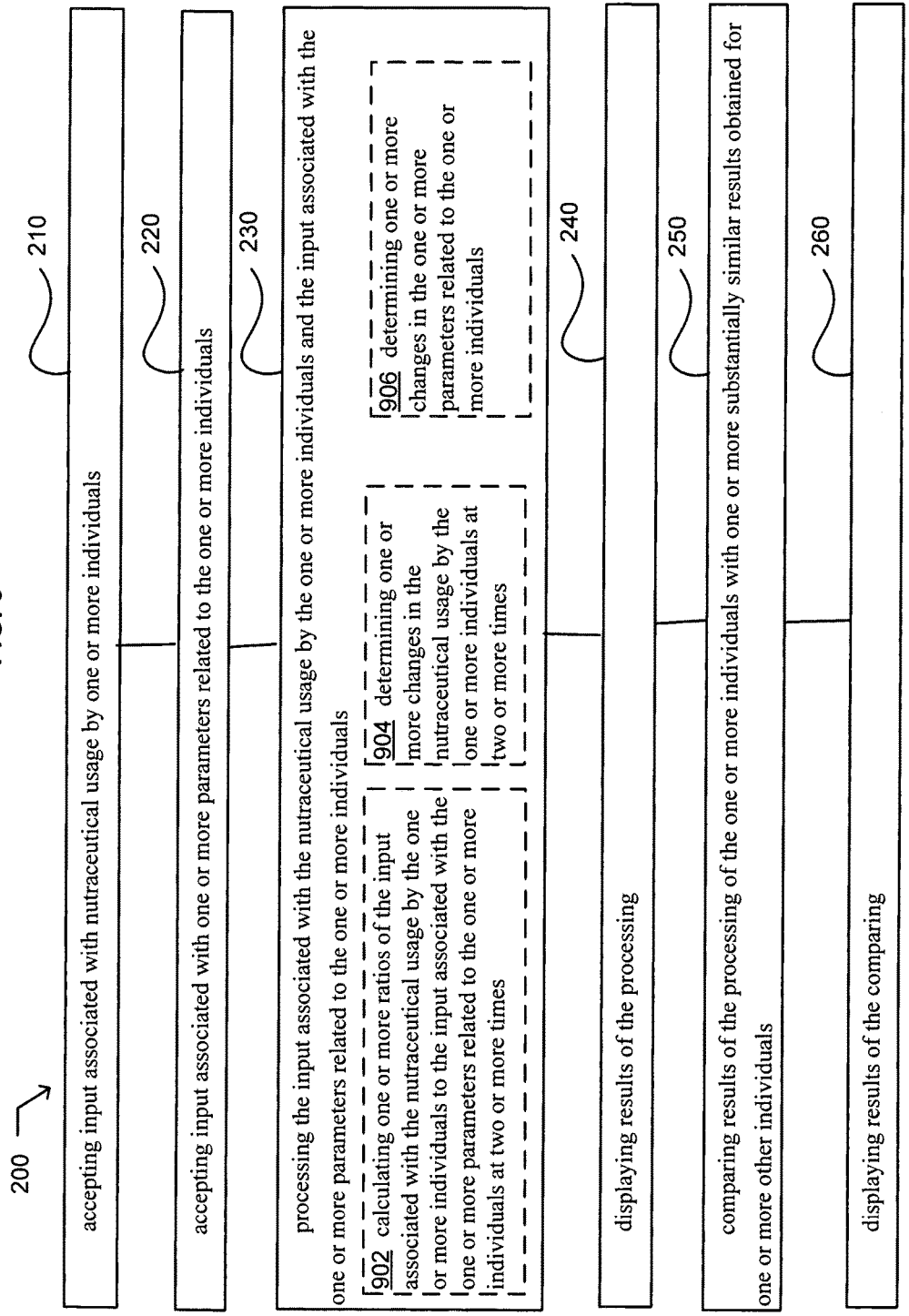
FIG. 9 illustrates alternative embodiments of the example operation flow of FIG. 2.

FIG. 9 illustrates alternative embodiments of the example operational flow 200 of FIG. 2. FIG. 9 illustrates example embodiments where the processing operation 230 may include at least one additional operation. Additional operations may include an operation 902, an operation 904, and/or an operation 906.

At operation 902, the processing operation 230 may include calculating one or more ratios of the input associated with the nutraceutical usage by the one or more individuals to the input associated with the one or more parameters related to the one or more individuals at two or more times. In some embodiments, one or more computational units 120 may calculate one or more ratios of input associated with nutraceutical usage by one or more individuals to input associated with one or more parameters related to the one or more individuals at two or more times. In some embodiments, the ratio of nutraceutical usage and one or more parameters can be compared at two or more times to determine if nutraceutical usage affects the one or more parameters. In some embodiments, the ratio of nutraceutical usage and one or more parameters can be compared at two or more times to titrate the dosage of the one or more nutraceuticals relative to one or more parameters. In some embodiments, the ratio of nutraceutical usage and one or more parameters can be compared at two or more times to determine if nutraceutical usage affects the one or more parameters. In some embodiments, one or more ratios related to one individual may be compared to substantially similar ratios related to one or more other individuals.

At operation 904, the processing operation 230 may include determining one or more changes in the nutraceutical usage by the one or more individuals at two or more times. In some embodiments, one or more computational units 120 may determine one or more changes in nutraceutical usage by one or more individuals at two or more times. For example, in some embodiments, an individual may change the dosage of one or more nutraceuticals. In some embodiments, an individual may change the identity of one or more nutraceuticals. In some embodiments, an individual may change the route of administration of one or more nutraceuticals. In some embodiments, an individual may change the time of administration of one or more nutraceuticals. Accordingly, in some embodiments, one or more computational units 120 may determine one or more changes in nutraceutical usage and correlate the change in nutraceutical usage with one or more changes in one or more parameters related to one or more individuals. For example, in some embodiments, changes in serotonin usage (e.g., dosage, time of administration) may be correlated with sleep acquisition by an individual. In some embodiments, changes in 5-hydroxytryptophan usage may be correlated to with the mood of an individual. Numerous changes in nutraceutical usage may be determined and correlated to one or more parameters related to an individual.

At operation 906, the processing operation 230 may include determining one or more changes in the one or more parameters related to the one or more individuals. In some embodiments, one or more computational units 120 may determine one or more changes in one or more parameters related to one or more individuals. Examples of parameters that may change include, but are not limited to, physical parameters, mental parameters, physiological parameters, and the like. In some embodiments, changes in one or more parameters may be correlated to nutraceutical usage by an individual. In some embodiments, changes in one or more parameters may be correlated to changes in nutraceutical usage by an individual.

Figure 10:
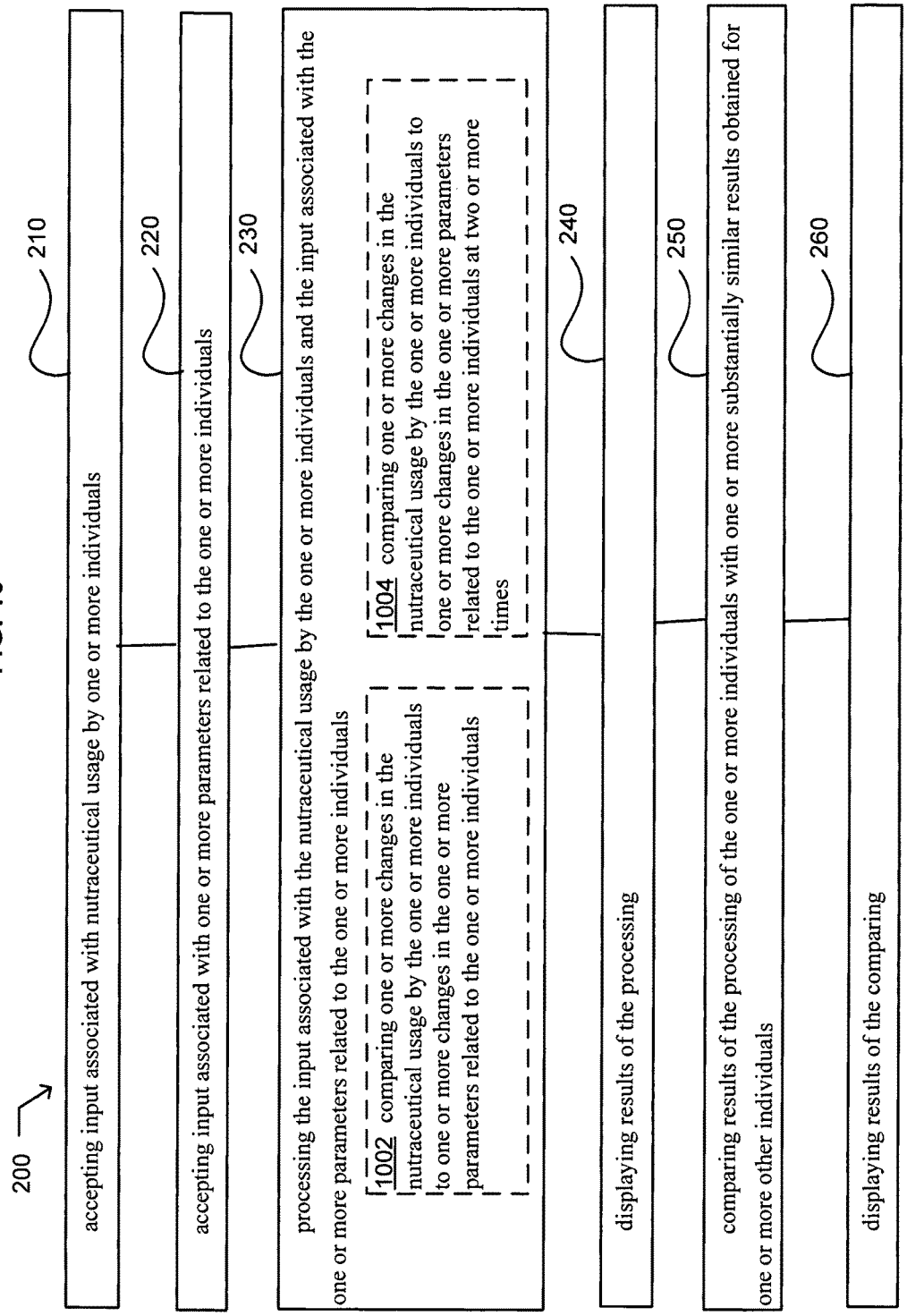
FIG. 10 illustrates alternative embodiments of the example operation flow of FIG. 2.

FIG. 10 illustrates alternative embodiments of the example operational flow 200 of FIG. 2. FIG. 10 illustrates example embodiments where the processing operation 230 may include at least one additional operation. Additional operations may include an operation 1002, and/or an operation 1004.

At operation 1002, the processing operation 230 may include comparing one or more changes in the nutraceutical usage by the one or more individuals to one or more changes in the one or more parameters related to the one or more individuals. In some embodiments, one or more computational units 120 may compare one or more changes in nutraceutical usage by one or more individuals to one or more changes in one or more parameters related to the one or more individuals. Numerous changes in nutraceutical usage may be compared. Examples of such changes in nutraceutical usage include, but are not limited to, dosage, time of administration, route of administration, formulation, manufacturer, and the like. Numerous changes in parameters may be compared. Examples of such changes in parameters include, but are not limited to, mental parameters, physical parameters, social parameters, sleep parameters, and the like. In some embodiments, one or more changes in nutraceutical usage by an individual may be compared to changes in one or more parameters related to the individual. In some embodiments, one or more changes in nutraceutical usage by an individual may be compared to changes in one or more parameters related to one or more other individuals. For example, in some embodiments, an individual may determine how a change in their personal nutraceutical usage changes one or more parameters when compared to a substantially similar change by one or more other individuals. In some embodiments, one or more computational units 120 may compare the nutraceutical usage by an individual to one or more changes in one or more parameters related to the individual and also to substantially similar changes in one or more other individuals to suggest a course of nutraceutical usage for the individual. For example, in some embodiments, the computational unit 120 may suggest a higher dosage of one or more nutraceuticals for administration to an individual if it is determined that a higher dosage will produce an effect based on changes resulting in one or more other individuals. Numerous comparisons may be made by one or more computational units 120.

At operation 1004, the processing operation 230 may include comparing one or more changes in the nutraceutical usage by the one or more individuals to one or more changes in the one or more parameters related to the one or more individuals at two or more times. In some embodiments, one or more computational units 120 may compare one or more changes in nutraceutical usage by one or more individuals to one or more changes in one or more parameters related to one or more individuals at two or more times. Numerous changes in nutraceutical usage may be compared. Examples of such changes in nutraceutical usage include, but are not limited to, dosage, time of administration, route of administration, formulation, manufacturer, and the like. Numerous changes in parameters may be compared. Examples of such changes in parameters include, but are not limited to, mental parameters, physical parameters, social parameters, sleep parameters, and the like.

Figure 11:
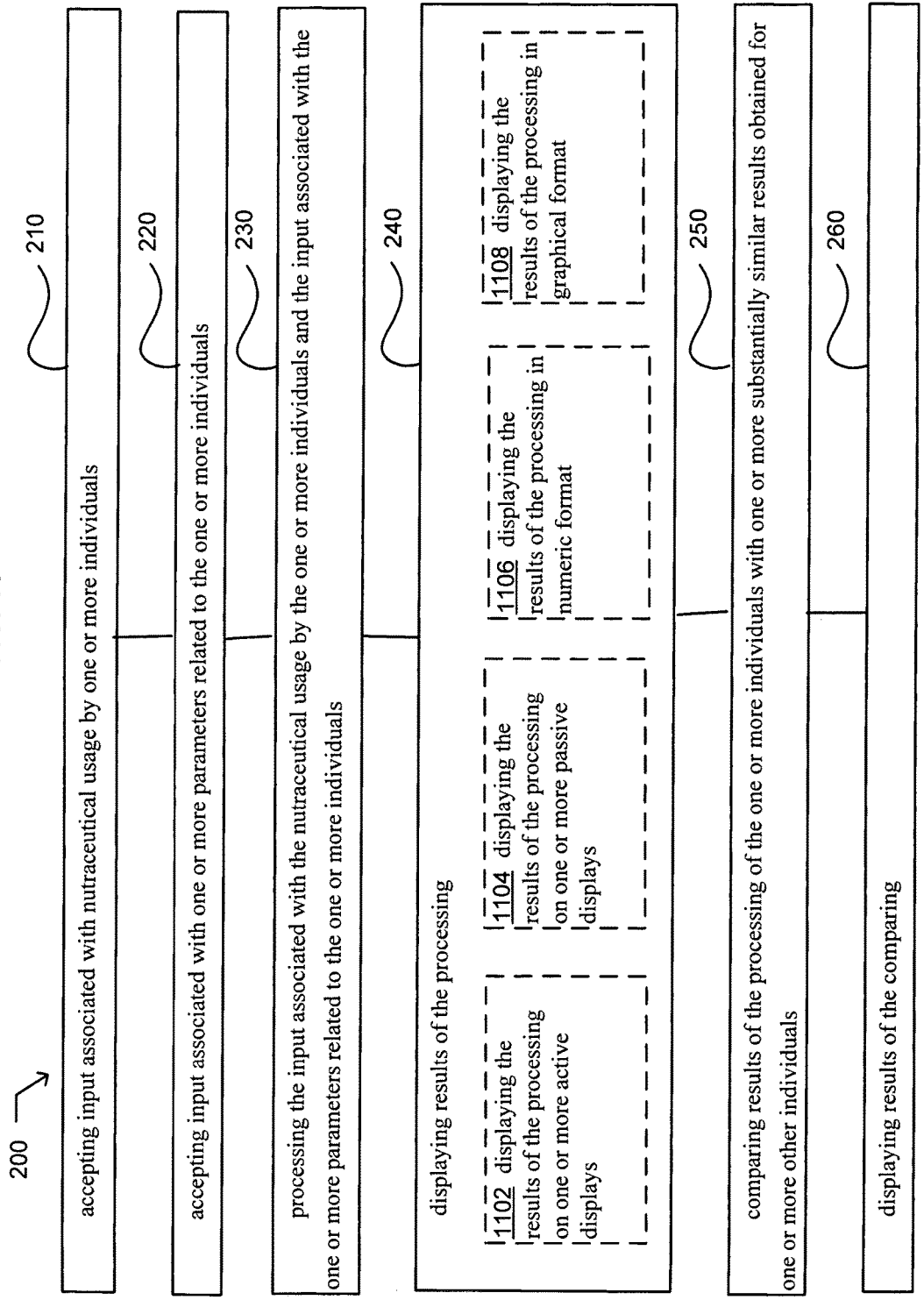
FIG. 11 illustrates alternative embodiments of the example operation flow of FIG. 2.

FIG. 11 illustrates alternative embodiments of the example operational flow 200 of FIG. 2. FIG. 11 illustrates example embodiments where the displaying operation 240 may include at least one additional operation. Additional operations may include an operation 1102, an operation 1104, an operation 1106, and/or an operation 1108.

At operation 1102, the displaying operation 240 may include displaying the results of the processing on one or more active displays. In some embodiments, one or more display units 130 may display results of processing on one or more active displays. Numerous active display units 130 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At operation 1104, the displaying operation 240 may include displaying the results of the processing on one or more passive displays. In some embodiments, one or more display units 130 may display results of processing on one or more passive displays. In some embodiments, one or display units 130 may include one or more liquid crystal displays (LCD). Methods to construct passive displays have been described (e.g., U.S. Pat. Nos. 4,807,967; 4,729,636, 4,436,378; 4,257,041; herein incorporated by reference).

At operation 1106, the displaying operation 240 may include displaying the results of the processing in numeric format. In some embodiments, one or more display units 130 may display results of processing in numeric format.

At operation 1108, the displaying operation 240 may include displaying the results of the processing in graphical format. In some embodiments, one or more display units 130 may display results of processing in graphical format. Numerous types of graphical formats may be used. Examples of such graphical formats include, but are not limited to, use of shapes, use of colors, use of symbols (e.g., smiley face, frowny face, thumbs up sign, thumbs down sign, histograms, bar graphs, pie charts, and the like).

Figure 12:
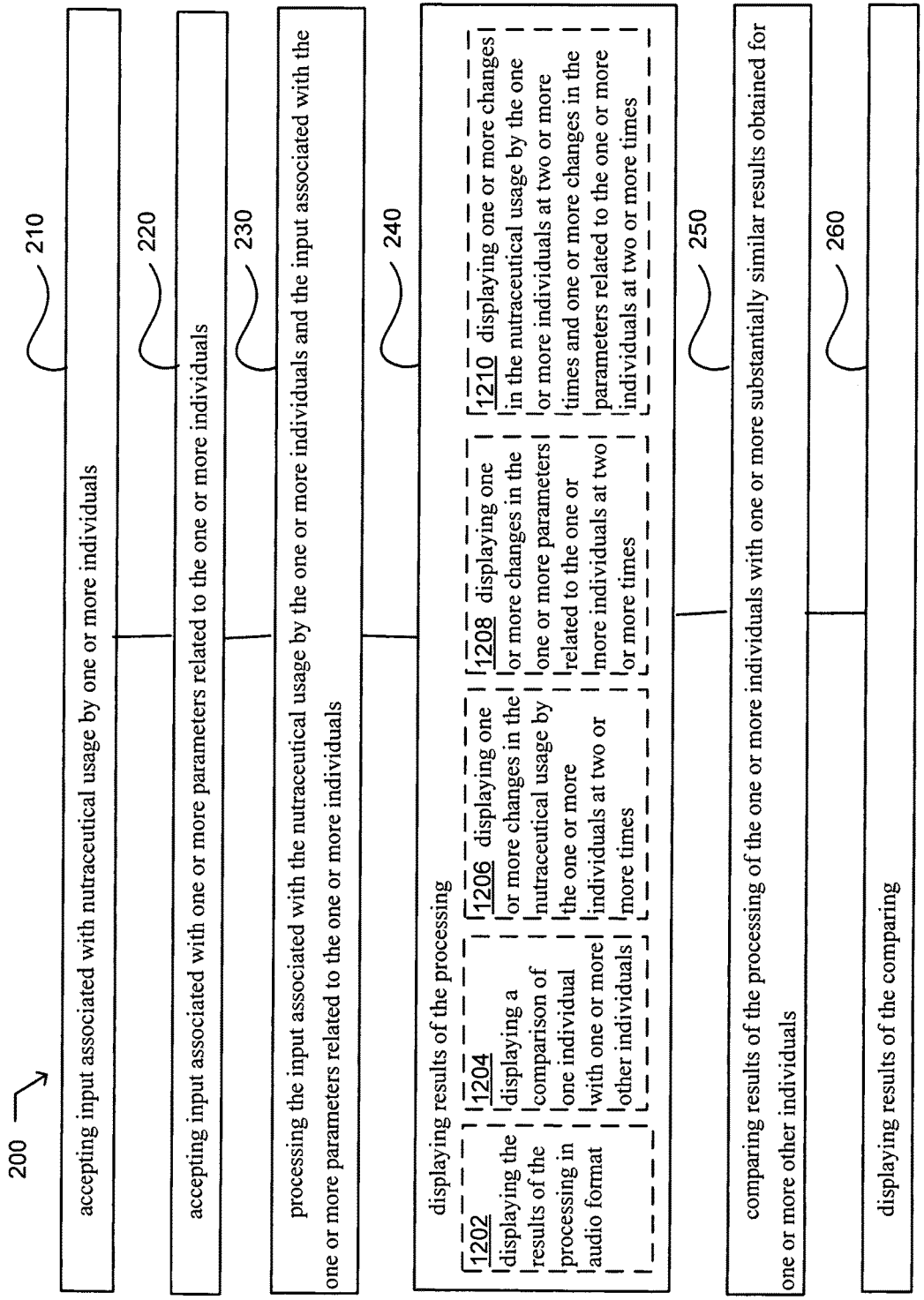
FIG. 12 illustrates alternative embodiments of the example operation flow of FIG. 2.

FIG. 12 illustrates alternative embodiments of the example operational flow 200 of FIG. 2. FIG. 12 illustrates example embodiments where the displaying operation 240 may include at least one additional operation. Additional operations may include an operation 1202, an operation 1204, an operation 1206, an operation 1208, and/or an operation 1210.

At operation 1202, the displaying operation 240 may include displaying the results of the processing in audio format. In some embodiments, one or more display units 130 may display results of processing in audio format. In some embodiments, the results of processing may be presented in voice format. For example, in some embodiments, a voice may tell an individual to increase, decrease, or maintain one or more dosages of one or more nutraceuticals. In some embodiments, sounds may be used to indicate changes in nutraceutical usage and/or parameters related to an individual. In some embodiments, applause, cheering, and the like may be used to indicate a positive change. Examples of positive changes include, but are not limited to, weight loss, lowered blood pressure, lowered heart rate, and the like. In some embodiments, booing, hissing, nagging, and the like may be used to indicate a negative change. Examples of negative changes include, but are not limited to, weight gain, increased blood pressure, increased heart rate, and the like.

At operation 1204, the displaying operation 240 may include displaying a comparison of one individual with one or more other individuals. In some embodiments, one or more display units 130 may display a comparison of one individual with one or more other individuals. Numerous display formats may be used. In some embodiments, one or more runners may be depicted on a visual display as participating in a race such that an individual will be depicted according to their position in the race. For example, if an individual is leading a group in weight loss, they may be depicted as running in first place in a foot race. However, if the individual is behind a group in weight loss, they may be depicted as running in last place in a foot race. In some embodiments, individuals may be depicted as individual bars in a bar graph. In some embodiments, individuals may be depicted as slices of a pie chart. Accordingly, numerous formats may be used to display a comparison of an individual to one or more other individuals.

At operation 1206, the displaying operation 240 may include displaying one or more changes in the nutraceutical usage by the one or more individuals at two or more times. In some embodiments, one or more display units 130 may display one or more changes in nutraceutical usage by one or more individuals at two or more times. For example, in some embodiments, one or more display units 130 may display changes in the dosage of one or more nutraceuticals relative to a starting dosage at two or more times. In some embodiments, one or more display units 130 may display changes in the formulation of one or more nutraceuticals relative to a starting formulation at two or more times. Numerous changes may be displayed.

At operation 1208, the displaying operation 240 may include displaying one or more changes in the one or more parameters related to the one or more individuals at two or more times. In some embodiments, one or more display units 130 may display one or more changes in one or more parameters related to one or more individuals at two or more times. For example, in some embodiments, one or more display units 130 may display changes in the weight of an individual at two or more times. Numerous changes may be displayed.

At operation 1210, the displaying operation 240 may include displaying one or more changes in the nutraceutical usage by the one or more individuals at two or more times and one or more changes in the parameters related to the one or more individuals at two or more times. In some embodiments, one or more display units 130 may display one or more changes in nutraceutical usage by one or more individuals at two or more times and one or more changes in parameters related to the one or more individuals at two or more times. Accordingly, changes in nutraceutical usage may be displayed relative to changes in parameters over time. In some embodiments, such a display may be used to titrate nutraceutical usage to achieve a desired result.

Figure 13:
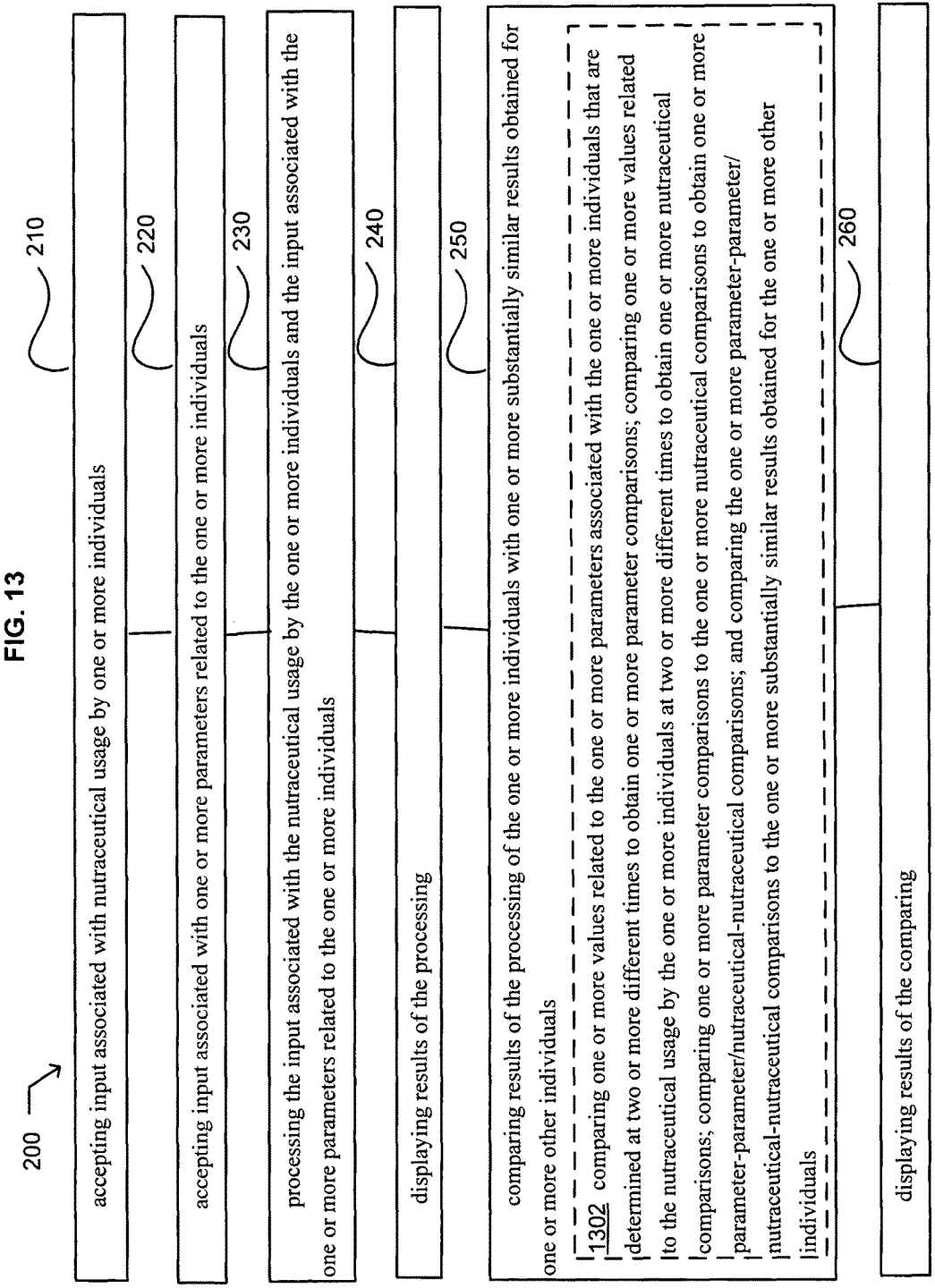
FIG. 13 illustrates alternative embodiments of the example operation flow of FIG. 2.

FIG. 13 illustrates alternative embodiments of the example operational flow 200 of FIG. 2. FIG. 13 illustrates example embodiments where the comparing operation 250 may include at least one additional operation. Additional operations may include an operation 1302.

At operation 1302, the comparing operation 250 may include:

comparing one or more values related to the one or more parameters associated with the one or more individuals that are determined at two or more different times to obtain one or more parameter comparisons;

comparing one or more values related to the nutraceutical usage by the one or more individuals at two or more different times to obtain one or more nutraceutical comparisons;

comparing one or more parameter comparisons to the one or more nutraceutical comparisons to obtain one or more parameter-parameter/nutraceutical-nutraceutical comparisons; and comparing the one or more parameter-parameter/nutraceutical-nutraceutical comparisons to the one or more substantially similar results obtained for the one or more other individuals.

In some embodiments, one or more computational units 120 may compare one or more values related to one or more parameters associated with one or more individuals that are determined at two or more different times to obtain one or more parameter comparisons; compare one or more values related to nutraceutical usage by the one or more individuals at two or more different times to obtain one or more nutraceutical comparisons; compare the one or more parameter comparisons to the one or more nutraceutical comparisons to obtain one or more parameter-parameter/nutraceutical-nutraceutical comparisons; and compare the one or more parameter-parameter/nutraceutical-nutraceutical comparisons to one or more substantially similar results obtained for one or more other individuals. Numerous values for nutraceutical usage and parameters associated with one or more individuals may be used.

Figure 14:
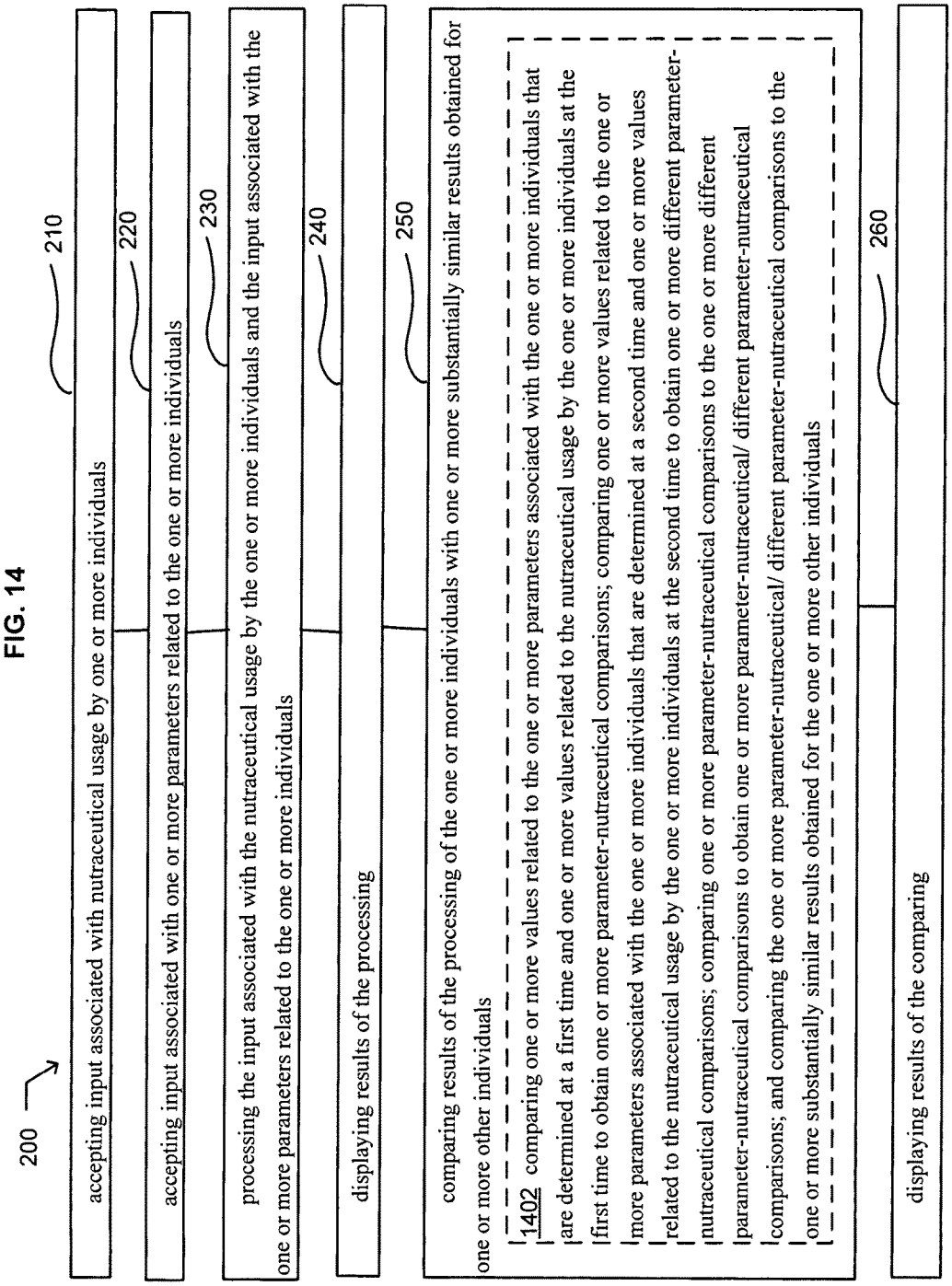
FIG. 14 illustrates alternative embodiments of the example operation flow of FIG. 2.

FIG. 14 illustrates alternative embodiments of the example operational flow 200 of FIG. 2. FIG. 14 illustrates example embodiments where the comparing operation 250 may include at least one additional operation. Additional operations may include an operation 1402.

At operation 1402, the comparing operation 250 may include:

comparing one or more values related to the one or more parameters associated with the one or more individuals that are determined at a first time and one or more values related to the nutraceutical usage by the one or more individuals at the first time to obtain one or more parameter-nutraceutical comparisons;

comparing one or more values related to the one or more parameters associated with the one or more individuals that are determined at a second time and one or more values related to the nutraceutical usage by the one or more individuals at the second time to obtain one or more different parameter-nutraceutical comparisons;

comparing one or more parameter-nutraceutical comparisons to the one or more different parameter-nutraceutical comparisons to obtain one or more parameter-nutraceutical/different parameter-nutraceutical comparisons; and comparing the one or more parameter-nutraceutical/different parameter-nutraceutical comparisons to the one or more substantially similar results obtained for the one or more other individuals.

In some embodiments, one or more computational units 120 may compare one or more values related to one or more parameters associated with one or more individuals that are determined at a first time and one or more values related to the nutraceutical usage by the one or more individuals at the first time to obtain one or more parameter-nutraceutical comparisons; compare one or more values related to one or more parameters associated with the one or more individuals that are determined at a second time and one or more values related to the nutraceutical usage by the one or more individuals at the second time to obtain one or more different parameter-nutraceutical comparisons; compare one or more parameter-nutraceutical comparisons to the one or more different parameter-nutraceutical comparisons to obtain one or more parameter-nutraceutical/different parameter-nutraceutical comparisons; and compare the one or more parameter-nutraceutical/different parameter-nutraceutical comparisons to the one or more substantially similar results obtained for the one or more other individuals. Numerous values for nutraceutical usage and parameters associated with one or more individuals may be used.

Figure 15:
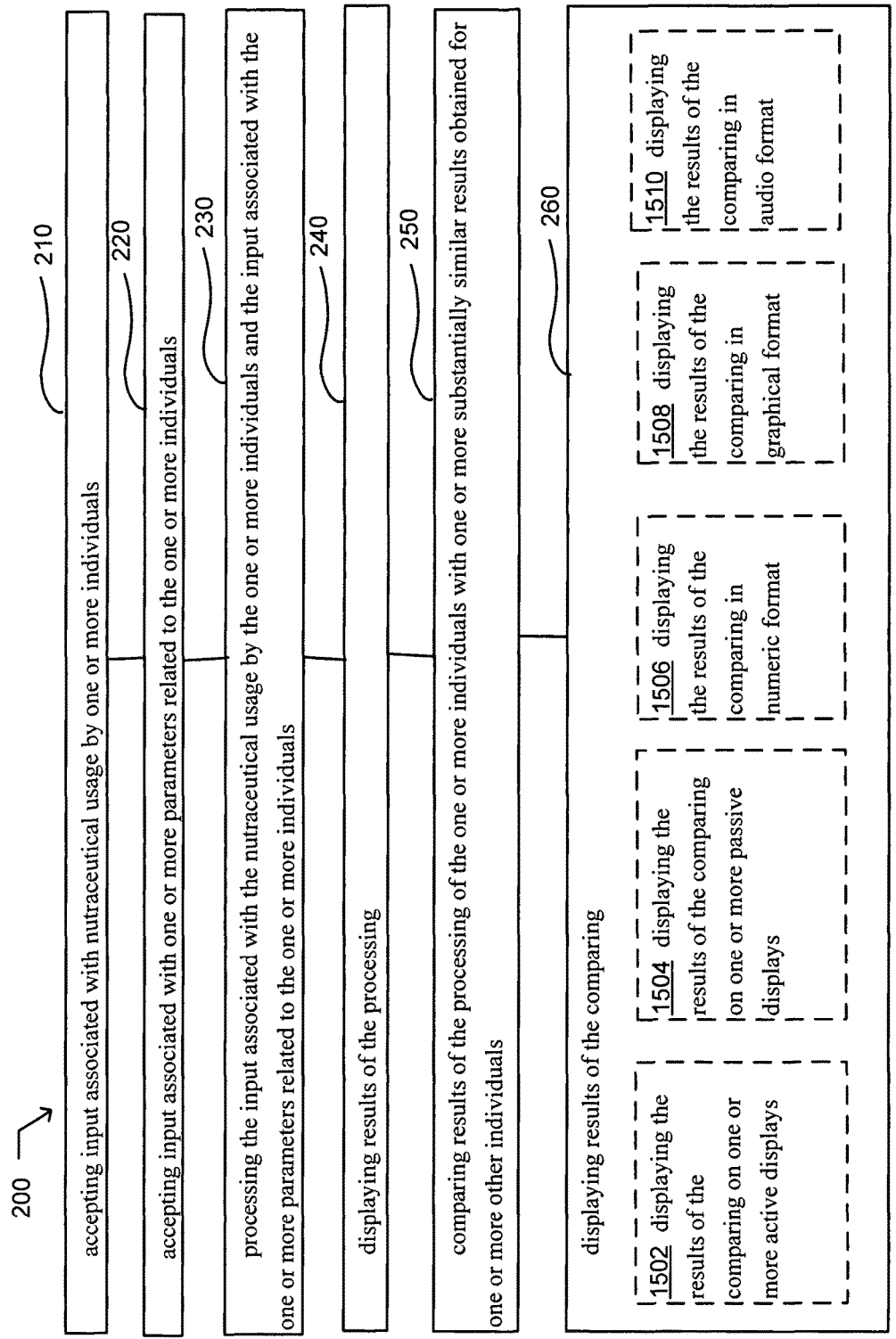
FIG. 15 illustrates alternative embodiments of the example operation flow of FIG. 2.

FIG. 15 illustrates alternative embodiments of the example operational flow 200 of FIG. 2. FIG. 15 illustrates example embodiments where the displaying operation 260 may include at least one additional operation. Additional operations may include an operation 1502, an operation 1504, an operation 1506, an operation 1508, and/or an operation 1510.

At operation 1502, the displaying operation 260 may include displaying the results of the comparing on one or more active displays. In some embodiments, one or more display units 130 may display results of processing on one or more active displays. Numerous active display units 130 are known and include, but are not limited to, quarter-video graphics array (QVGA), video graphics array (VGA), super video graphics array (SVGA), extended graphics array (XGA), wide extended graphics array (WXGA), super extended graphics array (SXGA), ultra extended graphics array (UXGA), wide super extended graphics array (WSXGA), wide ultra extended graphics array (WUXGA).

At operation 1504, the displaying operation 260 may include displaying the results of the comparing on one or more passive displays. In some embodiments, one or more display units 130 may display results of processing on one or more passive displays. In some embodiments, one or display units 130 may include one or more liquid crystal displays (LCD). Methods to construct passive displays have been described (e.g., U.S. Pat. Nos. 4,807,967; 4,729,636; 4,436,378; 4,257,041; herein incorporated by reference).

At operation 1506, the displaying operation 260 may include displaying the results of the comparing in numeric format. In some embodiments, one or more display units 130 may display results of processing in numeric format.

At operation 1508, the displaying operation 260 may include displaying the results of the comparing in graphical format. In some embodiments, one or more display units 130 may display results of processing in graphical format. Numerous types of graphical formats may be used. Examples of such graphical formats include, but are not limited to, use of shapes, use of colors, use of symbols (e.g., smiley face, frowny face, thumbs up sign, thumbs down sign, histograms, bar graphs, pie charts, and the like).

At operation 1510, the displaying operation 260 may include displaying the results of the comparing in audio format. In some embodiments, one or more display units 130 may display results of processing in audio format. In some embodiments, the results of processing may be presented in voice format. For example, in some embodiments, a voice may tell an individual to increase, decrease, or maintain one or more dosages of one or more nutraceuticals. In some embodiments, sounds may be used to indicate changes in nutraceutical usage and/or parameters related to an individual. In some embodiments, applause, cheering, and the like may be used to indicate a positive change. Examples of positive changes include, but are not limited to, weight loss, lowered blood pressure, lowered heart rate, and the like. In some embodiments, booing, hissing, nagging, and the like may be used to indicate a negative change. Examples of negative changes include, but are not limited to, weight gain, increased blood pressure, increased heart rate, and the like.

Figure 16:
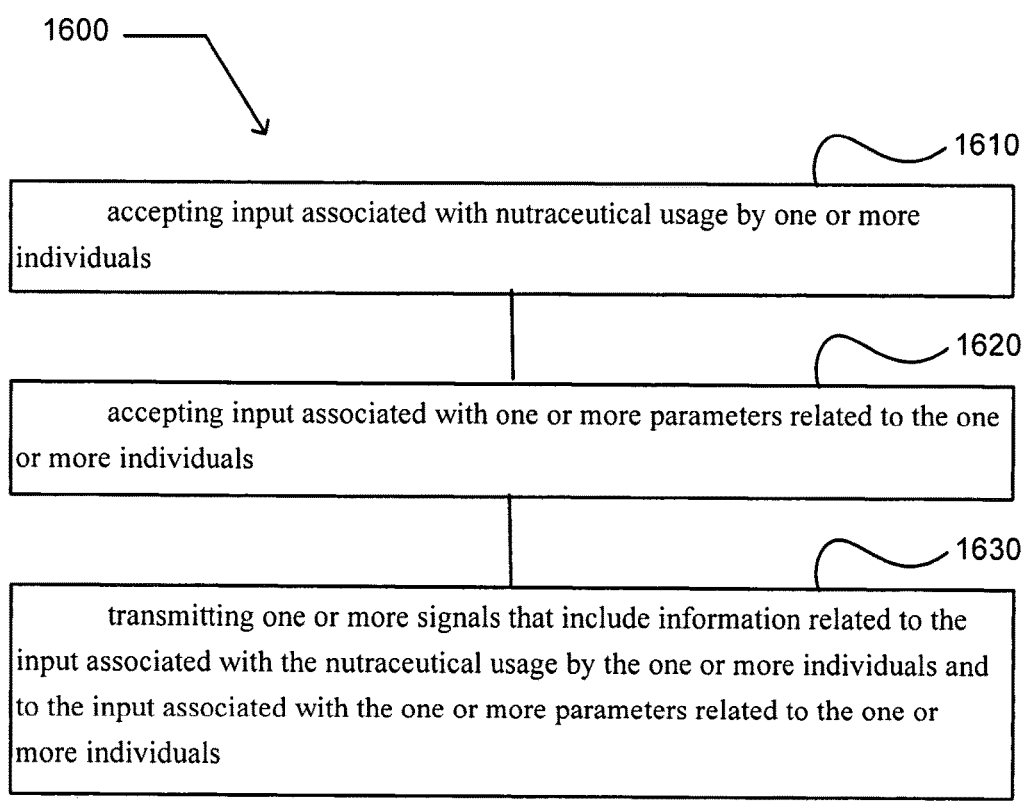
FIG. 16 illustrates an operational flow 1600 representing example operations related to accepting and transmitting input related to one or more nutraceuticals.

FIG. 16 illustrates an operational flow 1600 representing examples of operations that are related to the performance of one or more method related to one or more nutraceuticals. In FIG. 16 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1600 includes an accepting operation 1610 involving accepting input associated with nutraceutical usage by one or more individuals. In some embodiments, the accepting operation 1610 may include accepting input associated with the nutraceutical usage by the one or more individuals at two or more times. In some embodiments, the accepting operation 1610 may include accepting input associated with one or more concentrations of one or more nutraceuticals used by the one or more individuals. In some embodiments, the accepting operation 1610 may include accepting input associated with one or more identities of one or more nutraceuticals used by the one or more individuals. In some embodiments, the accepting operation 1610 may include accepting input associated with one or more formulations of one or more nutraceuticals used by the one or more individuals. In some embodiments, the accepting operation 1610 may include accepting input associated with one or more times of administration of one or more nutraceuticals used by the one or more individuals. In some embodiments, the accepting operation 1610 may include accepting input associated with one or more methods of administration of one or more nutraceuticals used by the one or more individuals. In some embodiments, the accepting operation 1610 may include accepting input associated with one or more pharmaceuticals used in conjunction with one or more nutraceuticals used by the one or more individuals.

After a start operation, the operational flow 1600 includes an accepting operation 1620 involving accepting input associated with one or more parameters related to the one or more individuals. In some embodiments, the accepting operation 1620 may include accepting input associated with one or more pharmaceuticals used by the one or more individuals. In some embodiments, the accepting operation 1620 may include accepting input associated with the one or more parameters related to the one or more individuals that are determined at two or more times. In some embodiments, the accepting operation 1620 may include accepting input related to one or more physical parameters related to the one or more individuals. In some embodiments, the accepting operation 1620 may include accepting input related to one or more mental parameters related to the one or more individuals. In some embodiments, the accepting operation 1620 may include accepting input related to one or more goals of the one or more individuals. In some embodiments, the accepting operation 1620 may include accepting input related to one or more plans of the one or more individuals. In some embodiments, the accepting operation 1620 may include accepting input related to one or more metabolic activities related to the one or more individuals. In some embodiments, the accepting operation 1620 may include accepting input related to sleep characteristics related to the one or more individuals. In some embodiments, the accepting operation 1620 may include accepting input related to exercise characteristics related to the one or more individuals. In some embodiments, the accepting operation 1620 may include accepting input related to nutritional characteristics related to the one or more individuals. In some embodiments, the accepting operation 1620 may include accepting input related to substance use by the one or more individuals. In some embodiments, the accepting operation 1620 may include accepting input related to weight of the one or more individuals. In some embodiments, the accepting operation 1620 may include accepting input related to body composition of the one or more individuals. In some embodiments, the accepting operation 1620 may include accepting input related to circulatory characteristics of the one or more individuals. In some embodiments, the accepting operation 1620 may include accepting input related to mood of the one or more individuals. In some embodiments, the accepting operation 1620 may include accepting input related to one or more proteins expressed within the one or more individuals. In some embodiments, the accepting operation 1620 may include accepting input related to expression of one or more genes within the one or more individuals.

After a start operation, the operational flow 1600 includes a transmitting operation 1630 involving transmitting one or more signals that include information related to the input associated with the nutraceutical usage by the one or more individuals and to the input associated with the one or more parameters related to the one or more individuals. In some embodiments, the transmitting operation 1630 may include transmitting the one or more signals associated with selection of one or more nutraceuticals for administration to the one or more individuals. In some embodiments, the transmitting operation 1630 may include transmitting the one or more signals associated with selection of one or more dosages of one or more nutraceuticals for administration to the one or more individuals. In some embodiments, the transmitting operation 1630 may include transmitting the one or more signals associated with selection of one or more nutraceuticals for administration to the one or more individuals and one or more health related recommendations. In some embodiments, the transmitting operation 1630 may include transmitting the one or more signals associated with comparing the information related to the input associated with the nutraceutical usage and the one or more parameters related to the one or more individuals to substantially similar information related to one or more different individuals.

Figure 17:
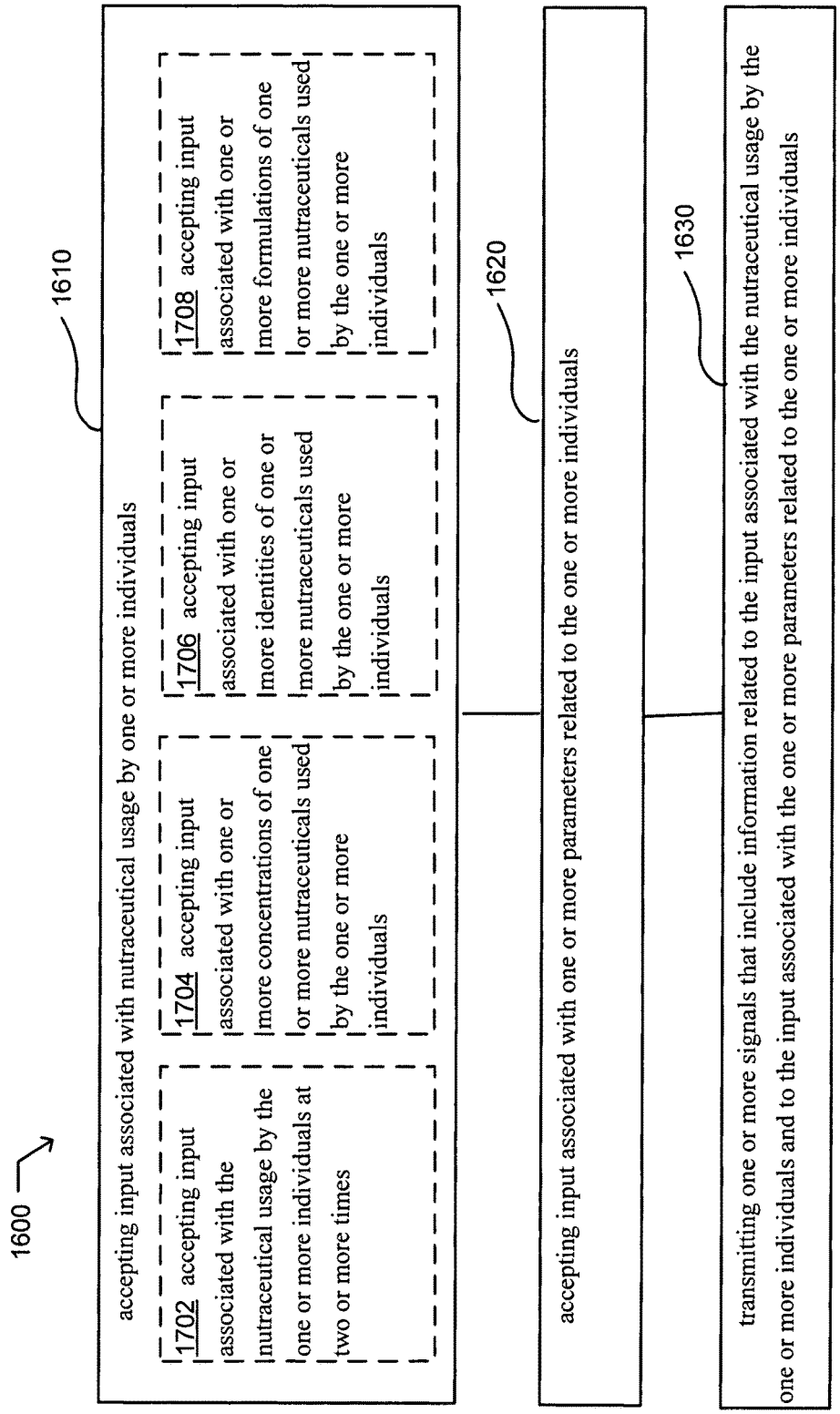
FIG. 17 illustrates alternative embodiments of the example operation flow of FIG. 16.

FIG. 17 illustrates alternative embodiments of the example operational flow 1600 of FIG. 16. FIG. 17 illustrates example embodiments where the accepting operation 1610 may include at least one additional operation. Additional operations may include an operation 1702, an operation 1704, an operation 1706, and/or an operation 1708.

At operation 1702, the accepting operation 1610 may include accepting input associated with the nutraceutical usage by the one or more individuals at two or more times. In some embodiments, one or more accepting units 110 may accept input associated with nutraceutical usage by one or more individuals at two or more times. In some embodiments, one or more accepting units 110 may accept input associated with nutraceutical usage by one or more individuals at one time.

At operation 1704, the accepting operation 1610 may include accepting input associated with one or more concentrations of one or more nutraceuticals used by the one or more individuals. In some embodiments, one or more accepting units 110 may accept input associated with one or more concentrations of one or more nutraceuticals used by one or more individuals. In some embodiments, one or more accepting units 110 may accept input associated with one or more concentrations of one or more nutraceuticals at the same time. In some embodiments, one or more accepting units 110 may accept input associated with one or more concentrations of one or more nutraceuticals at different times. In some embodiments, one or more accepting units 110 may accept input associated with one or more concentrations of one or more nutraceuticals over a series of time points. In some embodiments, one or more accepting units 110 may accept input associated with one or more concentrations that are expressed as an administered dosage. In some embodiments, one or more accepting units 110 may accept input associated with one or more concentrations of one or more nutraceuticals that are expressed as a systemic concentration of the one or more nutraceuticals within one or more individuals. In some embodiments, one or more accepting units 110 may accept input associated with one or more concentrations of one or more nutraceuticals that are excreted by one or more individuals.

At operation 1706, the accepting operation 1610 may include accepting input associated with one or more identities of one or more nutraceuticals used by the one or more individuals. In some embodiments, one or more accepting units 110 may accept input associated with one or more identities of one or more nutraceuticals used by one or more individuals. In some embodiments, one or more nutraceuticals may be identified by brand name. In some embodiments, one or more nutraceuticals may be identified by chemical name. In some embodiments, one or more nutraceuticals may be identified by popular name.

At operation 1708, the accepting operation 1610 may include accepting input associated with one or more formulations of one or more nutraceuticals used by the one or more individuals. In some embodiments, one or more accepting units 110 may accept input associated one or more formulations of one or more nutraceuticals used by the one or more individuals. Examples of such formulations include, but are not limited to, formulations that may be administered orally, transdermally, rectally, vaginally, peritoneally, nasally, and the like. In some embodiments, such formulations may include one or more components. For example, in some embodiments, a formulation may include numerous vitamins, minerals, and the like.

Figure 18:
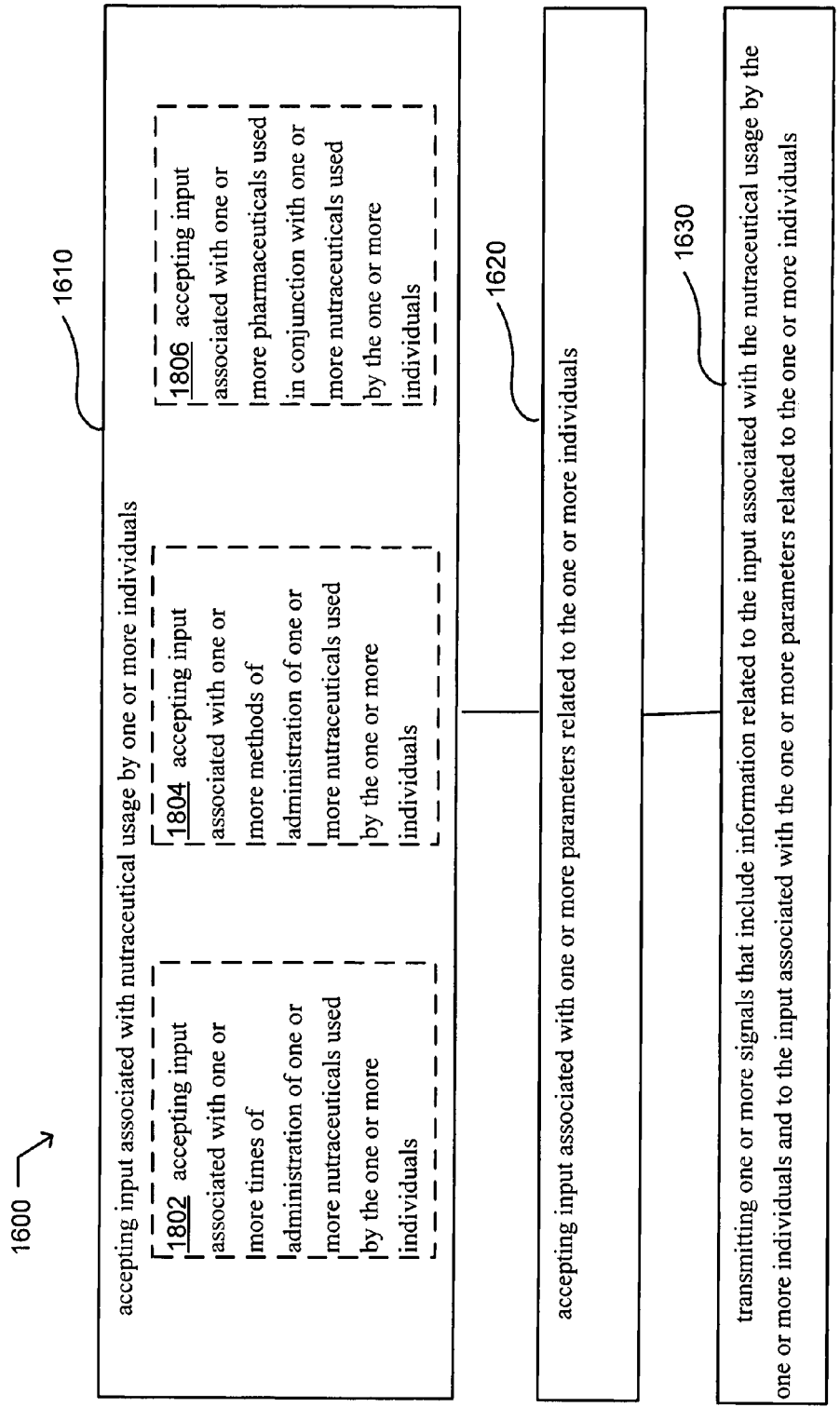
FIG. 18 illustrates alternative embodiments of the example operation flow of FIG. 16.

FIG. 18 illustrates alternative embodiments of the example operational flow 1600 of FIG. 16. FIG. 18 illustrates example embodiments where the accepting operation 1610 may include at least one additional operation. Additional operations may include an operation 1802, an operation 1804, and/or an operation 1806.

At operation 1802, the accepting operation 1610 may include accepting input associated with one or more times of administration of one or more nutraceuticals used by the one or more individuals. In some embodiments, one or more accepting units 110 may accept input associated with one or more times of administration of one or more nutraceuticals used by one or more individuals. For example, in some embodiments, one or more accepting units 110 may accept input associated with multiple administrations of one or more nutraceuticals at multiple times. Accordingly, such input may be used to prepare a presentation showing nutraceutical administration relative to time. In some embodiments, additional information may be combined with times of nutraceutical administration. For example, in some embodiments, time of administration may be combined with the identity of one or more nutraceuticals, the concentration of one or more nutraceuticals, the formulation of one or more nutraceuticals, the route of administration of one or more nutraceuticals, parameters associated with one or more individuals, or substantially any combination thereof.

At operation 1804, the accepting operation 1610 may include accepting input associated with one or more methods of administration of one or more nutraceuticals used by the one or more individuals. In some embodiments, one or more accepting units 110 may accept input associated with one or more methods of administration of one or more nutraceuticals used by one or more individuals. Numerous methods may be used to administer one or more nutraceuticals to one or more individuals. Examples of such methods include, but are not limited to, oral administration, parenteral administration, transdermal administration, nasal administration, sublingual administration, vaginal administration, rectal administration, and the like.

At operation 1806, the accepting operation 1610 may include accepting input associated with one or more pharmaceuticals used in conjunction with one or more nutraceuticals used by the one or more individuals. In some embodiments, one or more accepting units 110 may accept input associated with one or more pharmaceuticals used in conjunction with one or more nutraceuticals used by one or more individuals. One or more accepting units 110 may accept numerous types of input related to pharmaceuticals. Examples of such input include, but are not limited to, route of administration, time of administration, identity of one or more pharmaceuticals, concentration of one or more pharmaceuticals, interactions of one or more pharmaceuticals with other pharmaceuticals and/or nutraceuticals, mechanism of action utilized by one or more pharmaceuticals, and the like.

Figure 19:
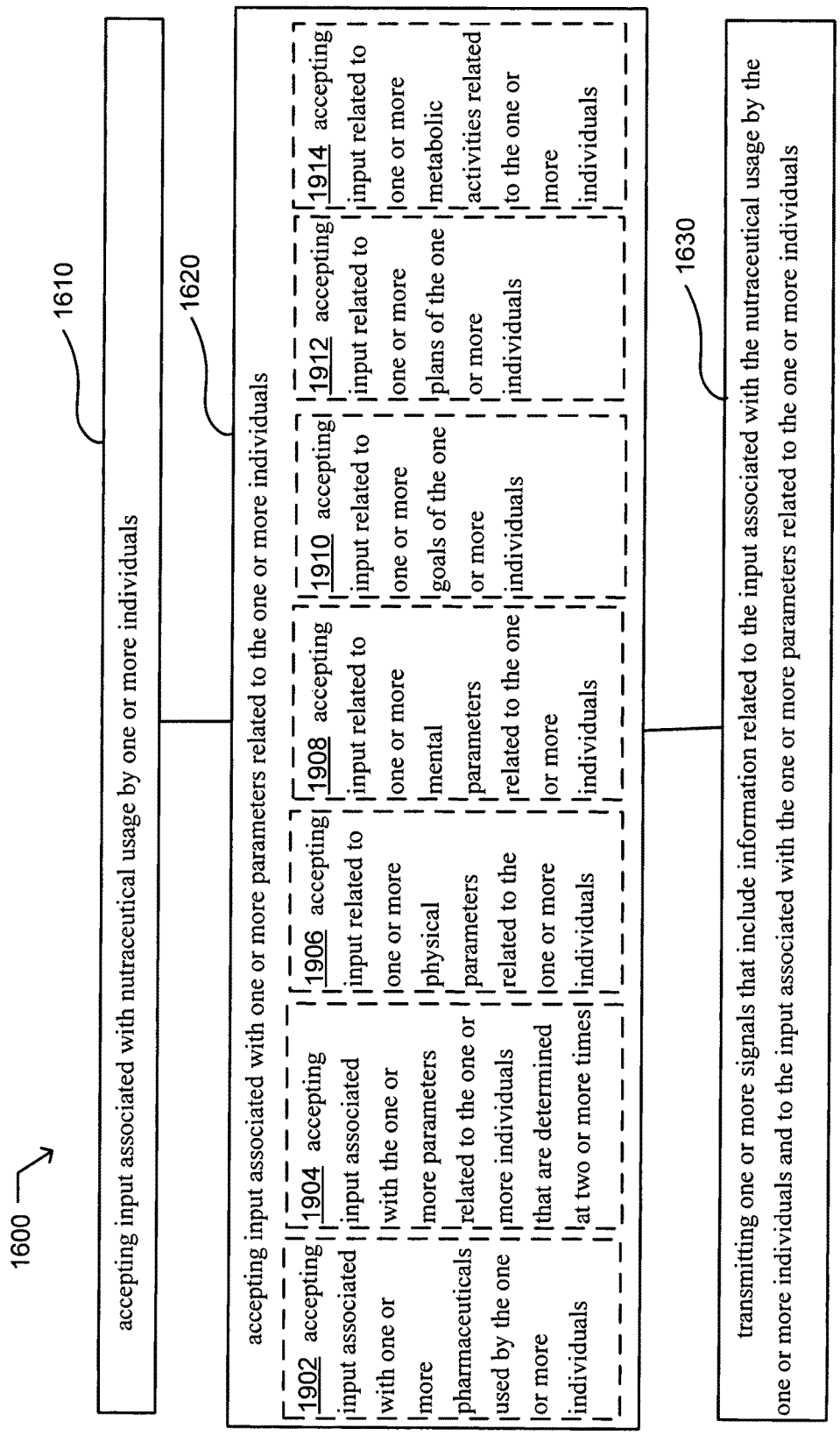
FIG. 19 illustrates alternative embodiments of the example operation flow of FIG. 16.

FIG. 19 illustrates alternative embodiments of the example operational flow 1600 of FIG. 16. FIG. 19 illustrates example embodiments where the accepting operation 1620 may include at least one additional operation. Additional operations may include an operation 1902, an operation 1904, an operation 1906, an operation 1908, an operation 1910, an operation 1912, and/or an operation 1914.

At operation 1902, the accepting operation 1620 may include accepting input associated with one or more pharmaceuticals used by the one or more individuals. In some embodiments, one or more accepting units 110 may accept input associated with one or more pharmaceuticals used by one or more individuals. In some embodiments, one or more accepting units 110 may accept input associated with the identity of one or more pharmaceuticals. In some embodiments, one or more accepting units 110 may accept input associated with the dosage of one or more pharmaceuticals. In some embodiments, one or more accepting units 110 may accept input associated with contraindications of one or more pharmaceuticals. In some embodiments, one or more accepting units 110 may accept input associated with allergies associated with one or more pharmaceuticals. In some embodiments, one or more accepting units 110 may accept input associated with the duration with which one or more pharmaceuticals are administered. Accordingly, input may include numerous types of information associated with one or more pharmaceuticals.

At operation 1904, the accepting operation 1620 may include accepting input associated with the one or more parameters related to the one or more individuals that are determined at two or more times. In some embodiments, one or more accepting units 110 may accept input associated with one or more parameters related to one or more individuals that are determined at two or more times. One or more accepting units 110 may accept numerous parameters related to one or more individuals. Examples of such parameters include, but are not limited to, physical parameters (e.g., height, weight, age, body composition, blood pressure, heart rate), mental parameters (e.g., depression, happiness, love, hate, loneliness, hopelessness, joy, acquity, memory, alertness), task related parameters (e.g., physical activity, presentation preparation, work related activity), environment related parameters (e.g., travel, allergens, pathogens), goal related parameters (e.g., lower blood pressure, weight loss, sleep acquisition, sleep avoidance, weight gain, muscle gain, fat loss), and the like. In some embodiments, one or more accepting units 110 may accept input at numerous different times. For example, in some embodiments, one or more accepting units 110 may accept physical parameters, such as an individual's weight or body mass index, at numerous time points. Accordingly, such input may be utilized to track changes in one or more parameters over time.

At operation 1906, the accepting operation 1620 may include accepting input related to one or more physical parameters related to the one or more individuals. In some embodiments, one or more accepting units 110 may accept input related to one or more physical parameters related to one or more individuals. One or more accepting units 110 may accept numerous physical parameters. Examples of such physical parameters may include, but are not limited to, height, weight, age, health, disease, physical state, injury, dental health, health history, family health history, and the like.

At operation 1908, the accepting operation 1620 may include accepting input related to one or more mental parameters related to the one or more individuals. In some embodiments, one or more accepting units 110 may accept input related to one or more mental parameters related to one or more individuals. One or more accepting units 110 may accept numerous mental parameters. Examples of such mental parameters may include, but are not limited to, mood (e.g., happiness, sadness, elation, depression, love, hate, loneliness, hopelessness), mental health (e.g., bipolar disorder, schizophrenia, multiple personality disorder, obsessive compulsive disorder, Alzheimer's disease), mental health history, family mental health history, mental function (e.g., alertness, acquity), and the like.

At operation 1910, the accepting operation 1620 may include accepting input related to one or more goals of the one or more individuals. In some embodiments, one or more accepting units 110 may accept input related to one or more goals of one or more individuals. One or more accepting units 110 may accept numerous goal related parameters. Examples of such goal related parameters may include, but are not limited to, athletic performance (e.g., weight gain, weight loss, muscle gain, fat loss, decreased body mass index, endurance, strength), mental performance (e.g., alertness, memory, acuity), and the like.

At operation 1912, the accepting operation 1620 may include accepting input related to one or more plans of the one or more individuals. In some embodiments, one or more accepting units 110 may accept input related to one or more plans of one or more individuals. In some embodiments, one or more accepting units 110 may accept input related to the travel plans of one or more individuals. In some embodiments, one or more accepting units 110 may accept input related to the work plans of one or more individuals. In some embodiments, one or more accepting units 110 may accept input related to the exercise plans of one or more individuals. Accordingly, one or more accepting units 110 may accept input that includes numerous types of information related to the plans of one or more individuals.

At operation 1914, the accepting operation 1620 may include accepting input related to one or more metabolic activities related to the one or more individuals. In some embodiments, one or more accepting units 110 may accept input related to one or more metabolic activities related to one or more individuals. One or more accepting units 110 may accept input related to numerous types of metabolic activity. Examples of input related to metabolic activities include, but are not limited to, respiration rate, enzyme activity, oxygen consumption, heart rate, digestion, fatty acid-oxidation, hormone activity, vasodilation, vasoconstriction, pH, carbon dioxide concentration (e.g., blood, expired), oxygen concentrations (e.g., blood, expired), catabolic reactions, anabolic reactions, lipid metabolism, sugar metabolism, and the like.

Figure 20:
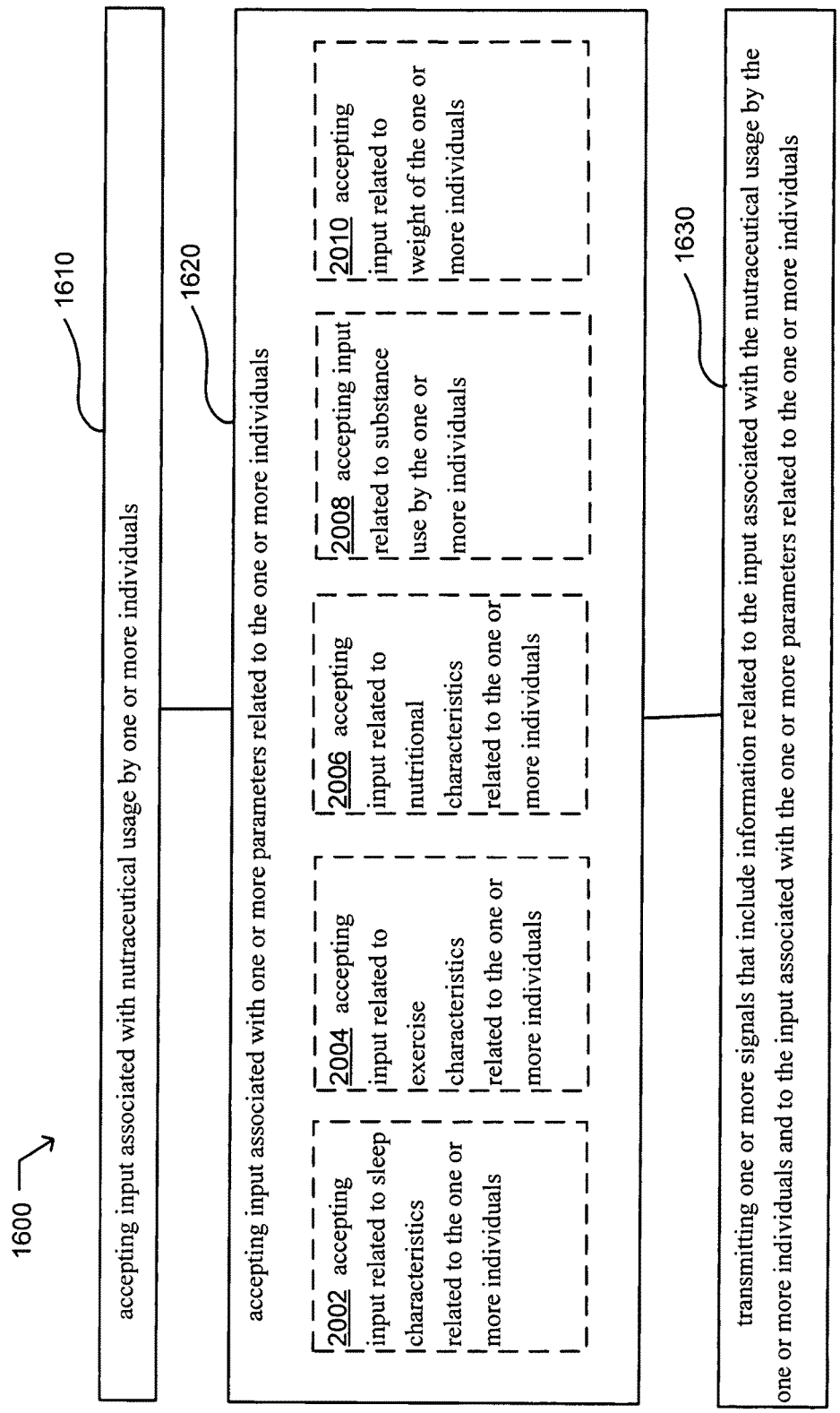
FIG. 20 illustrates alternative embodiments of the example operation flow of FIG. 16.

FIG. 20 illustrates alternative embodiments of the example operational flow 1600 of FIG. 16. FIG. 20 illustrates example embodiments where the accepting operation 1620 may include at least one additional operation. Additional operations may include an operation 2002, an operation 2004, an operation 2006, an operation 2008, and/or an operation 2010.

At operation 2002, the accepting operation 1620 may include accepting input related to sleep characteristics related to the one or more individuals. In some embodiments, one or more accepting units 110 may accept input related to sleep characteristics related to one or more individuals. In some embodiments, one or more input units may accept input related to the number of hours that one or more individuals sleep during a time period. In some embodiments, one or more input units may accept input related to times when one or more individuals sleep during a time period. In some embodiments, one or more input units may accept input related to the sleep schedules of one or more individuals. In some embodiments, one or more input units may accept input related to the quality of sleep obtained by one or more individuals. In some embodiments, one or more input units may accept input related to alertness felt by one or more individuals. In some embodiments, one or more input units may accept input related to sleep characteristics. For example, such input may include information related to positive and/or negative sleep experience, tiredness, restlessness, insomnia, alertness, feelings of tiredness, and the like. Accordingly, one or more input units may accept numerous types of input related to the sleep characteristics of one or more individuals.

At operation 2004, the accepting operation 1620 may include accepting input related to exercise characteristics related to the one or more individuals. In some embodiments, one or more accepting units 110 may accept input related to exercise characteristics related to one or more individuals. Input related to exercise characteristics may include, but is not limited to, type of exercise, duration of exercise, intensity of exercise, frequency of exercise, physiological parameters (e.g., pulse, blood pressure, oxygen consumption, carbon dioxide production) occurring during exercise, and the like.

At operation 2006, the accepting operation 1620 may include accepting input related to nutritional characteristics related to the one or more individuals. In some embodiments, one or more accepting units 110 may accept input related to nutritional characteristics related to one or more individuals. Input related to nutritional characteristics may include, but is not limited to, types of food consumed (e.g., functional foods), types of beverages consumed, number of calories consumed, composition of consumed items (e.g., fat content, cholesterol content, oil content, caloric content), times of consumption, and the like.

At operation 2008, the accepting operation 1620 may include accepting input related to substance use by the one or more individuals. In some embodiments, one or more accepting units 110 may accept input related to substance use by the one or more individuals. Examples of such input include, but are not limited to, alcohol use, tobacco use, nicotine intake, pharmaceutical use, illicit drug use, food supplement use, nutraceutical use, and the like.

At operation 2010, the accepting operation 1620 may include accepting input related to weight of the one or more individuals. In some embodiments, one or more accepting units 110 may accept input related to weight of one or more individuals. One or more accepting units 110 may accept input related to present weight, past weight, future weight goals, or substantially any combination thereof.

Figure 21:
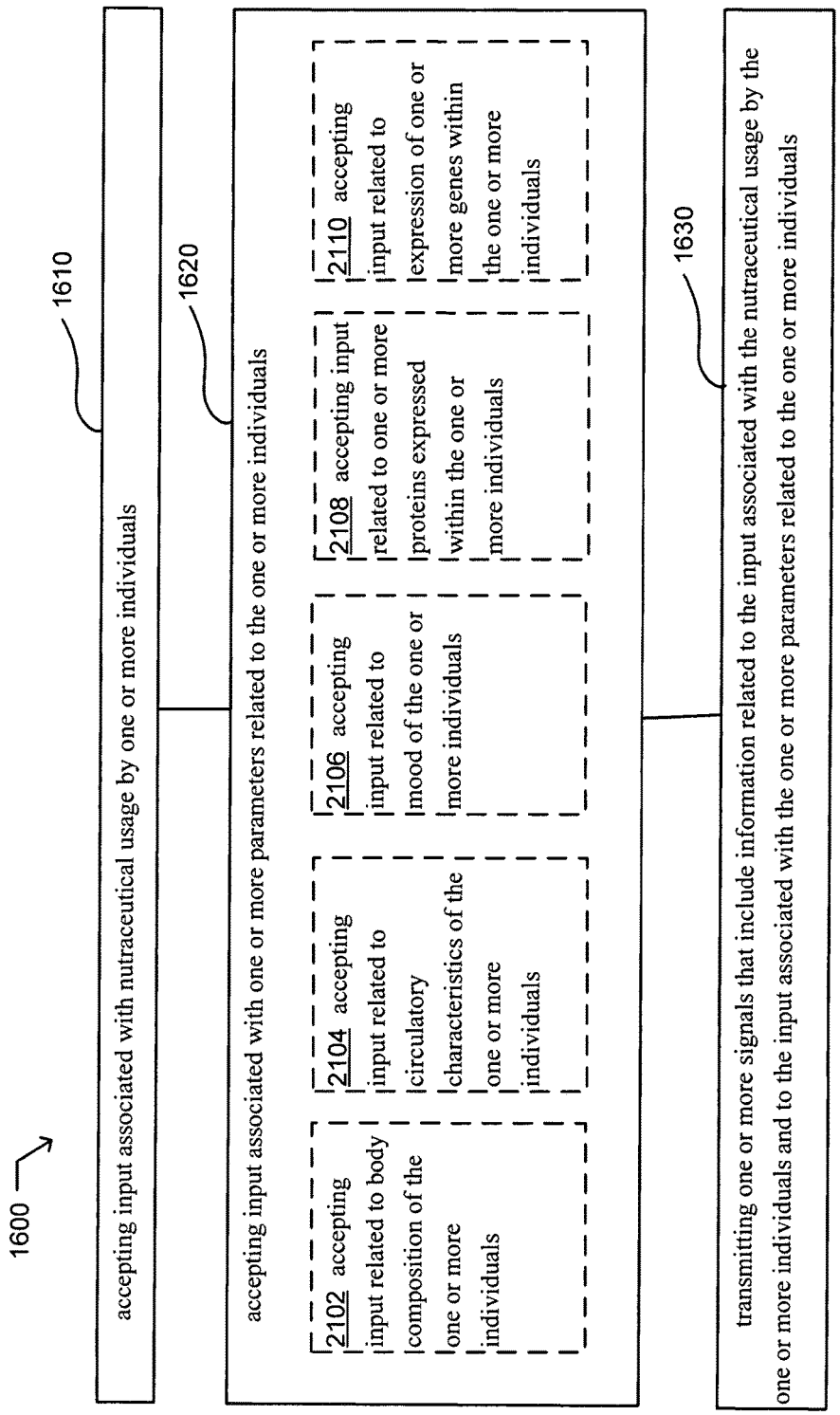
FIG. 21 illustrates alternative embodiments of the example operation flow of FIG. 16.

FIG. 21 illustrates alternative embodiments of the example operational flow 1600 of FIG. 16. FIG. 21 illustrates example embodiments where the accepting operation 1620 may include at least one additional operation. Additional operations may include an operation 2102, an operation 2104, an operation 2106, an operation 2108, and/or an operation 2110.

At operation 2102, the accepting operation 1620 may include accepting input related to body composition of the one or more individuals. In some embodiments, one or more accepting units 110 may accept input related to body composition of one or more individuals. The results from numerous body composition tests may be accepted by one or more accepting units 110. Examples of such tests include, but are not limited to, skinfold measurement, body mass index, waist to hip ratio, hydrostatic weighing, bioelectric impedance, dual-energy X-ray absorptiometry, near infrared interactance, total body potassium, whole-body air-displacement plethysmography, magnetic resonance imaging, total body electrical conductivity, computed tomography, total body protein, or substantially any combination thereof.

At operation 2104, the accepting operation 1620 may include accepting input related to circulatory characteristics of the one or more individuals. In some embodiments, one or more accepting units 110 may accept input related to circulatory characteristics of one or more individuals. One or more accepting units 110 may accept input related to numerous types of circulatory characteristics. Examples of such circulatory characteristics include, but are not limited to, blood pressure, hypertension, heart rate, vasoelasticity, cholesterol levels, coronary heart disease, atherosclerosis, and the like.

At operation 2106, the accepting operation 1620 may include accepting input related to mood of the one or more individuals. In some embodiments, one or more accepting units 110 may accept input related to the mood of one or more individuals. Examples of various moods that may be input include, but are not limited to, happiness, sadness, loneliness, confusion, forgetfulness, joy, glee, euphoria, hopelessness, anger, rage, love, contempt, hate, frustration, and the like.

At operation 2108, the accepting operation 1620 may include accepting input related to one or more proteins expressed within the one or more individuals. In some embodiments, one or more accepting units 110 may accept input related to one or more proteins expressed within one or more individuals. For example, the enzyme 5,10-methylenetetrahydrofolate reductase catalyzes the conversion of 5,10-methylenetetrahydrofolate, required for purine and thymidine syntheses, to 5-methyltetrahydrofolate, the primary circulatory form of folate necessary for methionine synthesis. A common mutation (677C→T) in 5,10-methylenetetrahydrofolate reductase reduces enzyme activity, leading to lower levels of 5-methyltetrahydrofolate. It has been determined that men having adequate folate levels who are homozygous for the mutation (677T/677T) exhibit a three-fold decrease in risk of colorectal cancer when compared to men having adequate folate levels who are homozygous normal (677C/677C) or heterozygous (677C/677T). However, the protection due to the mutation was absent in men with folate deficiency. In men with the homozygous normal genotype who drink little or no alcohol as reference, men with the homozygous mutation who drink little or no alcohol have an eight-fold decrease in risk and moderate drinkers exhibit a two-fold reduction in risk (Ma et al., Cancer Research, 57:1098-1102 (1997)). Polymorphisms in genes involved in folate metabolism have also been linked to maternal risk factors for Down Syndrome, neural tube defects, and oral clefts (Mills et al., Am. J. Med. Genet., 86:71-74 (1999); Wilson et al., Mol. Genet. Metab., 67:317-323 (1999); Hobbs et al., Am. J. Med. Genet., 67:623-630 (2000)). Accordingly, in some embodiments, information related to production of one or more proteins within an individual may be input. Such information may be used during the selection of nutraceuticals for administration to an individual. Such information may also be used to suggest health-related information. In some embodiments, one or more accepting units 110 may accept input related to the concentration of one or more proteins expressed within an individual. In some embodiments, one or more accepting units 110 may accept input related to the activity of one or more proteins expressed within an individual. Accordingly, one or more accepting units 110 may accept information related to numerous proteins and properties of proteins expressed within an individual.

At operation 2110, the accepting operation 1620 may include accepting input related to expression of one or more genes within the one or more individuals. In some embodiments, one or more accepting units 110 may accept input related to expression of one or more genes within one or more individuals. In some embodiments, such information may be used during the selection of nutraceuticals for administration to an individual. Such information may also be used to suggest health-related information. For example, folate status and common variations in genes that code for folate dependent enzymes are linked to many types of cancer, vascular disease, birth defects, and complications of pregnancy. This arises because several molecular mechanisms that underpin the genomic machinery are sensitive to B vitamin status and, in particular, are responsive to the interaction between folate nutrition and folate dependent enzyme polymorphisms (Lucock, B M J, 328:211-214 (2004)). Accordingly, genetic information may be utilized during the selection of one or more nutraceuticals for administration to an individual. In another example, black tea polyphenols (e.g., a theaflavin-3-monogallate and theaflavin-3'-monogallate mixture) have been shown to suppress cyclooxygenase 2 (Cox-2) gene expression at both the messenger ribonucleic acid and protein level (Lu et al., Cancer Reserch, 60:6465-6471 (2000)). Pharmacological inhibition of COX can provide relief from the symptoms of inflammation and pain. Accordingly, in some embodiments, input related to COX gene expression may be accepted by one or more accepting units 110 to follow nutraceutical mediated inhibition of COX expression. Black tea extracts also exhibit chemoprotective activity (Lu et al., Cancer Reserch, 60:6465-6471 (2000)). In another example, a resveratrol analog (3,4,5,4'-tetrahydroxystilbene) has been shown to differentially induce pro-apoptotic p53/Bax gene expression and inhibit the growth of transformed cells but not their normal counterparts (Lu et al., Carcinogenesis, 22:321-328 (2001)). Accordingly, p53/Bax gene expression may be input to follow resveratrol analog mediated induction of gene expression. Numerous nutraceuticals mediate induction or inhibition of gene expression (e.g., Chen et al., Cancer Letters, 129:173-179 (1998); British J. Cancer, 92:513-521 (2005)). In another example, dietary omega-3 polyunsaturated fatty acids were shown to affect brain gene expression (Kitajka et al., PNAS, 101:10931-10936 (2004)). In some embodiments, one or more accepting units 110 may accept input related to the expression level of one or more genes within an individual. In some embodiments, one or more accepting units 110 may accept input related to the activity of one or more gene products expressed within an individual. Accordingly, one or more accepting units 110 may accept information related to numerous genes and the products of gene expression within an individual.

Figure 22:
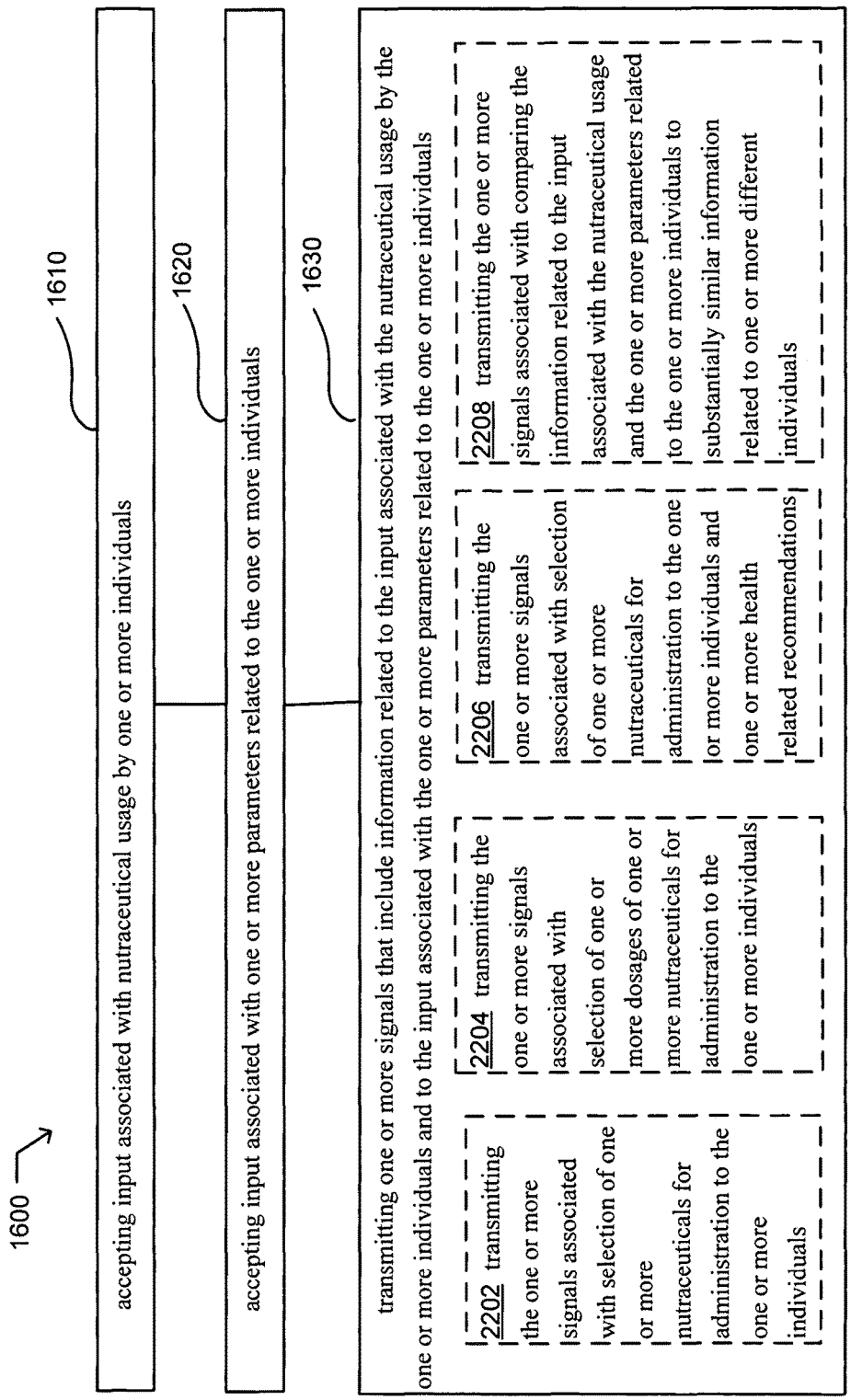
FIG. 22 illustrates alternative embodiments of the example operation flow of FIG. 16.

FIG. 22 illustrates alternative embodiments of the example operational flow 1600 of FIG. 16. FIG. 22 illustrates example embodiments where the transmitting operation 1630 may include at least one additional operation. Additional operations may include an operation 2202, an operation 2204, an operation 2206, and/or an operation 2208.

At operation 2202, the transmitting operation 1630 may include transmitting the one or more signals associated with selection of one or more nutraceuticals for administration to the one or more individuals. In some embodiments, one or more transmitting units 140 may transmit one or more signals associated with selection of one or more nutraceuticals for administration to one or more individuals. In some embodiments, one or more transmitting units 140 may transmit one or more signals associated with the identity of one or more nutraceuticals for administration to one or more individuals.

At operation 2204, the transmitting operation 1630 may include transmitting the one or more signals associated with selection of one or more dosages of one or more nutraceuticals for administration to the one or more individuals. In some embodiments, one or more transmitting units 140 may transmit one or more signals associated with selection of one or more dosages of one or more nutraceuticals for administration to one or more individuals.

At operation 2206, the transmitting operation 1630 may include transmitting the one or more signals associated with selection of one or more nutraceuticals for administration to the one or more individuals and one or more health related recommendations. In some embodiments, one or more transmitting units 140 may transmit one or more signals associated with selection of one or more nutraceuticals for administration to the one or more individuals and one or more health related recommendations. Examples of health related recommendations may include, but are not limited to, recommendations associated with diet, sleep habits, substance use, weight, exercise, and the like.

At operation 2208, the transmitting operation 1630 may include transmitting the one or more signals associated with comparing the information related to the input associated with the nutraceutical usage and the one or more parameters related to the one or more individuals to substantially similar information related to one or more different individuals. In some embodiments, one or more transmitting units 140 may transmit one or more signals associated with comparing information related to input associated with nutraceutical usage and one or more parameters related to one or more individuals to substantially similar information related to one or more different individuals.

Figure 23:
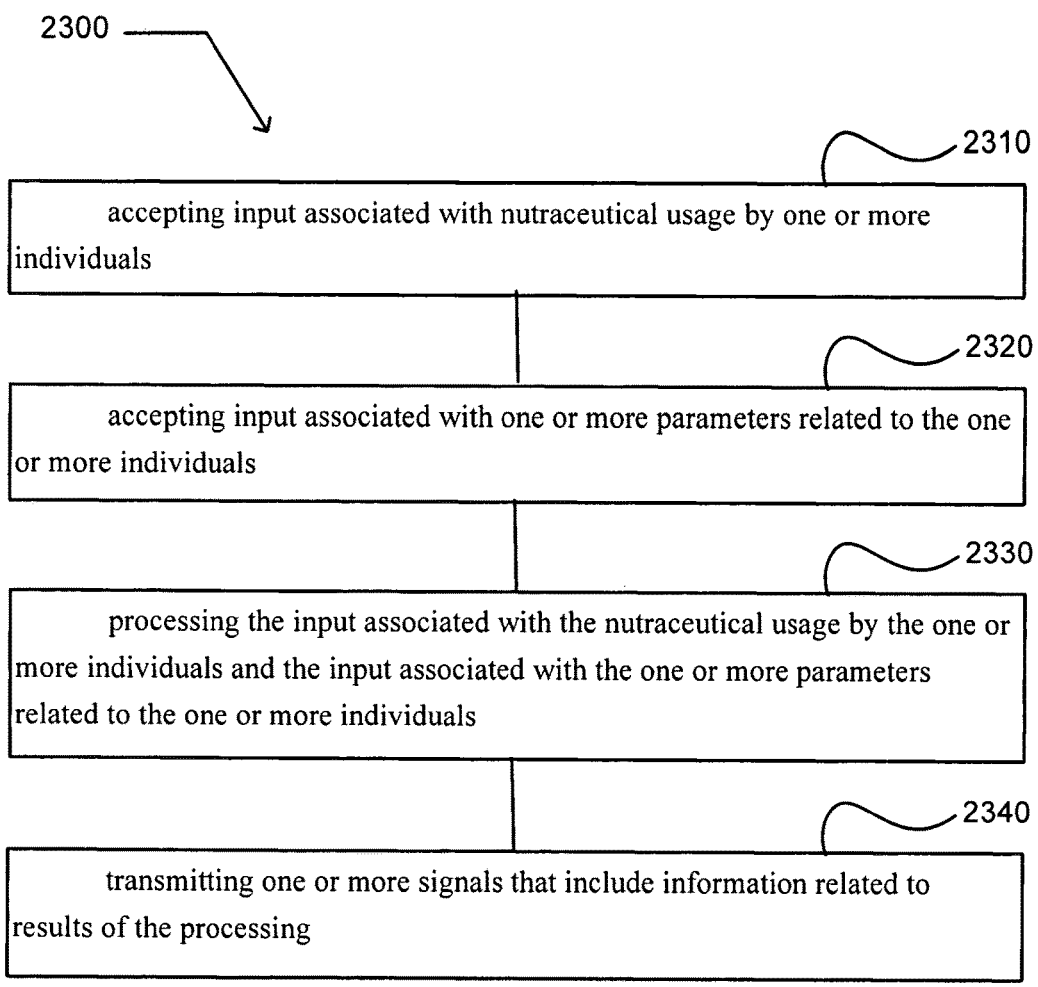
FIG. 23 illustrates an operational flow 2300 representing example operations related to accepting, processing, and transmitting input related to one or more nutraceuticals.

FIG. 23 illustrates an operational flow 2300 representing examples of operations that are related to the performance of one or more methods related to one or more nutraceuticals. In FIG. 23 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 2300 includes an accepting operation 2310 involving accepting input associated with nutraceutical usage by one or more individuals. In some embodiments, the accepting operation 2310 may include accepting input associated with the nutraceutical usage by the one or more individuals at two or more times. In some embodiments, the accepting operation 2310 may include accepting input associated with one or more concentrations of one or more nutraceuticals used by the one or more individuals. In some embodiments, the accepting operation 2310 may include accepting input associated with one or more identities of one or more nutraceuticals used by the one or more individuals. In some embodiments, the accepting operation 2310 may include accepting input associated with one or more formulations of one or more nutraceuticals used by the one or more individuals. In some embodiments, the accepting operation 2310 may include accepting input associated with one or more times of administration of one or more nutraceuticals used by the one or more individuals. In some embodiments, the accepting operation 2310 may include accepting input associated with one or more methods of administration of one or more nutraceuticals used by the one or more individuals. In some embodiments, the accepting operation 2310 may include accepting input associated with one or more pharmaceuticals used in conjunction with one or more nutraceuticals used by the one or more individuals.

After a start operation, the operational flow 2300 includes an accepting operation 2320 involving accepting input associated with one or more parameters related to the one or more individuals. In some embodiments, the accepting operation 2320 may include accepting input associated with one or more pharmaceuticals used by the one or more individuals. In some embodiments, the accepting operation 2320 may include accepting input associated with the one or more parameters related to the one or more individuals that are determined at two or more times. In some embodiments, the accepting operation 2320 may include accepting input related to one or more physical parameters related to the one or more individuals. In some embodiments, the accepting operation 2320 may include accepting input related to one or more mental parameters related to the one or more individuals. In some embodiments, the accepting operation 2320 may include accepting input related to one or more goals of the one or more individuals. In some embodiments, the accepting operation 2320 may include accepting input related to one or more plans of the one or more individuals. In some embodiments, the accepting operation 2320 may include accepting input related to one or more metabolic activities related to the one or more individuals. In some embodiments, the accepting operation 2320 may include accepting input related to sleep characteristics related to the one or more individuals. In some embodiments, the accepting operation 2320 may include accepting input related to exercise characteristics related to the one or more individuals. In some embodiments, the accepting operation 2320 may include accepting input related to nutritional characteristics related to the one or more individuals. In some embodiments, the accepting operation 2320 may include accepting input related to substance use by the one or more individuals. In some embodiments, the accepting operation 2320 may include accepting input related to weight of the one or more individuals. In some embodiments, the accepting operation 2320 may include accepting input related to body composition of the one or more individuals. In some embodiments, the accepting operation 2320 may include accepting input related to circulatory characteristics of the one or more individuals. In some embodiments, the accepting operation 2320 may include accepting input related to mood of the one or more individuals. In some embodiments, the accepting operation 2320 may include accepting input related to one or more proteins expressed within the one or more individuals. In some embodiments, the accepting operation 2320 may include accepting input related to expression of one or more genes within the one or more individuals.

After a start operation, the operational flow 2300 includes a processing operation 2330 involving processing the input associated with the nutraceutical usage by the one or more individuals and the input associated with the one or more parameters related to the one or more individuals. In some embodiments, the processing operation 2330 may include comparing the input associated with the nutraceutical usage by the one or more individuals to the input associated with the one or more parameters related to the one or more individuals. In some embodiments, the processing operation 2330 may include calculating one or more ratios of the input associated with the nutraceutical usage by the one or more individuals to the input associated with the one or more parameters related to the one or more individuals. In some embodiments, the processing operation 2330 may include calculating one or more ratios of the input associated with the nutraceutical usage by the one or more individuals to the input associated with the one or more parameters related to the one or more individuals at two or more times. In some embodiments, the processing operation 2330 may include determining one or more changes in the nutraceutical usage by the one or more individuals at two or more times. In some embodiments, the processing operation 2330 may include determining one or more changes in the one or more parameters related to the one or more individuals. In some embodiments, the processing operation 2330 may include comparing one or more changes in the nutraceutical usage by the one or more individuals to the one or more changes in the one or more parameters related to the one or more individuals. In some embodiments, the processing operation 2330 may include comparing one or more changes in the nutraceutical usage by the one or more individuals to the one or more changes in the one or more parameters related to the one or more individuals at two or more times.

After a start operation, the operational flow 2300 includes a transmitting operation 2340 involving transmitting one or more signals that include information related to results of the processing. In some embodiments, the transmitting operation 2340 may include transmitting the one or more signals associated with selection of one or more nutraceuticals for administration to the one or more individuals. In some embodiments, the transmitting operation 2340 may include transmitting the one or more signals associated with selection of one or more dosages of one or more nutraceuticals for administration to the one or more individuals. In some embodiments, the transmitting operation 2340 may include transmitting the one or more signals associated with selection of one or more nutraceuticals for administration to the one or more individuals and one or more health related recommendations. In some embodiments, the transmitting operation 2340 may include transmitting the one or more signals associated with comparing the information related to the input associated with the nutraceutical usage and the one or more parameters related to the one or more individuals to substantially similar information related to one or more different individuals.

Figure 24:
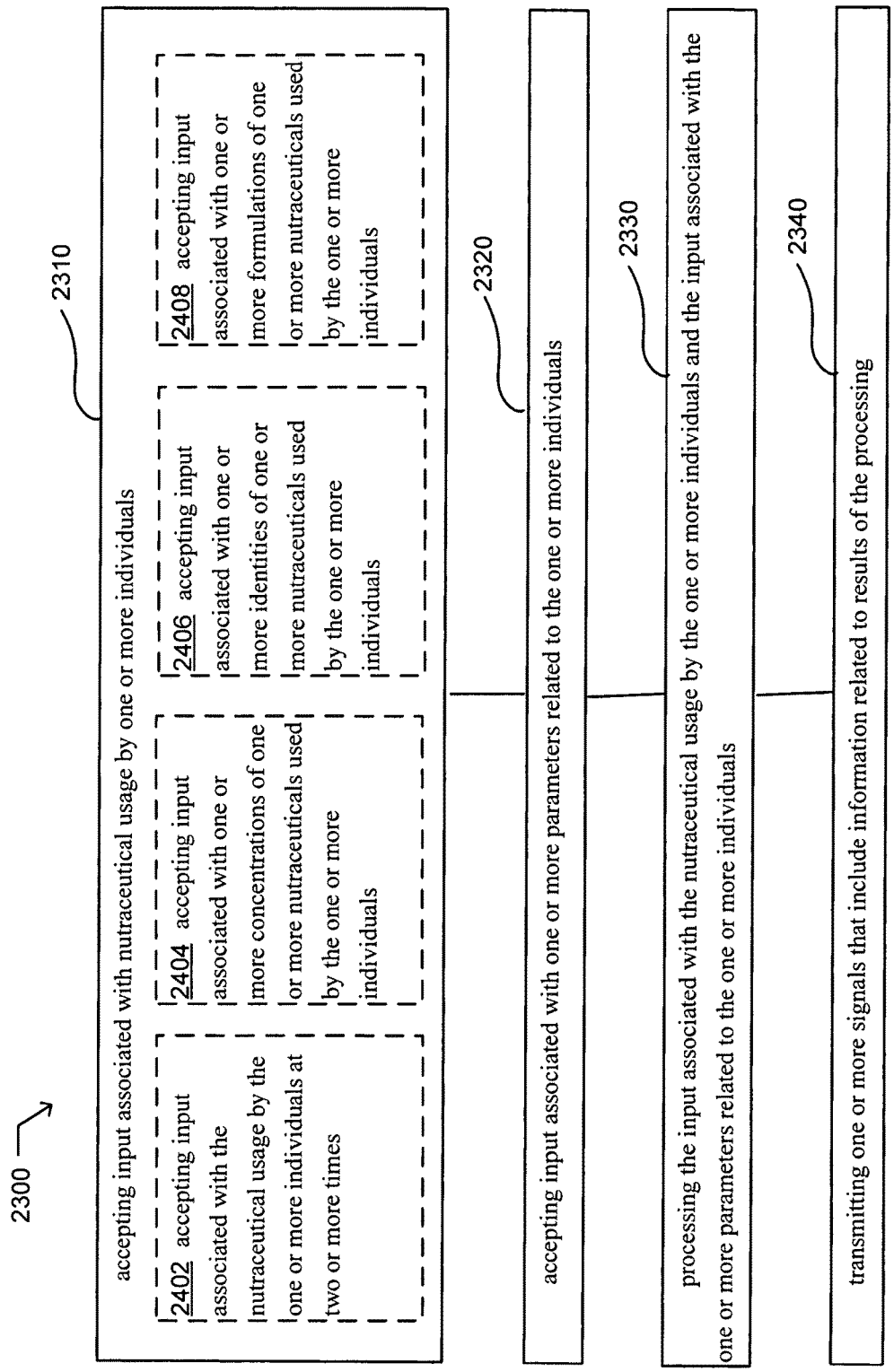
FIG. 24 illustrates alternative embodiments of the example operation flow of FIG. 23.

FIG. 24 illustrates alternative embodiments of the example operational flow 2300 of FIG. 23. FIG. 24 illustrates example embodiments where the accepting operation 2310 may include at least one additional operation. Additional operations may include an operation 2402, an operation 2404, an operation 2406, and/or an operation 2408.

At operation 2402, the accepting operation 2310 may include accepting input associated with the nutraceutical usage by the one or more individuals at two or more times.

In some embodiments, one or more accepting units 110 may accept input associated with nutraceutical usage by one or more individuals at two or more times. In some embodiments, one or more accepting units 110 may accept input associated with nutraceutical usage by one or more individuals at one time.

At operation 2404, the accepting operation 2310 may include accepting input associated with one or more concentrations of one or more nutraceuticals used by the one or more individuals. In some embodiments, one or more accepting units 110 may accept input associated with one or more concentrations of one or more nutraceuticals used by one or more individuals. In some embodiments, one or more accepting units 110 may accept input associated with one or more concentrations of one or more nutraceuticals at the same time. In some embodiments, one or more accepting units 110 may accept input associated with one or more concentrations of one or more nutraceuticals at different times. In some embodiments, one or more accepting units 110 may accept input associated with one or more concentrations of one or more nutraceuticals over a series of time points. In some embodiments, one or more accepting units 110 may accept input associated with one or more concentrations that are expressed as an administered dosage. In some embodiments, one or more accepting units 110 may accept input associated with one or more concentrations of one or more nutraceuticals that are expressed as a systemic concentration of the one or more nutraceuticals within one or more individuals. In some embodiments, one or more accepting units 110 may accept input associated with one or more concentrations of one or more nutraceuticals that are excreted by one or more individuals.

At operation 2406, the accepting operation 2310 may include accepting input associated with one or more identities of one or more nutraceuticals used by the one or more individuals. In some embodiments, one or more accepting units 110 may accept input associated with one or more identities of one or more nutraceuticals used by one or more individuals. In some embodiments, one or more nutraceuticals may be identified by brand name. In some embodiments, one or more nutraceuticals may be identified by chemical name. In some embodiments, one or more nutraceuticals may be identified by popular name.

At operation 2408, the accepting operation 2310 may include accepting input associated with one or more formulations of one or more nutraceuticals used by the one or more individuals. In some embodiments, one or more accepting units 110 may accept input associated with one or more formulations of one or more nutraceuticals used by the one or more individuals. Examples of such formulations include, but are not limited to, formulations that may be administered orally, transdermally, rectally, vaginally, peritoneally, nasally, and the like. In some embodiments, such formulations may include one or more components. For example, in some embodiments, a formulation may include numerous vitamins, minerals, and the like.

Figure 25:
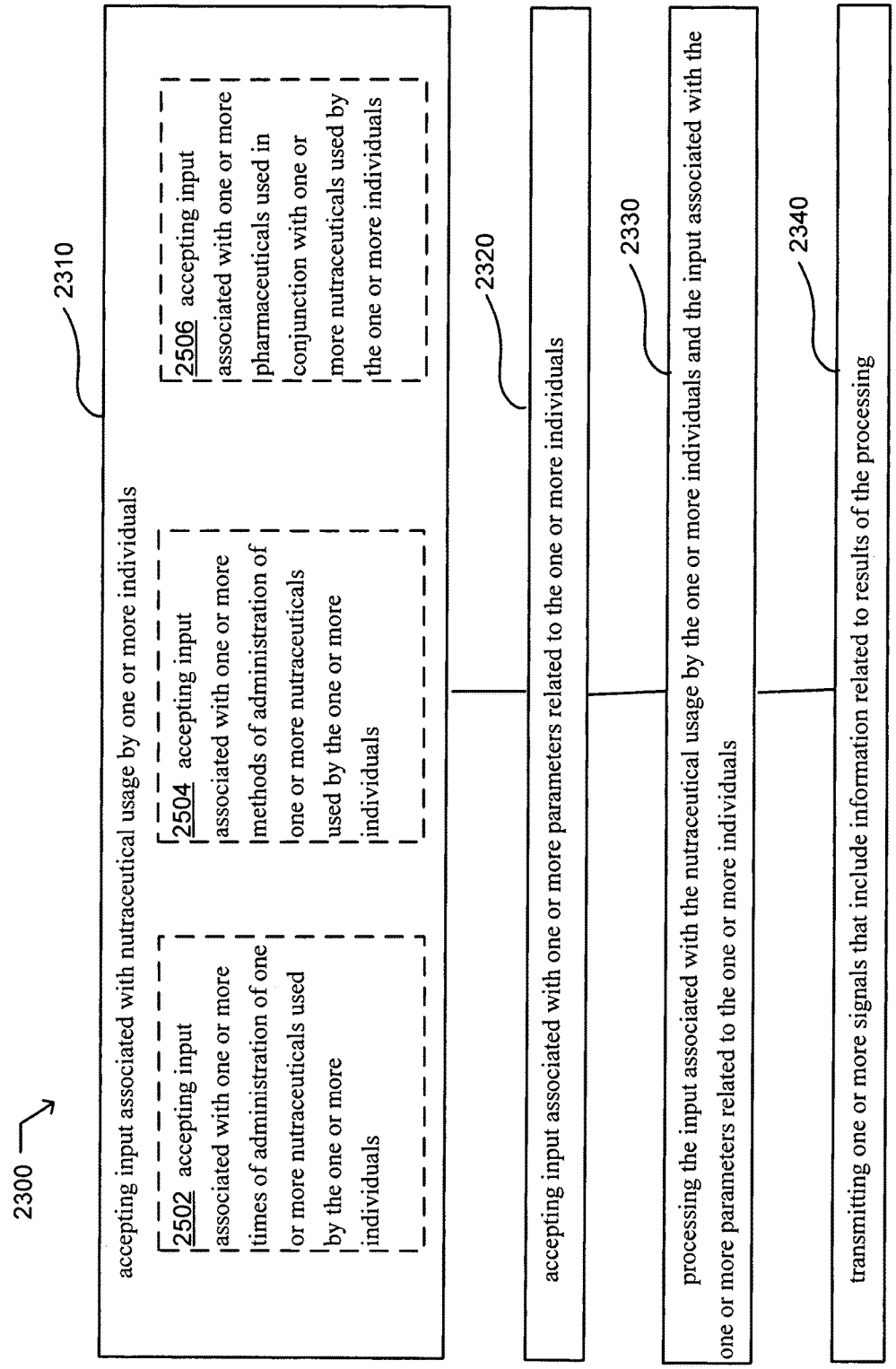
FIG. 25 illustrates alternative embodiments of the example operation flow of FIG. 23.

FIG. 25 illustrates alternative embodiments of the example operational flow 2300 of FIG. 23. FIG. 25 illustrates example embodiments where the accepting operation 2310 may include at least one additional operation. Additional operations may include an operation 2502, an operation 2504, and/or an operation 2506.

At operation 2502, the accepting operation 2310 may include accepting input associated with one or more times of administration of one or more nutraceuticals used by the one or more individuals. In some embodiments, one or more accepting units 110 may accept input associated with one or more times of administration of one or more nutraceuticals used by one or more individuals. For example, in some embodiments, one or more accepting units 110 may accept input associated with multiple administrations of one or more nutraceuticals at multiple times. Accordingly, such input may be used to prepare a presentation showing nutraceutical administration relative to time. In some embodiments, additional information may be combined with times of nutraceutical administration. For example, in some embodiments, time of administration may be combined with the identity of one or more nutraceuticals, the concentration of one or more nutraceuticals, the formulation of one or more nutraceuticals, the route of administration of one or more nutraceuticals, parameters associated with one or more individuals, or substantially any combination thereof.

At operation 2504, the accepting operation 2310 may include accepting input associated with one or more methods of administration of one or more nutraceuticals used by the one or more individuals. In some embodiments, one or more accepting units 110 may accept input associated with one or more methods of administration of one or more nutraceuticals used by one or more individuals. Numerous methods may be used to administer one or more nutraceuticals to one or more individuals. Examples of such methods include, but are not limited to, oral administration, parenteral administration, transdermal administration, nasal administration, sublingual administration, vaginal administration, rectal administration, and the like.

At operation 2506, the accepting operation 2310 may include accepting input associated with one or more pharmaceuticals used in conjunction with one or more nutraceuticals used by the one or more individuals. In some embodiments, one or more accepting units 110 may accept input associated with one or more pharmaceuticals used in conjunction with one or more nutraceuticals used by one or more individuals. One or more accepting units 110 may accept numerous types of input related to pharmaceuticals. Examples of such input include, but are not limited to, route of administration, time of administration, identity of one or more pharmaceuticals, concentration of one or more pharmaceuticals, interactions of one or more pharmaceuticals with other pharmaceuticals and/or nutraceuticals, mechanism of action utilized by one or more pharmaceuticals, and the like.

Figure 26:
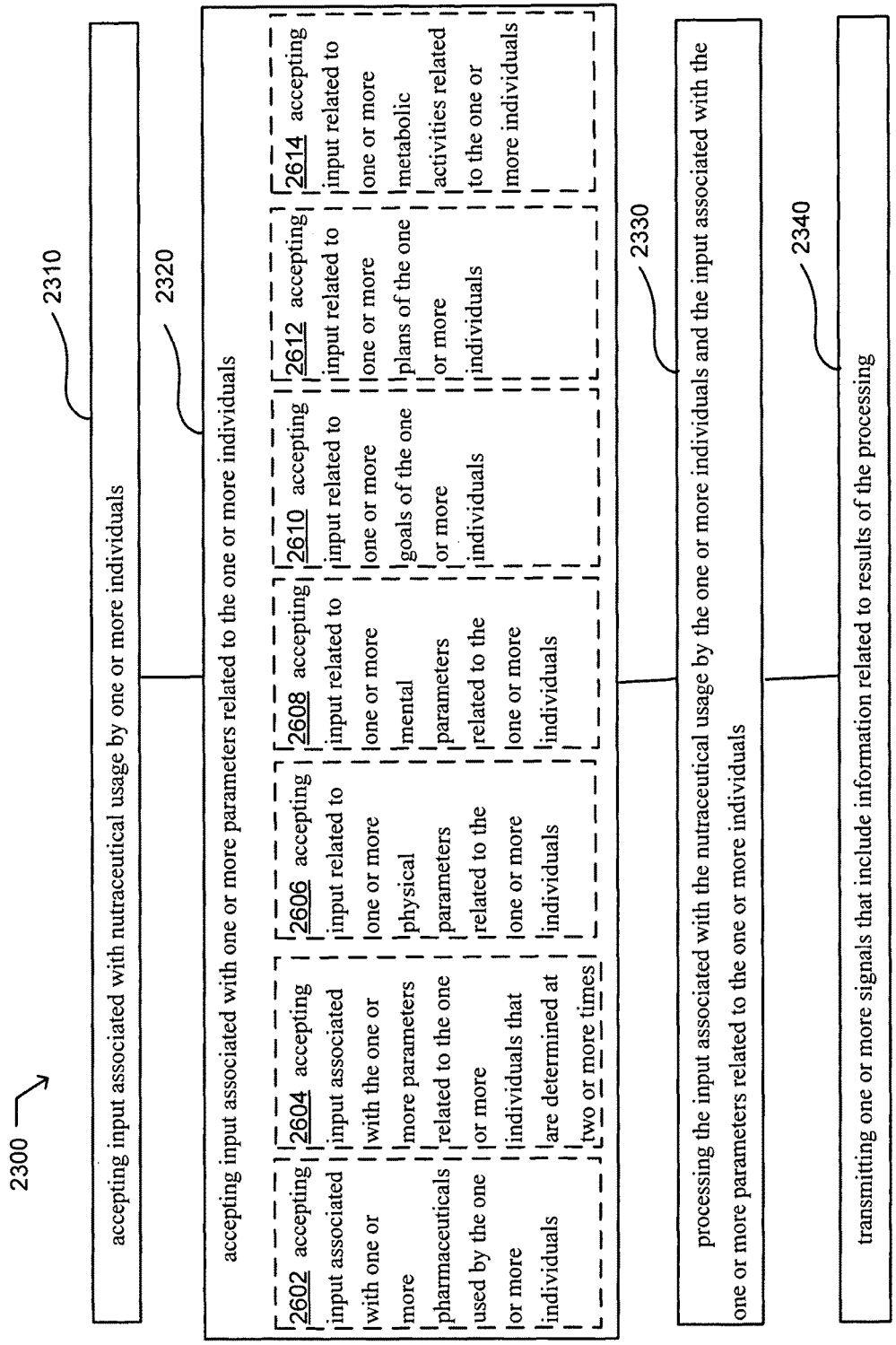
FIG. 26 illustrates alternative embodiments of the example operation flow of FIG. 23.

FIG. 26 illustrates alternative embodiments of the example operational flow 2300 of FIG. 23. FIG. 26 illustrates example embodiments where the accepting operation 2320 may include at least one additional operation. Additional operations may include an operation 2602, an operation 2604, an operation 2606, an operation 2608, an operation 2610, an operation 2612, and/or an operation 2614.

At operation 2602, the accepting operation 2320 may include accepting input associated with one or more pharmaceuticals used by the one or more individuals. In some embodiments, one or more accepting units 110 may accept input associated with one or more pharmaceuticals used by the one or more individuals. In some embodiments, one or more accepting units 110 may accept input associated with the identity of one or more pharmaceuticals. In some embodiments, one or more accepting units 110 may accept input associated with the dosage of one or more pharmaceuticals. In some embodiments, one or more accepting units 110 may accept input associated with contraindications of one or more pharmaceuticals. In some embodiments, one or more accepting units 110 may accept input associated with allergies associated with one or more pharmaceuticals. In some embodiments, one or more accepting units 110 may accept input associated with the duration with which one or more pharmaceuticals are administered. Accordingly, input may include numerous types of information associated with one or more pharmaceuticals.

At operation 2604, the accepting operation 2320 may include accepting input associated with the one or more parameters related to the one or more individuals that are determined at two or more times. In some embodiments, one or more accepting units 110 may accept input associated with one or more parameters related to one or more individuals that are determined at two or more times. One or more accepting units 110 may accept numerous parameters related to one or more individuals. Examples of such parameters include, but are not limited to, physical parameters (e.g., height, weight, age, body composition, blood pressure, heart rate), mental parameters (e.g., depression, happiness, love, hate, loneliness, hopelessness, joy, acquity, memory, alertness), task related parameters (e.g., physical activity, presentation preparation, work related activity), environment related parameters (e.g., travel, allergens, pathogens), goal related parameters (e.g., lower blood pressure, weight loss, sleep acquisition, sleep avoidance, weight gain, muscle gain, fat loss), and the like. In some embodiments, one or more accepting units 110 may accept input at numerous different times. For example, in some embodiments, one or more accepting units 110 may accept physical parameters, such as an individual's weight or body mass index, at numerous time points. Accordingly, such input may be utilized to track changes in one or more parameters over time.

At operation 2606, the accepting operation 2320 may include accepting input related to one or more physical parameters related to the one or more individuals. In some embodiments, one or more accepting units 110 may accept input related to one or more physical parameters related to one or more individuals. One or more accepting units 110 may accept numerous physical parameters. Examples of such physical parameters may include, but are not limited to, height, weight, age, health, disease, physical state, injury, dental health, health history, family health history, and the like.

At operation 2608, the accepting operation 2320 may include accepting input related to one or more mental parameters related to the one or more individuals. In some embodiments, one or more accepting units 110 may accept input related to one or more mental parameters related to one or more individuals. One or more accepting units 110 may accept numerous mental parameters. Examples of such mental parameters may include, but are not limited to, mood (e.g., happiness, sadness, elation, depression, love, hate, loneliness, hopelessness), mental health (e.g., bipolar disorder, schizophrenia, multiple personality disorder, obsessive compulsive disorder, Alzheimer's disease), mental health history, family mental health history, mental function (e.g., alertness, acquity), and the like.

At operation 2610, the accepting operation 2320 may include accepting input related to one or more goals of the one or more individuals. In some embodiments, one or more accepting units 110 may accept input related to one or more goals of one or more individuals. One or more accepting units 110 may accept numerous goal related parameters. Examples of such goal related parameters may include, but are not limited to, athletic performance (e.g., weight gain, weight loss, muscle gain, fat loss, decreased body mass index, endurance, strength), mental performance (e.g., alertness, memory, acuity), and the like.

At operation 2612, the accepting operation 2320 may include accepting input related to one or more plans of the one or more individuals. In some embodiments, one or more accepting units 110 may accept input related to one or more plans of one or more individuals. In some embodiments, one or more accepting units 110 may accept input related to the travel plans of one or more individuals. In some embodiments, one or more accepting units 110 may accept input related to the work plans of one or more individuals. In some embodiments, one or more accepting units 110 may accept input related to the exercise plans of one or more individuals. Accordingly, one or more accepting units 110 may accept input that includes numerous types of information related to the plans of one or more individuals.

At operation 2614, the accepting operation 2320 may include accepting input related to one or more metabolic activities related to the one or more individuals. In some embodiments, one or more accepting units 110 may accept input related to one or more metabolic activities related to one or more individuals. One or more accepting units 110 may accept input related to numerous types of metabolic activity. Examples of input related to metabolic activities include, but are not limited to, respiration rate, enzyme activity, oxygen consumption, heart rate, digestion, fatty acid-oxidation, hormone activity, vasodilation, vasoconstriction, pH, carbon dioxide concentration (e.g., blood, expired), oxygen concentrations (e.g., blood, expired), catabolic reactions, anabolic reactions, lipid metabolism, sugar metabolism, and the like.

Figure 27:
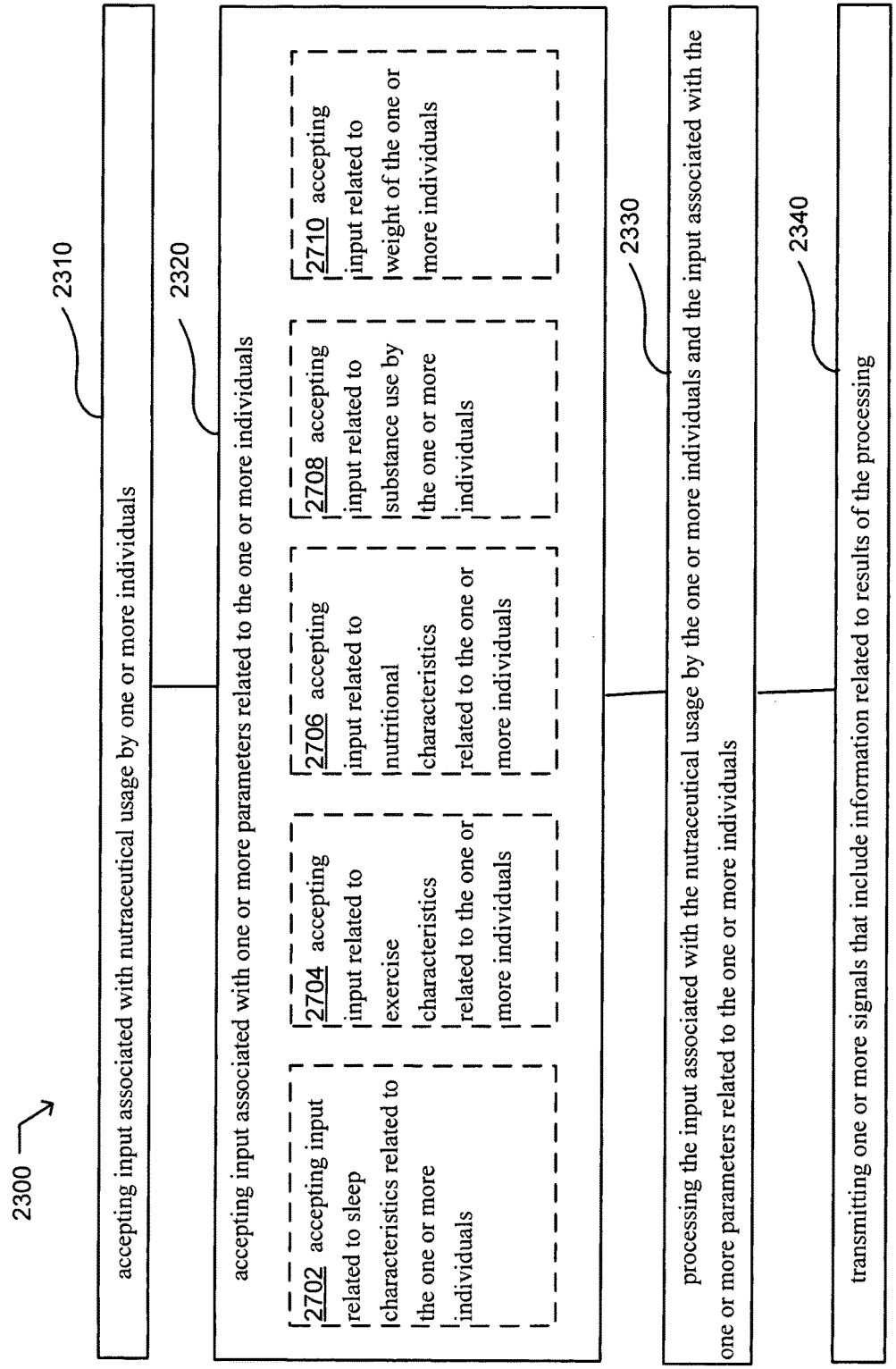
FIG. 27 illustrates alternative embodiments of the example operation flow of FIG. 23.

FIG. 27 illustrates alternative embodiments of the example operational flow 2300 of FIG. 23. FIG. 27 illustrates example embodiments where the accepting operation 2320 may include at least one additional operation. Additional operations may include an operation 2702, an operation 2704, an operation 2706, an operation 2708, and/or an operation 2710.

At operation 2702, the accepting operation 2320 may include accepting input related to sleep characteristics related to the one or more individuals. In some embodiments, one or more accepting units 110 may accept input related to sleep characteristics related to one or more individuals. In some embodiments, one or more input units may accept input related to the number of hours that one or more individuals sleep during a time period. In some embodiments, one or more input units may accept input related to times when one or more individuals sleep during a time period. In some embodiments, one or more input units may accept input related to the sleep schedules of one or more individuals. In some embodiments, one or more input units may accept input related to the quality of sleep obtained by one or more individuals. In some embodiments, one or more input units may accept input related to alertness felt by one or more individuals. In some embodiments, one or more input units may accept input related to sleep characteristics. For example, such input may include information related to positive and/or negative sleep experience, tiredness, restlessness, insomnia, alertness, feelings of tiredness, and the like. Accordingly, one or more input units may accept numerous types of input related to the sleep characteristics of one or more individuals.

At operation 2704, the accepting operation 2320 may include accepting input related to exercise characteristics related to the one or more individuals. In some embodiments, one or more accepting units 110 may accept input related to exercise characteristics related to one or more individuals. Input related to exercise characteristics may include, but is not limited to, type of exercise, duration of exercise, intensity of exercise, frequency of exercise, physiological parameters (e.g., pulse, blood pressure, oxygen consumption, carbon dioxide production) occurring during exercise, and the like.

At operation 2706, the accepting operation 2320 may include accepting input related to nutritional characteristics related to the one or more individuals. In some embodiments, one or more accepting units 110 may accept input related to nutritional characteristics related to one or more individuals. Input related to nutritional characteristics may include, but is not limited to, types of food consumed (e.g., functional foods), types of beverages consumed, number of calories consumed, composition of consumed items (e.g., fat content, cholesterol content, oil content, caloric content), times of consumption, and the like.

At operation 2708, the accepting operation 2320 may include accepting input related to substance use by the one or more individuals. In some embodiments, one or more accepting units 110 may accept input related to substance use by the one or more individuals. Examples of such input include, but are not limited to, alcohol use, tobacco use, nicotine intake, pharmaceutical use, illicit drug use, food supplement use, nutraceutical use, and the like.

At operation 2710, the accepting operation 2320 may include accepting input related to weight of the one or more individuals. In some embodiments, one or more accepting units 110 may accept input related to weight of one or more individuals. One or more accepting units 110 may accept input related to present weight, past weight, future weight goals, or substantially any combination thereof.

Figure 28:
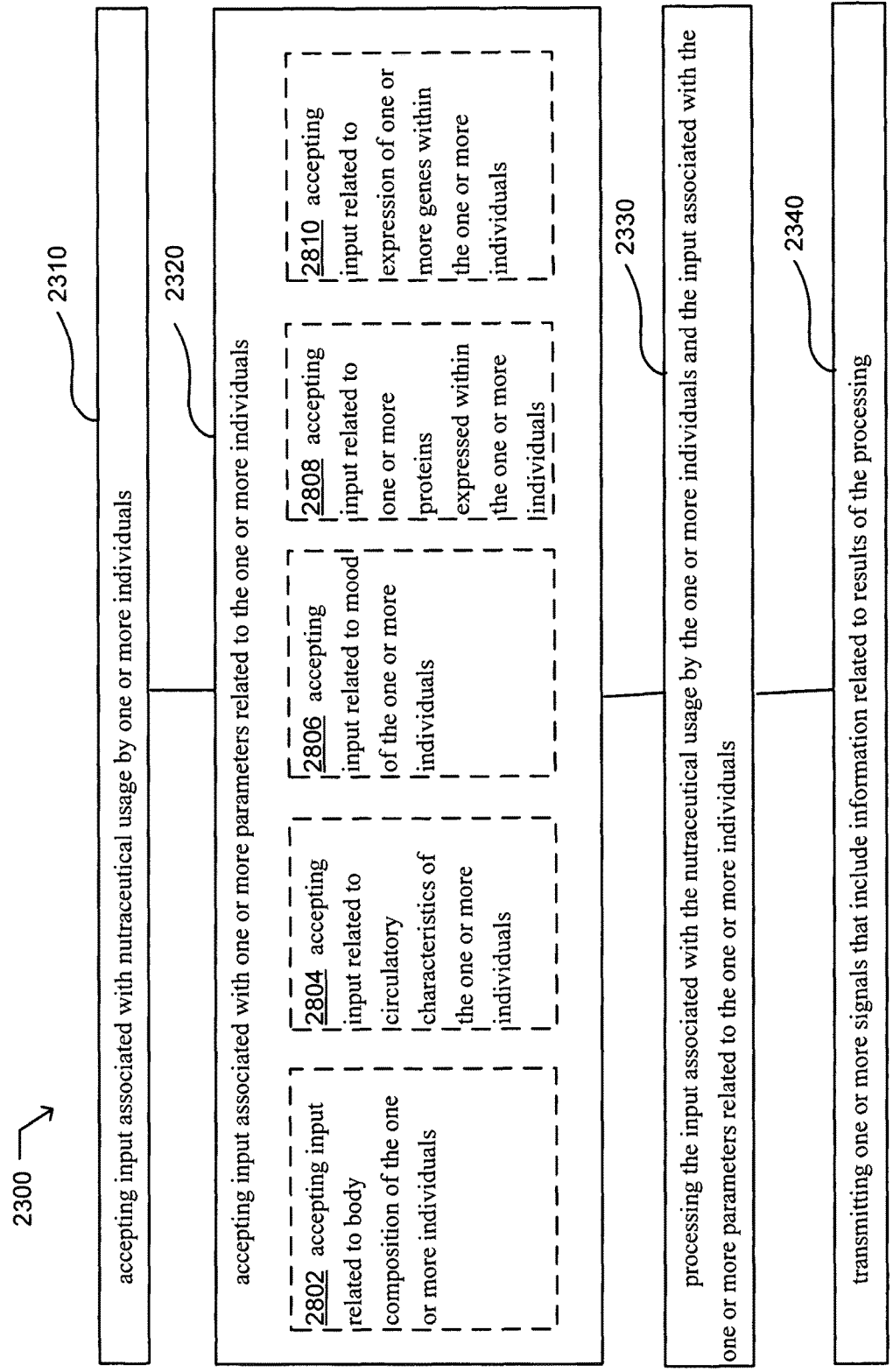
FIG. 28 illustrates alternative embodiments of the example operation flow of FIG. 23.

FIG. 28 illustrates alternative embodiments of the example operational flow 2300 of FIG. 23. FIG. 28 illustrates example embodiments where the accepting operation 2320 may include at least one additional operation. Additional operations may include an operation 2802, an operation 2804, an operation 2806, an operation 2808, and/or an operation 2810.

At operation 2802, the accepting operation 2320 may include accepting input related to body composition of the one or more individuals. In some embodiments, one or more accepting units 110 may accept input related to body composition of one or more individuals. The results from numerous body composition tests may be accepted by one or more accepting units 110. Examples of such tests include, but are not limited to, skinfold measurement, body mass index, waist to hip ratio, hydrostatic weighing, bioelectric impedance, dual-energy X-ray absorptiometry, near infrared interactance, total body potassium, whole-body air-displacement plethysmography, magnetic resonance imaging, total body electrical conductivity, computed tomography, total body protein, or substantially any combination thereof.

At operation 2804, the accepting operation 2320 may include accepting input related to circulatory characteristics of the one or more individuals. In some embodiments, one or more accepting units 110 may accept input related to circulatory characteristics of one or more individuals. One or more accepting units 110 may accept input related to numerous types of circulatory characteristics. Examples of such circulatory characteristics include, but are not limited to, blood pressure, hypertension, heart rate, vasoelasticity, cholesterol levels, coronary heart disease, atherosclerosis, and the like.

At operation 2806, the accepting operation 2320 may include accepting input related to mood of the one or more individuals. In some embodiments, one or more accepting units 110 may accept input related to the mood of one or more individuals. Examples of various moods that may be input include, but are not limited to, happiness, sadness, loneliness, confusion, forgetfulness, joy, glee, euphoria, hopelessness, anger, rage, love, contempt, hate, frustration, and the like.

At operation 2808, the accepting operation 2320 may include accepting input related to one or more proteins expressed within the one or more individuals. In some embodiments, one or more accepting units 110 may accept input related to one or more proteins expressed within one or more individuals. For example, the enzyme 5,10-methylenetetrahydrofolate reductase catalyzes the conversion of 5,10-methylenetetrahydrofolate, required for purine and thymidine syntheses, to 5-methyltetrahydrofolate, the primary circulatory form of folate necessary for methionine synthesis. A common mutation (677C→T) in 5,10-methylenetetrahydrofolate reductase reduces enzyme activity, leading to lower levels of 5-methyltetrahydrofolate. It has been determined that men having adequate folate levels who are homozygous for the mutation (677T/677T)) exhibit a three-fold decrease in risk of colorectal cancer when compared to men having adequate folate levels who are homozygous normal (677C/677C) or heterozygous (677C/677T). However, the protection due to the mutation was absent in men with folate deficiency. In men with the homozygous normal genotype who drink little or no alcohol as reference, men with the homozygous mutation who drink little or no alcohol have an eight-fold decrease in risk and moderate drinkers exhibit a two-fold reduction in risk (Ma et al., Cancer Research, 57:1098-1102 (1997)). Polymorphisms in genes involved in folate metabolism have also been linked to maternal risk factors for Down Syndrome, neural tube defects, and oral clefts (Mills et al., Am. J. Med. Genet., 86:71-74 (1999); Wilson et al., Mol. Genet. Metab., 67:317-323 (1999); Hobbs et al., Am. J. Med. Genet., 67:623-630 (2000)). Accordingly, in some embodiments, information related to production of one or more proteins within an individual may be input. Such information may be used during the selection of nutraceuticals for administration to an individual. Such information may also be used to suggest health-related information. In some embodiments, one or more accepting units 110 may accept input related to the concentration of one or more proteins expressed within an individual. In some embodiments, one or more accepting units 110 may accept input related to the activity of one or more proteins expressed within an individual. Accordingly, one or more accepting units 110 may accept information related to numerous proteins and properties of proteins expressed within an individual.

At operation 2810, the accepting operation 2320 may include accepting input related to expression of one or more genes within the one or more individuals. In some embodiments, one or more accepting units 110 may accept input related to expression of one or more genes within one or more individuals. In some embodiments, such information may be used during the selection of nutraceuticals for administration to an individual. Such information may also be used to suggest health-related information. For example, folate status and common variations in genes that code for folate dependent enzymes are linked to many types of cancer, vascular disease, birth defects, and complications of pregnancy. This arises because several molecular mechanisms that underpin the genomic machinery are sensitive to B vitamin status and, in particular, are responsive to the interaction between folate nutrition and folate dependent enzyme polymorphisms (Lucock, B M J, 328:211-214 (2004)). Accordingly, genetic information may be utilized during the selection of one or more nutraceuticals for administration to an individual. In another example, black tea polyphenols (e.g., a theaflavin-3-monogallate and theaflavin-3'-monogallate mixture) have been shown to suppress cyclooxygenase 2 (Cox-2) gene expression at both the messenger ribonucleic acid and protein level (Lu et al., Cancer Reserch, 60:6465-6471 (2000)). Pharmacological inhibition of COX can provide relief from the symptoms of inflammation and pain. Accordingly, in some embodiments, input related to COX gene expression may be accepted by one or more accepting units 110 to follow nutraceutical mediated inhibition of COX expression. Black tea extracts also exhibit chemoprotective activity (Lu et al., Cancer Reserch, 60:6465-6471 (2000)). In another example, a resveratrol analog (3,4,5,4'-tetrahydroxystilbene) has been shown to differentially induce pro-apoptotic p53/Bax gene expression and inhibit the growth of transformed cells but not their normal counterparts (Lu et al., Carcinogenesis, 22:321-328 (2001)). Accordingly, p53/Bax gene expression may be input to follow resveratrol analog mediated induction of gene expression. Numerous nutraceuticals mediate induction or inhibition of gene expression (e.g., Chen et al., Cancer Letters, 129:173-179 (1998); British J. Cancer, 92:513-521 (2005)). In another example, dietary omega-3 polyunsaturated fatty acids were shown to affect brain gene expression (Kitajka et al., PNAS, 101:10931-10936 (2004)). In some embodiments, one or more accepting units 110 may accept input related to the expression level of one or more genes within an individual. In some embodiments, one or more accepting units 110 may accept input related to the activity of one or more gene products expressed within an individual. Accordingly, one or more accepting units 110 may accept information related to numerous genes and the products of gene expression within an individual.

Figure 29:
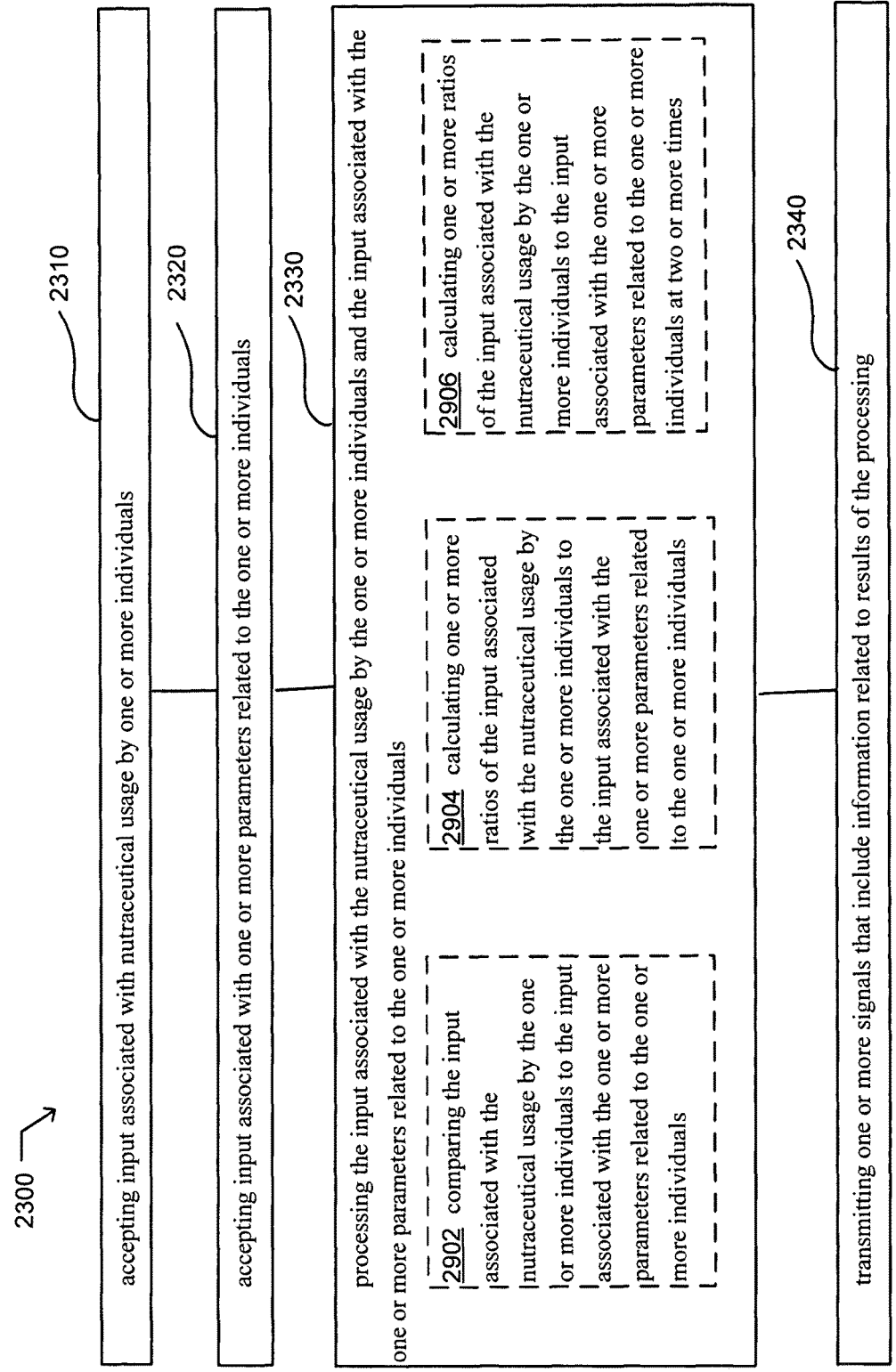
FIG. 29 illustrates alternative embodiments of the example operation flow of FIG. 23.

FIG. 29 illustrates alternative embodiments of the example operational flow 2300 of FIG. 23. FIG. 29 illustrates example embodiments where the processing operation 2330 may include at least one additional operation. Additional operations may include an operation 2902, an operation 2904, and/or an operation 2906.

At operation 2902, the processing operation 2330 may include comparing the input associated with the nutraceutical usage by the one or more individuals to the input associated with the one or more parameters related to the one or more individuals. In some embodiments, one or more computational units 120 may compare input associated with nutraceutical usage by one or more individuals to input associated with one or more parameters related to the one or more individuals. One or more computational units 120 may compare numerous types of input associated with nutraceutical usage and numerous types of input associated with parameters related to one or more individuals. For example, in some embodiments, serotonin usage may be compared with the amount of sleep obtained by an individual. In some embodiments, caffeine usage may be compared with the amount of sleep obtained by an individual. In some embodiments, 5-hydroxytryptophan usage may be compared to the mood of an individual. In some embodiments, lithium usage may be compared to suppression of antipsychotic symptoms. In some embodiments, one or more computational units 120 may compare numerous types of input associated with nutraceutical usage and numerous types of input associated with parameters related to one individual. In some embodiments, one or more computational units 120 may compare numerous types of input associated with nutraceutical usage and numerous types of input associated with parameters related to more than one individual. In some embodiments, one or more computational units 120 may compare numerous types of input associated with nutraceutical usage and numerous types of input associated with parameters related to one individual to one or more other individuals. For example, in some embodiments, nutraceutical usage and parameters associated with an individual may be compared to nutraceutical usage and parameters associated with one or more other individuals.

At operation 2904, the processing operation 2330 may include calculating one or more ratios of the input associated with the nutraceutical usage by the one or more individuals to the input associated with the one or more parameters related to the one or more individuals. In some embodiments, one or more computational units 120 may calculate one or more ratios of input associated with nutraceutical usage by one or more individuals to input associated with one or more parameters related to the one or more individuals. For example, in some embodiments, one or more computational units 120 may calculate the ratio of nutraceutical dosage (e.g., hoodia) to a determined parameter (e.g., weight loss) at one or more given times. In such instances, the individual ratios could be plotted over time to determine if there was a correlation of nutraceutical usage and the parameter (e.g., weight loss). In some embodiments, such ratios related to an individual could be compared to substantially similar ratios related to other individuals. Such a comparison would allow an individual to compare themselves to other individuals. Numerous different types of nutraceutical usages and parameters may be used during the calculation of ratios.

At operation 2906, the processing operation 2330 may include calculating one or more ratios of the input associated with the nutraceutical usage by the one or more individuals to the input associated with the one or more parameters related to the one or more individuals at two or more times. In some embodiments, one or more computational units 120 may calculate one or more ratios of input associated with nutraceutical usage by one or more individuals to input associated with one or more parameters related to the one or more individuals at two or more times. In some embodiments, the ratio of nutraceutical usage and one or more parameters can be compared at two or more times to determine if nutraceutical usage affects the one or more parameters. In some embodiments, the ratio of nutraceutical usage and one or more parameters can be compared at two or more times to titrate the dosage of the one or more nutraceuticals relative to one or more parameters. In some embodiments, the ratio of nutraceutical usage and one or more parameters can be compared at two or more times to determine if nutraceutical usage affects the one or more parameters. In some embodiments, one or more ratios related to one individual may be compared to substantially similar ratios related to one or more other individuals.

Figure 30:
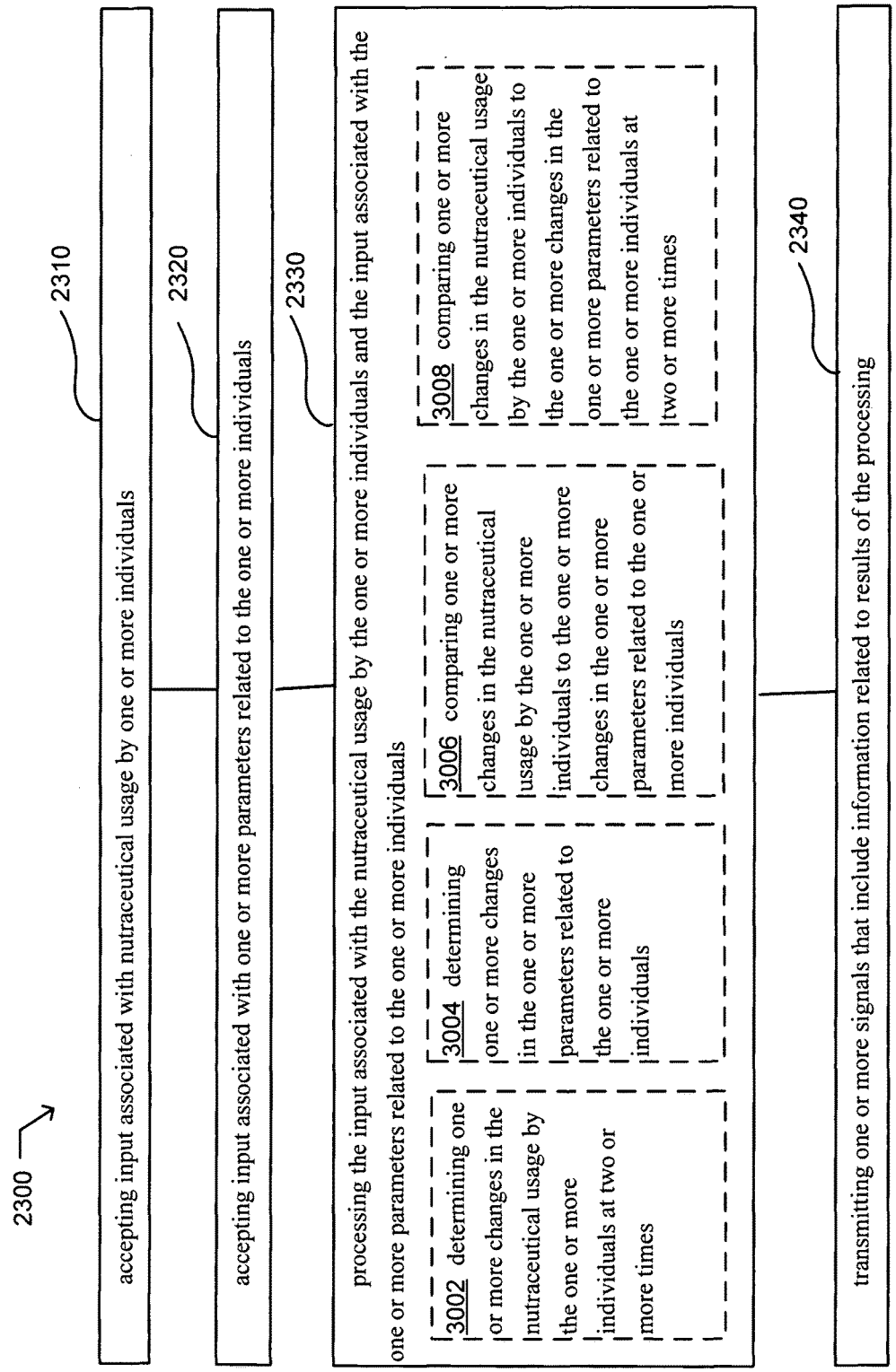
FIG. 30 illustrates alternative embodiments of the example operation flow of FIG. 23.

FIG. 30 illustrates alternative embodiments of the example operational flow 2300 of FIG. 23. FIG. 30 illustrates example embodiments where the processing operation 2330 may include at least one additional operation. Additional operations may include an operation 3002, an operation 3004, an operation 3006, and/or an operation 3008.

At operation 3002, the processing operation 2330 may include determining one or more changes in the nutraceutical usage by the one or more individuals at two or more times. In some embodiments, one or more computational units 120 may determine one or more changes in nutraceutical usage by one or more individuals at two or more times. For example, in some embodiments, an individual may change the dosage of one or more nutraceuticals. In some embodiments, an individual may change the identity of one or more nutraceuticals. In some embodiments, an individual may change the route of administration of one or more nutraceuticals. In some embodiments, an individual may change the time of administration of one or more nutraceuticals. Accordingly, in some embodiments, one or more computational units 120 may determine one or more changes in nutraceutical usage and correlate the change in nutraceutical usage with one or more changes in one or more parameters related to one or more individuals. For example, in some embodiments, changes in serotonin usage (e.g., dosage, time of administration) may be correlated with sleep acquisition by an individual. In some embodiments, changes in 5-hydroxytryptophan usage may be correlated with the mood of an individual. Numerous changes in nutraceutical usage may be determined and correlated to one or more parameters related to an individual.

At operation 3004, the processing operation 2330 may include determining one or more changes in the one or more parameters related to the one or more individuals. In some embodiments, one or more computational units 120 may determine one or more changes in one or more parameters related to one or more individuals. Examples of parameters that may change include, but are not limited to, physical parameters, mental parameters, physiological parameters, and the like. In some embodiments, changes in one or more parameters may be correlated to nutraceutical usage by an individual. In some embodiments, changes in one or more parameters may be correlated to changes in nutraceutical usage by an individual.

At operation 3006, the processing operation 2330 may include comparing one or more changes in the nutraceutical usage by the one or more individuals to the one or more changes in the one or more parameters related to the one or more individuals. In some embodiments, one or more computational units 120 may compare one or more changes in nutraceutical usage by one or more individuals to one or more changes in one or more parameters related to the one or more individuals. Numerous changes in nutraceutical usage may be compared. Examples of such changes in nutraceutical usage include, but are not limited to, dosage, time of administration, route of administration, formulation, manufacturer, and the like. Numerous changes in parameters may be compared. Examples of such changes in parameters include, but are not limited to, mental parameters, physical parameters, social parameters, sleep parameters, and the like. In some embodiments, one or more changes in nutraceutical usage by an individual may be compared to changes in one or more parameters related to the individual. In some embodiments, one or more changes in nutraceutical usage by an individual may be compared to changes in one or more parameters related to one or more other individuals. For example, in some embodiments, an individual may determine how a change in their personal nutraceutical usage changes one or more parameters when compared to a substantially similar change by one or more other individuals. In some embodiments, one or more computational units 120 may compare the nutraceutical usage by an individual to one or more changes in one or more parameters related to the individual and also to substantially similar changes in one or more other individuals to suggest a course of nutraceutical usage for the individual. For example, in some embodiments, the computational unit 120 may suggest a higher dosage of one or more nutraceuticals for administration to an individual if it is determined that a higher dosage will produce an effect based on changes resulting in one or more other individuals. Numerous comparisons may be made by one or more computational units 120.

At operation 3008, the processing operation 2330 may include comparing one or more changes in the nutraceutical usage by the one or more individuals to the one or more changes in the one or more parameters related to the one or more individuals at two or more times. In some embodiments, one or more computational units 120 may compare one or more changes in nutraceutical usage by one or more individuals to one or more changes in one or more parameters related to one or more individuals at two or more times. Numerous changes in nutraceutical usage may be compared. Examples of such changes in nutraceutical usage include, but are not limited to, dosage, time of administration, route of administration, formulation, manufacturer, and the like. Numerous changes in parameters may be compared. Examples of such changes in parameters include, but are not limited to, mental parameters, physical parameters, social parameters, sleep parameters, and the like.

Figure 31:
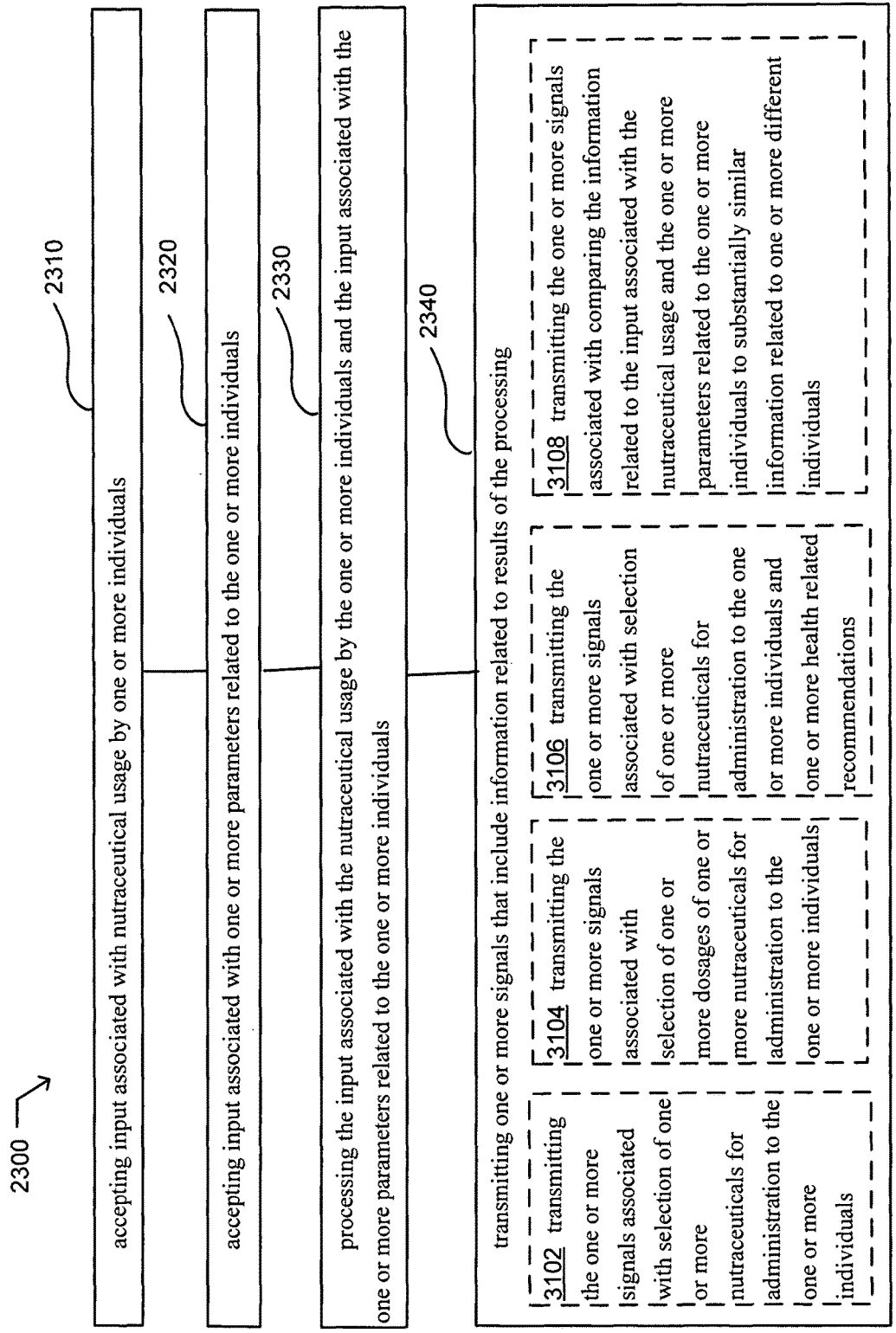
FIG. 31 illustrates alternative embodiments of the example operation flow of FIG. 23.

FIG. 31 illustrates alternative embodiments of the example operational flow 2300 of FIG. 23. FIG. 31 illustrates example embodiments where the transmitting operation 2340 may include at least one additional operation. Additional operations may include an operation 3102, an operation 3104, an operation 3106, and/or an operation 3108.

At operation 3102, the transmitting operation 2340 may include transmitting the one or more signals associated with selection of one or more nutraceuticals for administration to the one or more individuals. In some embodiments, one or more transmitting units 140 may transmit one or more signals associated with selection of one or more nutraceuticals for administration to one or more individuals. In some embodiments, one or more transmitting units 140 may transmit one or more signals associated with the identity of one or more nutraceuticals for administration to one or more individuals.

At operation 3104, the transmitting operation 2340 may include transmitting the one or more signals associated with selection of one or more dosages of one or more nutraceuticals for administration to the one or more individuals. In some embodiments, one or more transmitting units 140 may transmit one or more signals associated with selection of one or more dosages of one or more nutraceuticals for administration to one or more individuals.

At operation 3106, the transmitting operation 2340 may include transmitting the one or more signals associated with selection of one or more nutraceuticals for administration to the one or more individuals and one or more health related recommendations. In some embodiments, one or more transmitting units 140 may transmit one or more signals associated with selection of one or more nutraceuticals for administration to the one or more individuals and one or more health related recommendations. Examples of health related recommendations may include, but are not limited to, recommendations associated with diet, sleep habits, substance use, weight, exercise, and the like.

At operation 3108, the transmitting operation 2340 may include transmitting the one or more signals associated with comparing the information related to the input associated with the nutraceutical usage and the one or more parameters related to the one or more individuals to substantially similar information related to one or more different individuals. In some embodiments, one or more transmitting units 140 may transmit one or more signals associated with comparing information related to input associated with nutraceutical usage and one or more parameters related to one or more individuals to substantially similar information related to one or more different individuals.

Figure 32:
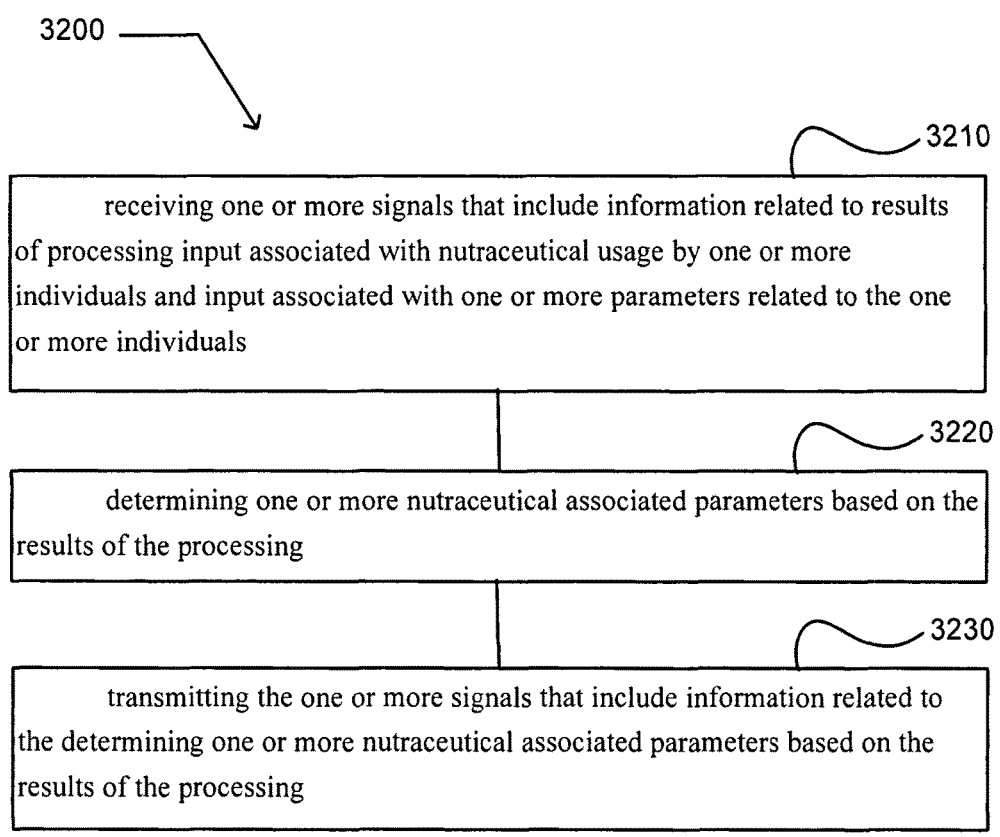
FIG. 32 illustrates an operational flow 3200 representing example operations related to receiving, determining and transmitting input related to one or more nutraceuticals.

FIG. 32 illustrates an operational flow 3200 representing examples of operations that are related to the performance of one or more methods related to one or more nutraceuticals. In FIG. 32 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 3200 includes a receiving operation 3210 involving receiving one or more signals that include information related to results of processing input associated with nutraceutical usage by one or more individuals and input associated with one or more parameters related to the one or more individuals. In some embodiments, the receiving operation 3210 may include receiving the one or more signals associated with selection of one or more nutraceuticals for administration to the one or more individuals. In some embodiments, the receiving operation 3210 may include receiving the one or more signals associated with selection of one or more dosages of one or more nutraceuticals for administration to the one or more individuals. In some embodiments, the receiving operation 3210 may include receiving the one or more signals associated with selection of one or more nutraceuticals for administration to the one or more individuals and one or more health related recommendations. In some embodiments, the receiving operation 3210 may include receiving the one or more signals associated with comparing the information related to the input associated with the nutraceutical usage and the one or more parameters related to the one or more individuals to substantially similar information related to one or more different individuals.

After a start operation, the operational flow 3200 includes a determining operation 3220 involving determining one or more nutraceutical associated parameters based on the results of the processing. In some embodiments, the determining operation 3220 may include determining one or more nutraceuticals for administration to the one or more individuals. In some embodiments, the determining operation 3220 may include determining one or more concentrations of one or more nutraceuticals for administration to the one or more individuals. In some embodiments, the determining operation 3220 may include determining one or more nutraceutical formulations for administration to the one or more individuals. In some embodiments, the determining operation 3220 may include determining one or more health related recommendations for the one or more individuals.

After a start operation, the operational flow 3200 may include a transmitting operation 3230 involving transmitting the one or more signals that include information related to the determining one or more nutraceutical associated parameters based on the results of the processing. In some embodiments, the transmitting operation 3230 may include transmitting the one or more signals that include information related to one or more nutraceuticals for administration to the one or more individuals. In some embodiments, the transmitting operation 3230 may include transmitting the one or more signals that include information related to one or more concentrations of one or more nutraceuticals for administration to the one or more individuals. In some embodiments, the transmitting operation 3230 may include transmitting the one or more signals that include information related to one or more nutraceutical formulations for administration to the one or more individuals. In some embodiments, the transmitting operation 3230 may include transmitting the one or more signals that include information related to one or more health related recommendations for the one or more individuals.

Figure 33:
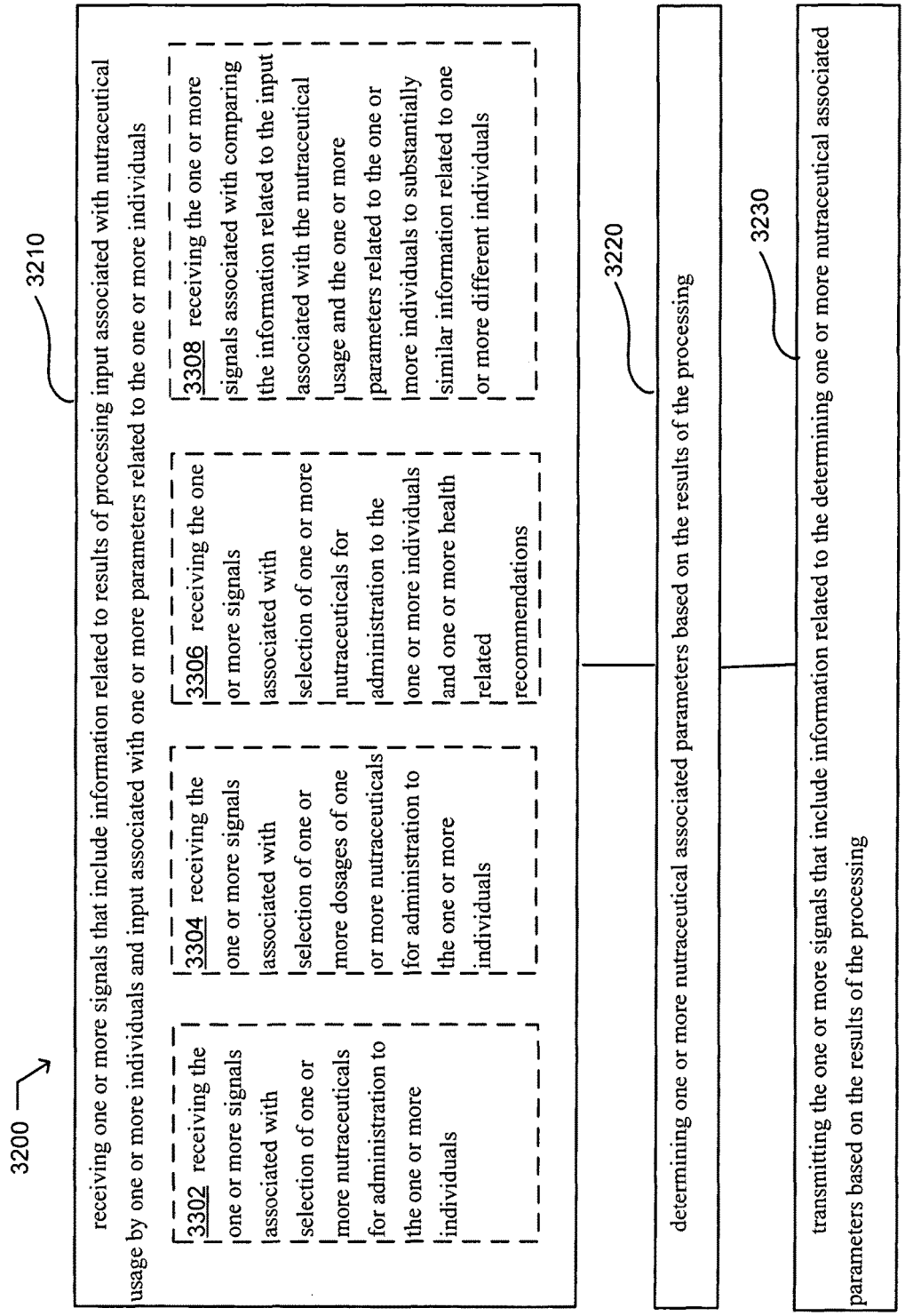
FIG. 33 illustrates alternative embodiments of the example operation flow of FIG. 32.

FIG. 33 illustrates alternative embodiments of the example operational flow 3200 of FIG. 32. FIG. 33 illustrates example embodiments where the receiving operation 3210 may include at least one additional operation. Additional operations may include an operation 3302, an operation 3304, an operation 3306, and/or an operation 3308.

At operation 3302, the receiving operation 3210 may include receiving the one or more signals associated with selection of one or more nutraceuticals for administration to the one or more individuals. In some embodiments, one or more receiving units 150 may receive one or more signals associated with selection of one or more nutraceuticals for administration to one or more individuals. One or more signals may include numerous types of information that may be used during the selection of one or more nutraceuticals for administration to one or more individuals. Examples of such information may include, but are not limited to, mental parameters associated with an individual, physical parameters associated with an individual, social parameters associated with an individual, physiological parameters associated with an individual, and the like. Examples of parameters may include, but are not limited to, height, weight, age, fitness level, body mass index, body composition, sleep habits, substance usage, goals, medical history, allergies, and the like.

At operation 3304, the receiving operation 3210 may include receiving the one or more signals associated with selection of one or more dosages of one or more nutraceuticals for administration to the one or more individuals. In some embodiments, one or more receiving units 150 may receive one or more signals associated with selection of one or more dosages of one or more nutraceuticals for administration to one or more individuals. In some embodiments, one or more signals may include information related to parameters associated with an individual. Examples of such parameters include, but are not limited to, height, weight, metabolism, activity level, goals, schedule, occupation, and the like.

At operation 3306, the receiving operation 3210 may include receiving the one or more signals associated with selection of one or more nutraceuticals for administration to the one or more individuals and one or more health related recommendations. In some embodiments, one or more receiving units 150 may receive one or more signals associated with selection of one or more nutraceuticals for administration to one or more individuals and one or more health related recommendations. One or more signals may include numerous types of information that may be used during the selection of one or more nutraceuticals for administration to one or more individuals. Examples of such information may include, but are not limited to, mental parameters associated with an individual, physical parameters associated with an individual, social parameters associated with an individual, physiological parameters associated with an individual, and the like. Examples of such parameters may include, but are not limited to, height, weight, age, fitness level, body mass index, body composition, sleep habits, substance usage, goals, medical history, allergies, and the like. One or more signals may also include information related to one or more health related recommendations. For example, in some embodiments, one or more signals may include information related to the weight, body mass index, and body fat percentage of an individual. Accordingly, such information may be used to determine nutraceuticals, a diet plan, and an exercise plan that may be used by an individual to reach a fitness goal. In some embodiments, one or more signals may include information related to sleep habits, stimulant consumption, work habits, schedule, and the like. Such information may be used to suggest one or more nutraceuticals and a sleep schedule that may be used by an individual to improve their sleep acquisition.

At operation 3308, the receiving operation 3210 may include receiving the one or more signals associated with comparing the information related to the input associated with the nutraceutical usage and the one or more parameters related to the one or more individuals to substantially similar information related to one or more different individuals. In some embodiments, one or more receiving units 150 may receive one or more signals associated with comparing information related to input associated with nutraceutical usage and one or more parameters related to one or more individuals to substantially similar information related to one or more different individuals. In some embodiments, one or more signals include information that provides for comparison of an individual's nutraceutical usage and parameters associated with the individual with nutraceutical usage and parameters associated with one or more other individuals. Accordingly, the one or more signals may be used to improve an individual's nutraceutical usage through use of substantially similar information associated with other individuals.

Figure 34:
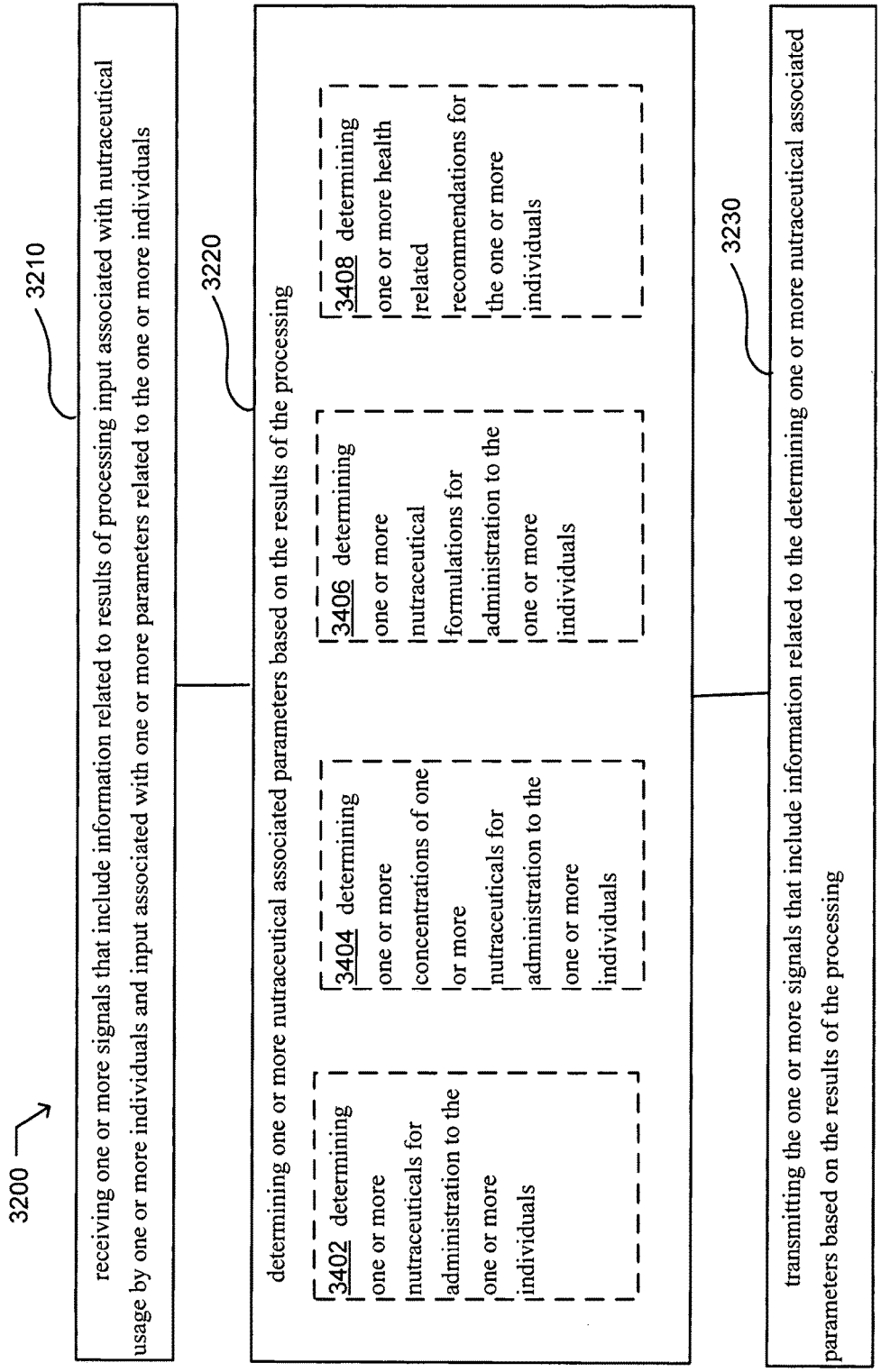
FIG. 34 illustrates alternative embodiments of the example operation flow of FIG. 32.

FIG. 34 illustrates alternative embodiments of the example operational flow 3200 of FIG. 32. FIG. 33 illustrates example embodiments where the determining operation 3220 may include at least one additional operation. Additional operations may include an operation 3402, an operation 3404, an operation 3406, and/or an operation 3408.

At operation 3402, the determining operation 3220 may include determining one or more nutraceuticals for administration to the one or more individuals. In some embodiments, one or more determining units may determine one or more nutraceuticals for administration to one or more individuals. In some embodiments, one or more determining units may utilize input associated with nutraceutical usage and one or more parameters related to an individual to determine one or more nutraceuticals for administration to the individual. For example, in some embodiments, one or more determining units may select one or more nutraceuticals that do not contraindicate one or more pharmaceuticals being used by an individual. In some embodiments, one or more determining units may select one or more nutraceuticals that do not contraindicate one or more other nutraceuticals that are being used by an individual. In some embodiments, one or more determining units may select one or more nutraceuticals to attain one or more goals of the individual (e.g., weight loss, sleep acquisition, alertness, mood alteration, hormonal balance, weight gain). In some embodiments, one or more determining units may select one or more nutraceuticals in accordance with the propensity of an individual to develop a malady. For example, in some embodiments, one or more determining units may select calcium supplements for administration to persons who exhibit symptoms of, or who may be at risk of developing, osteoporosis. In some embodiments, one or more determining units may select one or more nutraceuticals with consideration given to time. For example, in some embodiments, an individual may exhibit serotonin levels that are inconsistent with sleep acquisition during desired hours by an individual. Accordingly, one or more determining units may determine one or more nutraceuticals for use by an individual to increase sleep acquisition. In some embodiments, the one or more determining units may select one or more nutraceuticals and suggest one or times for administration to an individual. Numerous nutraceuticals and administration schemes may be determined by one or more determining units.

At operation 3404, the determining operation 3220 may include determining one or more concentrations of one or more nutraceuticals for administration to the one or more individuals. In some embodiments, one or more determining units may determine one or more concentrations of one or more nutraceuticals for administration to one or more individuals. In some embodiments, one or more determining units may utilize input associated with nutraceutical usage and one or more parameters related to an individual to determine one or more concentrations of one or more nutraceuticals for administration to the individual. One or more determining units may utilize numerous types of parameters. Examples of such parameters include, but are not limited to, weight, metabolism, activity level, exercise habits, goals, and the like. For example, in some embodiments, one or more determining units may determine that a higher dosage of a nutraceutical is appropriate for a larger person and a lower dosage is appropriate for a smaller person. In some embodiments, one or more determining units may determine one or more concentrations of one or more nutraceuticals to be within a range of concentrations. For example, in some embodiments, one or more determining units may determine a range of concentrations of melotonin for administration to an individual that enable the individual to acquire a desired amount of sleep without causing the individual to be drowsy during daytime hours. Accordingly, one or more determining units may determine numerous concentrations of numerous types of nutraceuticals for administration to an individual.

At operation 3406, the determining operation 3220 may include determining one or more nutraceutical formulations for administration to the one or more individuals. In some embodiments, one or more determining units may determine one or more nutraceutical formulations for administration to one or more individuals. In some embodiments, one or more determining units may utilize input associated with nutraceutical usage and one or more parameters related to an individual to determine one or more nutraceutical formulations for administration to the individual. Numerous formulations may be selected. Examples of such formulations include, but are not limited to, sublingual formulations, oral formulations, transdermal formulations, cream-based formulations, suppositories, inhaled formulations, nasally administered formulations, and the like.

At operation 3408, the determining operation 3220 may include determining one or more health related recommendations for the one or more individuals. In some embodiments, one or more determining units may determine one or more health related recommendations for one or more individuals. In some embodiments, one or more determining units may utilize input associated with nutraceutical usage and one or more parameters related to an individual to determine one or more health related recommendations for one or more individuals. Examples of health related recommendations include, but are not limited to, recommendations related to eating habits, substance use, exercise, physical activities, sleep acquisition, and the like.

Figure 35:
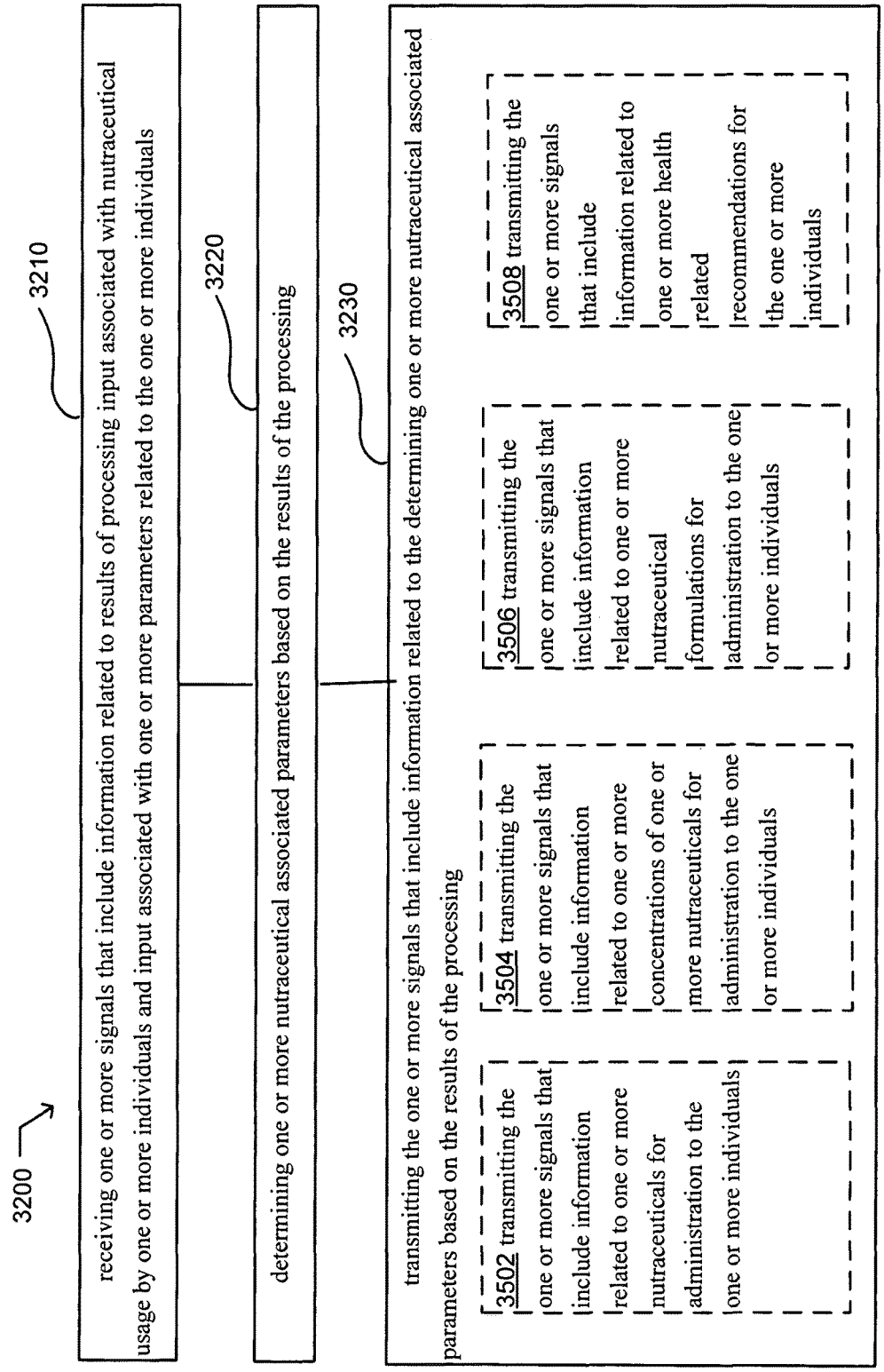
FIG. 35 illustrates alternative embodiments of the example operation flow of FIG. 32.

FIG. 35 illustrates alternative embodiments of the example operational flow 3200 of FIG. 32. FIG. 35 illustrates example embodiments where the transmitting operation 3230 may include at least one additional operation. Additional operations may include an operation 3502, an operation 3504, an operation 3506, and/or an operation 3508.

At operation 3502, the transmitting operation 3230 may include transmitting the one or more signals that include information related to one or more nutraceuticals for administration to the one or more individuals. In some embodiments, one or more transmitting units 140 may transmit one or more signals that include information related to one or more nutraceuticals for administration to one or more individuals. In some embodiments, one or more transmitting units 140 may transmit one or more signals that include information related to determining one or more nutraceutical associated parameters based on the results of processing. In some embodiments, one or more transmitting units 140 may transmit one or more signals that include information related to the identity of one or more nutraceuticals for administration to an individual. In some embodiments, one or more transmitting units 140 may transmit one or more signals that include information related to one or more times of administration for one or more nutraceuticals to an individual. In some embodiments, one or more transmitting units 140 may transmit one or more signals that include information related to the concentration of one or more nutraceuticals for administration to an individual. Accordingly, numerous types of information may be transmitted by one or more transmitting units 140.

At operation 3504, the transmitting operation 3230 may include transmitting the one or more signals that include information related to one or more concentrations of one or more nutraceuticals for administration to the one or more individuals. In some embodiments, one or more transmitting units 140 may transmit one or more signals that include information related to one or more concentrations of one or more nutraceuticals for administration to one or more individuals. In some embodiments, one or more transmitting units 140 may transmit one or more signals that include information related to determining one or more nutraceutical associated parameters based on the results of processing.

At operation 3506, the transmitting operation 3230 may include transmitting the one or more signals that include information related to one or more nutraceutical formulations for administration to the one or more individuals. In some embodiments, one or more transmitting units 140 may transmit one or more signals that include information related to one or more nutraceutical formulations for administration to the one or more individuals. In some embodiments, one or more transmitting units 140 may transmit one or more signals that include information related to determining one or more nutraceutical associated parameters based on the results of processing. Information related to numerous types of formulations may be transmitted. Examples of such formulations include, but are not limited to, sublingual formulations, oral formulations, transdermal formulations, cream-based formulations, suppositories, inhaled formulations, nasally administered formulations, and the like.

At operation 3508, the transmitting operation 3230 may include transmitting the one or more signals that include information related to one or more health related recommendations for the one or more individuals. In some embodiments, one or more transmitting units 140 may transmit one or more signals that include information related to one or more health related recommendations for the one or more individuals. In some embodiments, one or more transmitting units 140 may transmit one or more signals that include information related to determining one or more nutraceutical associated parameters based on the results of processing. Information related to numerous types of health related recommendations may be transmitted. Examples of health related recommendations include, but are not limited to, recommendations related to eating habits, substance use, exercise, physical activities, sleep acquisition, and the like.

Figure 36:
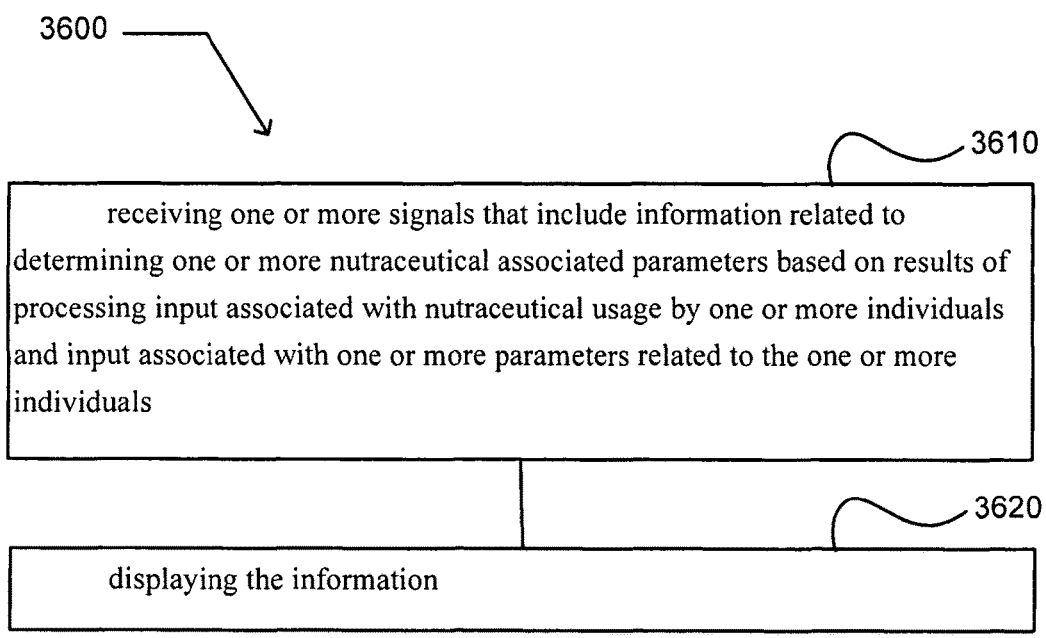
FIG. 36 illustrates an operational flow 3600 representing example operations related to receiving and displaying input related to one or more nutraceuticals.

FIG. 36 illustrates an operational flow 3600 representing examples of operations that are related to the performance of one or more methods related to one or more nutraceuticals. In FIG. 36 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 3600 includes a receiving operation 3610 involving receiving one or more signals that include information related to determining one or more nutraceutical associated parameters based on results of processing input associated with nutraceutical usage by one or more individuals and input associated with one or more parameters related to the one or more individuals. In some embodiments, the receiving operation 3610 may include receiving the one or more signals that include information related to one or more nutraceuticals for administration to the one or more individuals. In some embodiments, the receiving operation 3610 may include receiving the one or more signals that include information related to one or more concentrations of one or more nutraceuticals for administration to the one or more individuals. In some embodiments, the receiving operation 3610 may include receiving the one or more signals that include information related to one or more nutraceutical formulations for administration to the one or more individuals. In some embodiments, the receiving operation 3610 may include receiving the one or more signals that include information related to one or more health related recommendations for the one or more individuals.

After a start operation, the operational flow 3600 includes a displaying operation 3620 involving displaying the information. In some embodiments, the displaying operation 3620 may include displaying the results of the processing on one or more active displays. In some embodiments, the displaying operation 3620 may include displaying the results of the processing on one or more passive displays. In some embodiments, the displaying operation 3620 may include displaying the results of the processing in numeric format. In some embodiments, the displaying operation 3620 may include displaying the results of the processing in graphical format. In some embodiments, the displaying operation 3620 may include displaying the results of the processing in audio format. In some embodiments, the displaying operation 3620 may include displaying a comparison of one individual with one or more other individuals. In some embodiments, the displaying operation 3620 may include displaying one or more changes in the nutraceutical usage by the one or more individuals at two or more times. In some embodiments, the displaying operation 3620 may include displaying one or more changes in the one or more parameters related to the one or more individuals at two or more times. In some embodiments, the displaying operation 3620 may include displaying one or more changes in the nutraceutical usage by the one or more individuals at two or more times and one or more changes in the one or more parameters related to the one or more individuals at two or more times.

Figure 37:
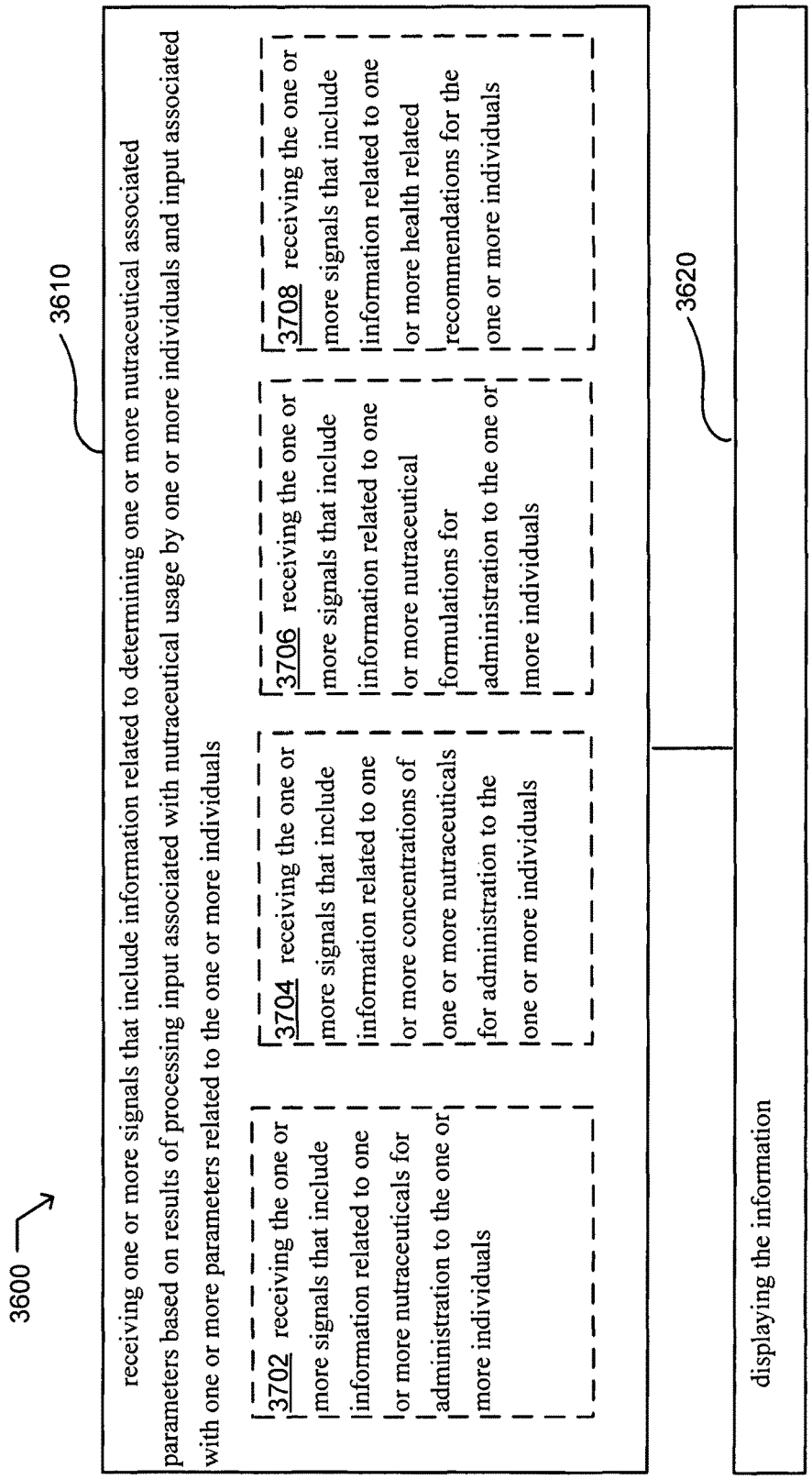
FIG. 37 illustrates alternative embodiments of the example operation flow of FIG. 36.

FIG. 37 illustrates alternative embodiments of the example operational flow 3600 of FIG. 36. FIG. 37 illustrates example embodiments where the receiving operation 3610 may include at least one additional operation. Additional operations may include an operation 3702, an operation 3704, an operation 3706, and/or an operation 3708.

At operation 3702, the receiving operation 3610 may include receiving the one or more signals that include information related to one or more nutraceuticals for administration to the one or more individuals. In some embodiments, one or more receiving units 150 may receive one or more signals that include information related to one or more nutraceuticals for administration to one or more individuals. For example, in some embodiments, one or more receiving units 150 may receive one or more signals that indicate nutraceuticals that do not contraindicate one or more pharmaceuticals being used by an individual. In some embodiments, one or more receiving units 150 may receive one or more signals that indicate one or more nutraceuticals that do not contraindicate one or more other nutraceuticals that are being used by an individual. In some embodiments, one or more receiving units 150 may receive one or more signals that indicate one or more nutraceuticals that may be used by an individual to attain one or more goals (e.g., weight loss, sleep acquisition, alertness, mood alteration, hormonal balance, weight gain). In some embodiments, one or more receiving units 150 may receive one or more signals that indicate one or more nutraceuticals that are to be used by an individual who has a propensity to develop a malady. For example, in some embodiments, one or more receiving units 150 may receive one or more signals that include information to select calcium supplements for administration to persons who exhibit symptoms of, or who may be at risk of developing, osteoporosis. In some embodiments, an individual may exhibit serotonin levels that are inconsistent with sleep acquisition during desired hours by an individual. Accordingly, one or more receiving units 150 may receive one or more signals that indicate one or more nutraceuticals for use by an individual to increase sleep acquisition. In some embodiments, the one or more receiving units 150 may receive one or more signals that indicate one or more nutraceuticals and suggest one or times for administration to an individual.

At operation 3704, the receiving operation 3610 may include receiving the one or more signals that include information related to one or more concentrations of one or more nutraceuticals for administration to the one or more individuals. In some embodiments, one or more receiving units 150 may receive one or more signals that include information related to one or more concentrations of one or more nutraceuticals for administration to one or more individuals. In some embodiments, one or more receiving units 150 may receive one or more signals that are associated with nutraceutical usage and one or more parameters related to an individual to indicate one or more concentrations of one or more nutraceuticals for administration to the individual. One or more receiving units 150 may receive one or more signals that may include numerous types of parameters. Examples of such parameters include, but are not limited to, weight, metabolism, activity level, exercise habits, goals, and the like. For example, in some embodiments, one or more receiving units 150 may receive one or more signals that indicate that a higher dosage of a nutraceutical is appropriate for a larger person and a lower dosage is appropriate for a smaller person. In some embodiments, one or more receiving units 150 may receive one or more signals that indicate one or more concentrations of one or more nutraceuticals that are within a range of concentrations. For example, in some embodiments, one or more receiving units 150 may receive one or more signals that indicate a range of concentrations of melotonin for administration to an individual that enable the individual to acquire a desired amount of sleep without causing the individual to be drowsy during daytime hours. Accordingly, one or more receiving units 150 may receive one or more signals that indicate numerous concentrations of numerous types of nutraceuticals for administration to an individual.

At operation 3706, the receiving operation 3610 may include receiving the one or more signals that include information related to one or more nutraceutical formulations for administration to the one or more individuals. In some embodiments, one or more receiving units 150 may receive one or more signals that include information related to one or more nutraceutical formulations for administration to one or more individuals. In some embodiments, one or more receiving units 150 may receive one or more signals that indicate one or more nutraceutical formulations for administration to the individual. Numerous formulations may be indicated. Examples of such formulations include, but are not limited to, sublingual formulations, oral formulations, transdermal formulations, cream-based formulations, suppositories, inhaled formulations, nasally administered formulations, and the like.

At operation 3708, the receiving operation 3610 may include receiving the one or more signals that include information related to one or more health related recommendations for the one or more individuals. In some embodiments, one or more receiving units 150 may receive one or more signals that include information related to one or more health related recommendations for one or more individuals. In some embodiments, one or more receiving units 150 may receive one or more signals that indicate one or more health related recommendations for one or more individuals. Examples of health related recommendations include, but are not limited to, recommendations related to eating habits, substance use, exercise, physical activities, sleep acquisition, and the like.

Figure 38:
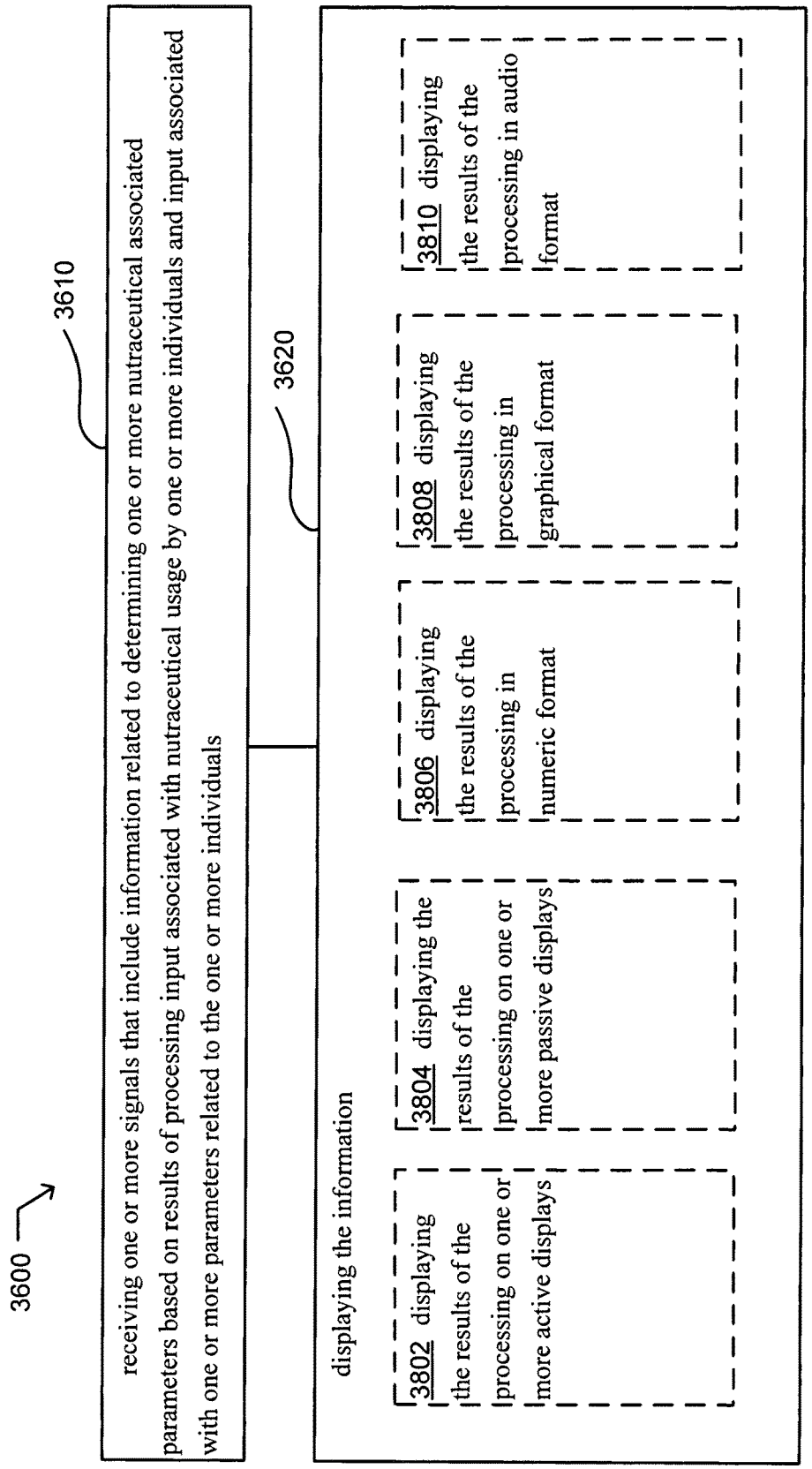
FIG. 38 illustrates alternative embodiments of the example operation flow of FIG. 36.

FIG. 38 illustrates alternative embodiments of the example operational flow 3600 of FIG. 36. FIG. 38 illustrates example embodiments where the displaying operation 3620 may include at least one additional operation. Additional operations may include an operation 3802, an operation 3804, an operation 3806, an operation 3808, and/or an operation 3810.

At operation 3802, the displaying operation 3620 may include displaying the results of the processing on one or more active displays. In some embodiments, one or more display units 130 may display results of processing on one or more active displays. Numerous active display units 130 are known and include, but are not limited to, quarter-video graphics array (QVGA), video graphics array (VGA), super video graphics array (SVGA), extended graphics array (XGA), wide extended graphics array (VGA), super extended graphics array (SXGA), ultra extended graphics array (UXGA), wide super extended graphics array (WSXGA), wide ultra extended graphics array (WUXGA).

At operation 3804, the displaying operation 3620 may include displaying the results of the processing on one or more passive displays. In some embodiments, one or more display units 130 may display results of processing on one or more passive displays. In some embodiments, one or display units 130 may include one or more liquid crystal displays (LCD). Methods to construct passive displays have been described (e.g., U.S. Pat. Nos. 4,807,967; 4,729,636; 4,436,378; 4,257,041; herein incorporated by reference).

At operation 3806, the displaying operation 3620 may include displaying the results of the processing in numeric format. In some embodiments, one or more display units 130 may display results of processing in numeric format.

At operation 3808, the displaying operation 3620 may include displaying the results of the processing in graphical format. In some embodiments, one or more display units 130 may display results of processing in graphical format. Numerous types of graphical formats may be used. Examples of such graphical formats include, but are not limited to, use of shapes, use of colors, use of symbols (e.g., smiley face, frowny face, thumbs up sign, thumbs down sign, histograms, bar graphs, pie charts, and the like).

At operation 3810, the displaying operation 3620 may include displaying the results of the processing in audio format. In some embodiments, one or more display units 130 may display results of processing in audio format. In some embodiments, the results of processing may be presented in voice format. For example, in some embodiments, a voice may tell an individual to increase, decrease, or maintain one or more dosages of one or more nutraceuticals. In some embodiments, sounds may be used to indicate changes in nutraceutical usage and/or parameters related to an individual. In some embodiments, applause, cheering, and the like may be used to indicate a positive change. Examples of positive changes include, but are not limited to, weight loss, lowered blood pressure, lowered heart rate, and the like. In some embodiments, booing, hissing, nagging, and the like may be used to indicate a negative change. Examples of negative changes include, but are not limited to, weight gain, increased blood pressure, increased heart rate, and the like.

Figure 39:
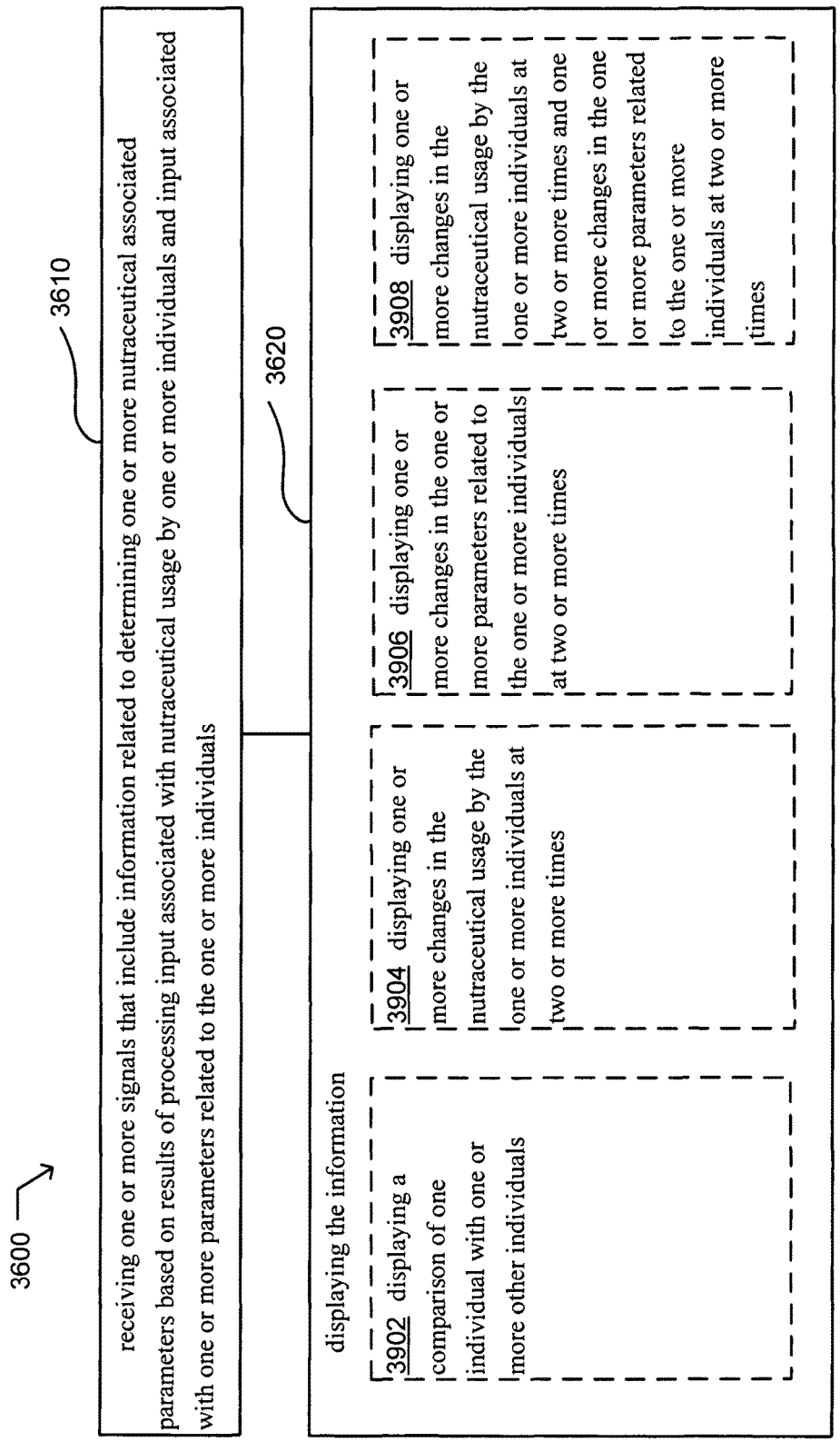
FIG. 39 illustrates alternative embodiments of the example operation flow of FIG. 36.

FIG. 39 illustrates alternative embodiments of the example operational flow 3600 of FIG. 36. FIG. 39 illustrates example embodiments where the displaying operation 3620 may include at least one additional operation. Additional operations may include an operation 3902, an operation 3904, an operation 3906, and/or an operation 3908.

At operation 3902, the displaying operation 3620 may include displaying a comparison of one individual with one or more other individuals. In some embodiments, one or more display units 130 may display a comparison of one individual with one or more other individuals. Numerous display formats may be used. In some embodiments, one or more runners may be depicted on a visual display as participating in a race such that an individual will be depicted according to their position in the race. For example, if an individual is leading a group in weight loss, they may be depicted as running in first place in a foot race. However, if the individual is behind a group in weight loss, they may be depicted as running in last place in a foot race. In some embodiments, individuals may be depicted as individual bars in a bar graph. In some embodiments, individuals may be depicted as slices of a pie chart. Accordingly, numerous formats may be used to display a comparison of an individual to one or more other individuals.

At operation 3904, the displaying operation 3620 may include displaying one or more changes in the nutraceutical usage by the one or more individuals at two or more times. In some embodiments, one or more display units 130 may display one or more changes in nutraceutical usage by one or more individuals at two or more times. For example, in some embodiments, one or more display units 130 may display changes in the dosage of one or more nutraceuticals relative to a starting dosage at two or more times. In some embodiments, one or more display units 130 may display changes in the formulation of one or more nutraceuticals relative to a starting formulation at two or more times. Numerous changes may be displayed.

At operation 3906, the displaying operation 3620 may include displaying one or more changes in the one or more parameters related to the one or more individuals at two or more times. In some embodiments, one or more display units 130 may display one or more changes in parameters related to one or more individuals at two or more times. For example, in some embodiments, one or more display units 130 may display changes in the weight of an individual at two or more times. Numerous changes may be displayed.

At operation 3908, the displaying operation 3620 may include displaying one or more changes in the nutraceutical usage by the one or more individuals at two or more times and one or more changes in the one or more parameters related to the one or more individuals at two or more times. In some embodiments, one or more display units 130 may display one or more changes in nutraceutical usage by one or more individuals at two or more times and one or more changes in parameters related to the one or more individuals at two or more times. Accordingly, changes in nutraceutical usage may be displayed relative to changes in parameters over time. In some embodiments, such a display may be used to titrate nutraceutical usage to achieve a desired result.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although user 170 is shown/described herein as a single illustrated figure, those skilled in the art will appreciate that a user 170 may be representative of a human user 170, a robotic user 170 (e.g., computational entity), and/or substantially any combination thereof (e.g., a user 170 may be assisted by one or more robotic). In addition, a user 170 as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A system, comprising:
   one or more microfluidic chips configured for performing analysis of two or more fluidic bodily samples collected at two or more different times;
   at least one computing device; and
   at least one non-transitory computer-readable medium including at least one or more instructions that, when executed by the at least one computing device, cause the at least one computing device to perform one or more operations including at least:
      controlling the one or more microfluidic chips to accept two or more fluidic bodily samples of one or more individuals collected at two or more different times;
      controlling the one or more microfluidic chips to perform at least one analysis of the two or more fluidic bodily samples of the one or more individuals;
      receiving one or more signals from the one or more microfluidic chips associated with the at least one analysis of the two or more fluidic bodily samples of the one or more individuals;
      inferring at least some information related to nutraceutical usage by the one or more individuals at least partially based on the one or more signals from the one or more microfluidic chips;
      receiving one or more values associated with the one or more individuals at two or more different times;
      comparing one or more values associated with the one or more individuals at a first time with one or more values associated with the one or more individuals at a second time;
      determining one or more changes in the one or more values associated with the one or more individuals at least partially based on the comparing the one or more values;
      determining at least one relationship between the nutraceutical usage by the one or more individuals and the one or more values associated with the one or more individuals at least partially based on the determining the one or more changes in the one or more values associated with the one or more individuals;
      determining at least one modification of one or more nutraceutical dosages at least partially based on the determining the at least one relationship between the nutraceutical usage by the one or more individuals and the one or more values associated with the one or more individuals; and
      presenting the at least one modification of the one or more nutraceutical dosages via at least one presentation device in a manner capable of being perceived by the one or more individuals.

2. The system of claim 1, wherein receiving one or more signals from the one or more microfluidic chips associated with the at least one analysis of the two or more fluidic bodily samples of the one or more individuals comprises:
   receiving one or more signals from the one or more microfluidic chips associated with the at least one analysis by the one or more microfluidic chips of two or more fluidic bodily samples including at least one of blood, urine, saliva, synovial fluid, or pleural fluid.

3. The system of claim 1, wherein receiving one or more signals from the one or more microfluidic chips associated with the at least one analysis of the two or more fluidic bodily samples of the one or more individuals comprises:
   receiving one or more signals from the one or more microfluidic chips associated with detection by the one or more microfluidic chips of one or more chromium salts in the two or more fluidic bodily samples of the one or more individuals providing at least one inference of use of one or more chromium nutraceuticals by the one or more individuals.

4. The system of claim 1, wherein receiving one or more signals from the one or more microfluidic chips associated with the at least one analysis of the two or more fluidic bodily samples of the one or more individuals comprises:
   receiving one or more signals from the one or more microfluidic chips associated with at least one analysis by the one or more microfluidic chips of two or more samples of peritoneal fluid of the one or more individuals.

5. The system of claim 4, wherein receiving one or more signals from the one or more microfluidic chips associated with at least one analysis by the one or more microfluidic chips of two or more samples of peritoneal fluid of the one or more individuals comprises:
   receiving one or more signals from the one or more microfluidic chips subsequent to one or more peritoneal administrations of one or more nutraceuticals to the one or more individuals, the one or more signals associated with the at least one analysis by the one or more microfluidic chips of the two or more samples of peritoneal fluid of the one or more individuals from one or more collections during the one or more peritoneal administrations of the one or more nutraceuticals to the one or more individuals.

6. The system of claim 1, wherein receiving one or more values associated with the one or more individuals at two or more different times comprises:
   receiving one or more values from one or more physiological data acquisition devices including at least some information related to one or more physiological parameters associated with the one or more individuals.

7. The system of claim 1, wherein receiving one or more values associated with the one or more individuals at two or more different times comprises:
   receiving the one or more values subsequent to the nutraceutical usage by the one or more individuals.

8. The system of claim 1, wherein determining at least one modification of one or more nutraceutical dosages at least partially based on the determining the at least one relationship between the nutraceutical usage by the one or more individuals and the one or more values associated with the one or more individuals comprises:
   determining at least one modification of one or more nutraceutical dosages at least partially based on at least one indication of at least one predisposition of the one or more individuals to develop at least one particular malady, including at least altering at least one dosage of at least one calcium supplement in accordance with the one or more individuals exhibiting one or more symptoms of osteoporosis.

9. The system of claim 1, wherein comparing one or more values associated with the one or more individuals at a first time with one or more values associated with the one or more individuals at a second time comprises:

comparing one or more values associated with at least one first individual at a first time with one or more values associated with at least one second individual at a second time.

10. The system of claim 1, wherein determining at least one modification of one or more nutraceutical dosages at least partially based on the determining the at least one relationship between the nutraceutical usage by the one or more individuals and the one or more values associated with the one or more individuals comprises:
   determining the at least one modification of the one or more nutraceutical dosages at least partially based on at least one input from one or more healthcare workers including at least one plan intended to achieve one or more individualized goals associated with the one or more individuals.

11. The system of claim 1, wherein determining at least one relationship between the nutraceutical usage by the one or more individuals and the one or more values associated with the one or more individuals at least partially based on the determining the one or more changes in the one or more values associated with the one or more individuals comprises:
   determining at least one potential relationship at least partially based on the one or more changes in the one or more values associated with the one or more individuals.

12. The system of claim 1, wherein determining at least one relationship between the nutraceutical usage by the one or more individuals and the one or more values associated with the one or more individuals at least partially based on the determining the one or more changes in the one or more values associated with the one or more individuals comprises:
   determining at least one relationship between at least one void in the nutraceutical usage by the one or more individuals and the one or more values associated with the one or more individuals.

13. The system of claim 1, wherein receiving one or more values associated with the one or more individuals at two or more different times comprises:
   receiving at least some information from at least some medical instrumentation related to one or more metabolic parameters measured by the at least some medical instrumentation and associated with the one or more individuals.

14. The system of claim 1, wherein determining at least one modification of one or more nutraceutical dosages at least partially based on the determining the at least one relationship between the nutraceutical usage by the one or more individuals and the one or more values associated with the one or more individuals comprises:
   determining at least one modification of one or more nutraceutical dosages intended to cause a change of one or more metabolic parameters associated with the one or more individuals.

15. The system of claim 1, wherein determining at least one modification of one or more nutraceutical dosages at least partially based on the determining the at least one relationship between the nutraceutical usage by the one or more individuals and the one or more values associated with the one or more individuals comprises:
   determining at least one modification of one or more nutraceutical dosages intended to contraindicate at least one nutraceutical used by the one or more individuals to cause a change of one or more metabolic parameters associated with the one or more individuals.

16. The system of claim 1, wherein determining at least one modification of one or more nutraceutical dosages at least partially based on the determining the at least one relationship between the nutraceutical usage by the one or more individuals and the one or more values associated with the one or more individuals comprises:
   identifying at least one substance intended to not contraindicate at least one nutraceutical used by the one or more individuals to cause a change of one or more metabolic parameters associated with the one or more individuals.

17. The system of claim 1, wherein presenting the at least one modification of the one or more nutraceutical dosages via at least one presentation device in a manner capable of being perceived by the one or more individuals comprises:
   transmitting one or more signals including at least some information related to the at least one modification of the one or more nutraceutical dosages for presentation via the at least one presentation device in a manner capable of being perceived by the one or more individuals.

18. The system of claim 17, wherein transmitting one or more signals including at least some information related to the at least one modification of the one or more nutraceutical dosages for presentation via the at least one presentation device in a manner capable of being perceived by the one or more individuals comprises:
   determining at least some information related to one or more health related recommendations for the one or more individuals at least partially based on the at least one modification of the one or more nutraceutical dosages; and
   transmitting one or more signals including the at least some information related to the one or more health related recommendations for the one or more individuals for presentation via the at least one presentation device in a manner capable of being perceived by the one or more individuals.

19. The system of claim 18, wherein determining at least some information related to one or more health related recommendations for the one or more individuals at least partially based on the at least one modification of the one or more nutraceutical dosages comprises:
   determining at least one modification to at least one of eating habits, substance use, exercise, physical activities, or sleep acquisition of the one or more individuals at least partially based on the at least one modification of the one or more nutraceutical dosages.

20. The system of claim 1, wherein controlling the one or more microfluidic chips to perform at least one analysis of the two or more fluidic bodily samples of the one or more individuals comprises:
   controlling the one or more microfluidic chips to mix the two or more fluidic bodily samples with a reaction mixture with one or more labeled components being tested.

21. The system of claim 1, wherein controlling the one or more microfluidic chips to perform at least one analysis of the two or more fluidic bodily samples of the one or more individuals comprises:
   controlling the one or more microfluidic chips to mix the two or more fluidic bodily samples with a reaction mixture with one or more labeled components being tested; and
   controlling the one or more microfluidic chips to pass the mixed reaction mixture over at least one of a field or array to which moieties that bind to the one or more labeled components are immobilized.

22. The system of claim 1, wherein controlling the one or more microfluidic chips to perform at least one analysis of the two or more fluidic bodily samples of the one or more individuals comprises:
controlling the one or more microfluidic chips to perform the at least one analysis of the two or more fluidic bodily samples of the one or more individuals in comparison with at least one of a control field or array embedded in the one or more microfluidic chips and associated with a particular nutraceutical compound.

23. The system of claim 1, wherein controlling the one or more microfluidic chips to perform at least one analysis of the two or more fluidic bodily samples of the one or more individuals comprises:
controlling the one or more microfluidic chips that have been calibrated to detect at least one particular nutraceutical associated component to perform the at least one analysis of the two or more fluidic bodily samples of the one or more individuals and detect a concentration of the at least one particular nutraceutical associated component within the two or more fluidic bodily samples.

24. The system of claim 1, wherein controlling the one or more microfluidic chips to perform at least one analysis of the two or more fluidic bodily samples of the one or more individuals comprises:
controlling the one or more microfluidic chips to mix the two or more fluidic bodily samples of the one or more individuals with one or more reagents configured for detecting presence of at least one particular nutraceutical associated component.

25. The system of claim 1, wherein controlling the one or more microfluidic chips to accept two or more fluidic bodily samples of one or more individuals collected at two or more different times comprises:
controlling at least one coupling of the one or more microfluidic chips to accept the two or more fluidic bodily samples of the one or more individuals at the two or more different times.

26. A method, comprising:
providing one or more microfluidic chips configured for performing analysis of two or more fluidic bodily samples collected at two or more different times;
providing at least one computing device; and
providing at least one non-transitory computer-readable medium including at least one or more instructions that, when executed by the at least one computing device, cause the at least one computing device to perform one or more operations including at least:
controlling the one or more microfluidic chips to accept two or more fluidic bodily samples of one or more individuals collected at two or more different times;
controlling the one or more microfluidic chips to perform at least one analysis of the two or more fluidic bodily samples of the one or more individuals;
receiving one or more signals from the one or more microfluidic chips associated with the at least one analysis of the two or more fluidic bodily samples of the one or more individuals;
inferring at least some information related to nutraceutical usage by the one or more individuals at least partially based on the one or more signals from the one or more microfluidic chips;
receiving one or more values associated with the one or more individuals at two or more different times;
comparing one or more values associated with the one or more individuals at a first time with one or more values associated with the one or more individuals at a second time;
determining one or more changes in the one or more values associated with the one or more individuals at least partially based on the comparing the one or more values;
determining at least one relationship between the nutraceutical usage by the one or more individuals and the one or more values associated with the one or more individuals at least partially based on the determining the one or more changes in the one or more values associated with the one or more individuals;
determining at least one modification of one or more nutraceutical dosages at least partially based on the determining the at least one relationship between the nutraceutical usage by the one or more individuals and the one or more values associated with the one or more individuals; and
presenting the at least one modification of the one or more nutraceutical dosages via at least one presentation device in a manner capable of being perceived by the one or more individuals.

27. A system, comprising:
one or more microfluidic chips configured for performing analysis of two or more fluidic bodily samples collected at two or more different times and including at least one or more sample loops;
a mouthpiece coupled with the one or more sample loops, the mouthpiece configured for accepting at least one of one or more breath samples or one or more saliva samples;
at least one presentation device;
at least one computing device; and
at least one non-transitory computer-readable medium including at least one or more instructions that, when executed by the at least one computing device, cause the at least one computing device to perform one or more operations including at least:
controlling the at least one presentation device to present at least one instruction to the one or more individuals to provide, via the mouthpiece, at least one of one or more breath samples or one or more saliva samples;
controlling the one or more microfluidic chips to accept two or more fluidic bodily samples of the one or more individuals collected at two or more different times, the two or more fluidic bodily samples accepted via the one or more sample loops and the coupled mouthpiece;
controlling the one or more microfluidic chips to perform at least one analysis of the two or more fluidic bodily samples of the one or more individuals;
receiving one or more signals from the one or more microfluidic chips associated with the at least one analysis of the two or more fluidic bodily samples of the one or more individuals;
inferring at least some information related to nutraceutical usage by the one or more individuals at least partially based on the one or more signals from the one or more microfluidic chips;
receiving one or more values associated with the one or more individuals at two or more different times;

comparing one or more values associated with the one or more individuals at a first time with one or more values associated with the one or more individuals at a second time;
determining one or more changes in the one or more values associated with the one or more individuals at least partially based on the comparing the one or more values;
determining at least one relationship between the nutraceutical usage by the one or more individuals and the one or more values associated with the one or more individuals at least partially based on the determining the one or more changes in the one or more values associated with the one or more individuals;
determining at least one modification of one or more nutraceutical dosages at least partially based on the determining the at least one relationship between the nutraceutical usage by the one or more individuals and the one or more values associated with the one or more individuals; and
presenting the at least one modification of the one or more nutraceutical dosages via the at least one presentation device in a manner capable of being perceived by the one or more individuals.

28. A system, comprising:

one or more microfluidic chips configured for performing analysis of two or more fluidic bodily samples collected at two or more different times and including at least one or more capillary tubes coupled via one or more sample loops of the one or more microfluidic chips;
one or more lancets configured for receiving one or more blood samples resulting from a finger stick of one or more individuals with the one or more lancets;
at least one presentation device;
at least one computing device; and
at least one non-transitory computer-readable medium including at least one or more instructions that, when executed by the at least one computing device, cause the at least one computing device to perform one or more operations including at least:
  controlling the at least one presentation device to present at least one instruction to the one or more individuals to perform at least one finger stick with at least one lancet;
  controlling the at least one presentation device to present at least one instruction to the one or more individuals to insert at least one capillary tube coupled via the one or more sample loops of the one or more microfluidic chips into a blood sample resulting from the at least one finger stick with the at least one lancet;
  controlling the one or more microfluidic chips to accept two or more fluidic bodily samples including two or more blood samples of the one or more individuals collected at two or more different times, the two or more fluidic bodily samples accepted via the one or more sample loops and the coupled one or more capillary tubes;
  controlling the one or more microfluidic chips to perform at least one analysis of the two or more fluidic bodily samples of the one or more individuals;
  receiving one or more signals from the one or more microfluidic chips associated with the at least one analysis of the two or more fluidic bodily samples of the one or more individuals;
  inferring at least some information related to nutraceutical usage by the one or more individuals at least partially based on the one or more signals from the one or more microfluidic chips;
  receiving one or more values associated with the one or more individuals at two or more different times;
  comparing one or more values associated with the one or more individuals at a first time with one or more values associated with the one or more individuals at a second time;
  determining one or more changes in the one or more values associated with the one or more individuals at least partially based on the comparing the one or more values;
  determining at least one relationship between the nutraceutical usage by the one or more individuals and the one or more values associated with the one or more individuals at least partially based on the determining the one or more changes in the one or more values associated with the one or more individuals;
  determining at least one modification of one or more nutraceutical dosages at least partially based on the determining the at least one relationship between the nutraceutical usage by the one or more individuals and the one or more values associated with the one or more individuals; and
  presenting the at least one modification of the one or more nutraceutical dosages via the at least one presentation device in a manner capable of being perceived by the one or more individuals.

* * * * *